United States Patent
Kitade et al.

(10) Patent No.: US 8,912,181 B2
(45) Date of Patent: Dec. 16, 2014

(54) BICYCLIC COMPOUND OR SALT THEREOF

(75) Inventors: Makoto Kitade, Nagareyama (JP); Satoshi Yamashita, Tsukuba (JP); Shuichi Ohkubo, Hanno (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/978,613

(22) PCT Filed: Jan. 6, 2012

(86) PCT No.: PCT/JP2012/050141
§ 371 (c)(1),
(2), (4) Date: Jul. 8, 2013

(87) PCT Pub. No.: WO2012/093708
PCT Pub. Date: Jul. 12, 2012

(65) Prior Publication Data
US 2013/0296320 A1    Nov. 7, 2013

(30) Foreign Application Priority Data
Jan. 7, 2011    (JP) ................. 2011-002104

(51) Int. Cl.
| | | |
|---|---|---|
| C07D 401/04 | (2006.01) | |
| C07D 401/14 | (2006.01) | |
| A61K 31/47 | (2006.01) | |
| C07D 403/04 | (2006.01) | |
| A61K 31/4375 | (2006.01) | |
| A61K 31/4709 | (2006.01) | |
| A61K 31/4725 | (2006.01) | |
| A61K 31/497 | (2006.01) | |
| A61K 31/501 | (2006.01) | |
| A61K 31/506 | (2006.01) | |
| A61K 31/517 | (2006.01) | |
| A61K 31/5377 | (2006.01) | |
| C07D 403/14 | (2006.01) | |
| C07D 413/04 | (2006.01) | |
| C07D 417/04 | (2006.01) | |
| C07D 471/04 | (2006.01) | |

(52) U.S. Cl.
CPC .......... *C07D 403/04* (2013.01); *A61K 31/4375* (2013.01); *A61K 31/4709* (2013.01); *A61K 31/4725* (2013.01); *A61K 31/497* (2013.01); *A61K 31/501* (2013.01); *A61K 31/506* (2013.01); *A61K 31/517* (2013.01); *A61K 31/5377* (2013.01); *C07D 401/04* (2013.01); *C07D 401/14* (2013.01); *C07D 403/14* (2013.01); *C07D 413/04* (2013.01); *C07D 417/04* (2013.01); *C07D 471/04* (2013.01)
USPC ................. 514/235.2; 514/249; 514/252.04; 514/255.05; 514/256; 514/266.23; 514/300; 514/303; 514/307; 514/314; 544/128; 544/238; 544/284; 544/333; 544/350; 544/405; 546/113; 546/118; 546/146; 546/167

(58) Field of Classification Search
None
See application file for complete search history.

(56) References Cited

U.S. PATENT DOCUMENTS

| | | |
|---|---|---|
| 2004/0034061 A1 | 2/2004 | Nakazato et al. |
| 2007/0185184 A1 | 8/2007 | Hanson et al. |
| 2008/0119457 A1 | 5/2008 | Huang et al. |
| 2011/0015190 A1 | 1/2011 | Huang et al. |
| 2011/0028464 A1 | 2/2011 | Tsantrizos et al. |
| 2011/0039889 A1 | 2/2011 | Eldred et al. |
| 2011/0166169 A1 | 7/2011 | Ruxer et al. |

(Continued)

FOREIGN PATENT DOCUMENTS

| | | |
|---|---|---|
| CN | 1439001 A | 8/2003 |
| CN | 101180278 A | 5/2008 |

(Continued)

OTHER PUBLICATIONS

Extended European Search Report issued Jun. 30, 2014, in European Patent Application No. 12732119.8.

(Continued)

*Primary Examiner* — Zinna Northington Davis
(74) *Attorney, Agent, or Firm* — Oblon, Spivak, McClelland, Maier & Neustadt, L.L.P.

(57) ABSTRACT

A novel bicyclic compound having an HSP90 inhibitory effect and a carcinostatic effect. A pharmaceutical agent based on the HSP90 inhibitory effect and useful in the prevention and/or treatment of a disease involving HSP90, particularly cancer. The compound has a general formula (I) or is a salt thereof wherein at least one of $X^1$, $X^2$, $X^3$, and $X^4$ represents N or N-oxide and the rest thereof are each independently C—$R^2$; any one or two of $Y^1$, $Y^2$, $Y^3$, and $Y^4$ represent C—$R^4$ and the rest thereof are each independently CH or N; $R^1$ represents an optionally substituted monocyclic or bicyclic unsaturated heterocyclic group having 1 to 4 heteroatoms selected from N, S, and O; $R^2$ represents a hydrogen atom, an optionally substituted alkyl group having 1 to 6 carbon atoms etc.; $R^3$ represents a hydrogen atom, —CO—$R^5$ etc.

(I)

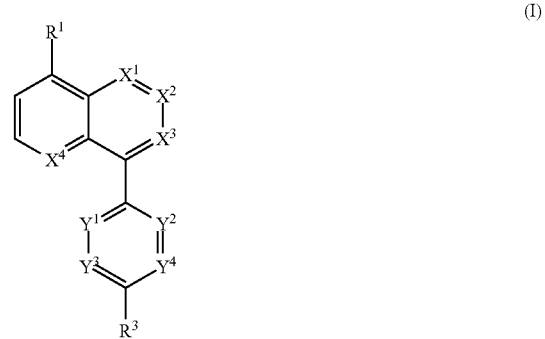

11 Claims, No Drawings

(56) References Cited

U.S. PATENT DOCUMENTS

| 2011/0281908 A1 | 11/2011 | Sun et al. |
| 2012/0010241 A1 | 1/2012 | Bertin et al. |
| 2012/0108589 A1 | 5/2012 | Kitade et al. |

FOREIGN PATENT DOCUMENTS

| JP | 57-203068 A | 12/1982 |
| JP | 2004-502685 A | 1/2004 |
| WO | WO 2007/035620 A2 | 3/2007 |
| WO | WO 2008/024978 A2 | 2/2008 |
| WO | WO 2008/026704 A1 | 3/2008 |
| WO | WO 2009/062289 A1 | 5/2009 |
| WO | WO 2009/073777 A1 | 6/2009 |
| WO | WO 2009/122034 A2 | 10/2009 |
| WO | WO 2009/122034 A3 | 10/2009 |
| WO | WO 2009/122034 A8 | 10/2009 |
| WO | WO 2009/133136 A1 | 11/2009 |
| WO | WO 2010/042489 A2 | 4/2010 |
| WO | WO 2010/042489 A3 | 4/2010 |
| WO | WO 2010/106290 A1 | 9/2010 |
| WO | WO 2011/004610 A1 | 1/2011 |

OTHER PUBLICATIONS

International Search Report and Written Opinion issued Feb. 28, 2012, in PCT/JP2012/050141 filed Jan. 6, 2012 with English translation.

Henry Gilman et al., "Some substituted isoquinolines", Journal of the American Chemical Society, vol. 69, XP-055118250, Aug. 1947, pp. 1946-1948.

Thota Ganesh, et al., "Discovery of aminoquinolines as a new class of potent inhibitors of heat shock protein 90 (Hsp90): Synthesis, biology, and molecular modeling", Bioorganic & Medicinal Chemistry, vol. 16, No. 14, XP-022941559, Jul. 15, 2008, pp. 6903-6910.

Office Action issued on Jun. 26, 2014 in the corresponding Chinese Patent Application No. 201280004872.4 (with English translation of summary).

U.S. Appl. No. 13/978,632, filed Jul. 8, 2013, Kitade et al.

Whitesell, L. et al., "HSP90 and the Chaperoning of Cancer", Nature Reviews Cancer, vol. 5, pp. 761 to 772, (Oct. 2005).

Kamal, A. et al., "Therapeutic and diagnostic implications of Hsp90 activation", TRENDS in Molecular Medicine, vol. 10, No. 6, pp. 283 to 290, (Jun. 2004).

Banerji, U., "Heat Shock Protein 90 as a Drug Target: Some Like It Hot", Clin Cancer Res, vol. 15, No. 1, pp. 9 to 14, (Jan. 1, 2009).

Taldone, T. et al., "Targeting Hsp90: small-molecule inhibitors and their clinical development", Current Opinion in Pharmacology, vol. 8, pp. 370 to 374, (2008).

Li, Y. et al., "New developments in Hsp90 inhibitors as anti-cancer therapeutics: Mechanisms, clinical perspective and more potential", Drug Resistance Updates, vol. 12, pp. 17 to 27, (2009).

Luo, W. et al., "Heat shock protein 90: translation from cancer to Alzheimer's disease treatment", BMC Neuroscience, vol. 9 (Suppl. 2): S7, pp. 1 to 8, (2008).

International Search Report Issued Apr. 3, 2012 in PCT/JP12/50140 Filed Jan. 6, 2012.

U.S. Appl. No. 14/242,063, filed Apr. 1, 2014, Kitade et al.

BICYCLIC COMPOUND OR SALT THEREOF

CROSS REFERENCE TO RELATED APPLICATIONS

The present application is a 35 U.S.C. §371 national stage patent application of International patent application PCT/JP2012/050141, filed on Jan. 6, 2012, published as WO/2012/093708 on Jul. 12, 2012, the text of which is incorporated by reference, and claims the benefit of the filing date of Japanese application no. 2011-002104, filed on Jan. 7, 2011, the text of which is also incorporated by reference.

FIELD OF THE INVENTION

The present invention relates to a bicyclic compound or a salt thereof, and a pharmaceutical agent comprising the same, particularly, an agent for prevention and/or treatment of cancer etc. based on an HSP90 inhibitory effect.

BACKGROUND OF THE INVENTION

A group of proteins called molecular chaperones have various functions such as the formation promotion or maintenance of functional structures of other proteins, the promotion of normal association, the prevention of unnecessary aggregation, protection from degradation, and the promotion of secretion (Non Patent Document 1). The molecular chaperone HSP90 is found as abundant as approximately 1 to 2% of all intracellular soluble proteins and, unlike other chaperone proteins, is not required for the biosynthesis of the majority of polypeptides (Non Patent Document 1). Signaling-related factors (e.g., ERBB1/EGFR, ERBB2/HER2, MET, IGF1R, KDR/VEGFR, FLT3, ZAP70, KIT, CHUK/IKK, BRAF, RAF1, SRC, and AKT), cell cycle regulatory factors (e.g., CDK4, CDK6, Cyclin D, PLK1, and BIRC5), and transcriptional regulators (e.g., HIF-1α, p53, androgen receptor, estrogen receptor, and progesterone receptor) are known as main client proteins whose structural formation or stability is controlled through interaction with HSP90 (Non Patent Documents 2 and 3). HSP90 is deeply involved in cell growth and survival by maintaining the normal functions of these proteins. In addition, HSP90 is required for the normal functions of mutant or chimeric factors (e.g., BCR-ABL and NPM-ALK) which cause malignant transformation or cancer exacerbation, indicating the importance of HSP90, particularly, for processes such as malignant transformation and the survival, growth, exacerbation, and metastasis of cancer (Non Patent Document 2).

When the chaperone functions of HSP90 are suppressed by a specific inhibitor such as geldanamycin, its client protein is inactivated, destabilized, and degraded, resulting in induced cell growth arrest or apoptosis (Non Patent Document 4). In terms of the physiological functions of HSP90, such an HSP90 inhibitor is characterized by being capable of simultaneously inhibiting a plurality of signaling pathways involved in cancer survival and growth and as such, can serve as a drug having extensive and effective anticancer effects. Also, the HSP90 inhibitor is expected to serve as a drug with high cancer selectivity from the finding that cancer cell-derived HSP90 is more highly active than normal cell-derived HSP90 and has high affinity for ATP or inhibitors (Non Patent Document 5).

A plurality of HSP90 inhibitors are currently under clinical development as anticancer agents. Development of the geldanamycin derivative 17-allylamino-17-desmethoxygeldanamycin (17-AAG), which is most ahead of others, is underway as a single agent and is also under trial in combination with various anticancer agents (Non Patent Documents 3 and 4). Unfortunately, the problems of 17-AAG, such as poor solubility, instability in solutions, low oral absorbability, and hepatotoxicity, have been pointed out (Non Patent Documents 4 and 5). Thus, a new type of HSP90 inhibitor has been demanded. Reportedly, these HSP90 inhibitors not only have anticancer effects but may serve as therapeutic agents for, for example, autoimmune diseases, inflammatory diseases, central nervous system diseases (such as Parkinson's disease, Alzheimer's disease, and Huntington's disease), viral infectious diseases, cardiovascular diseases (Non Patent Documents 2 and 6).

CITATION LIST

Patent Document

[Patent Document 1] International Publication No. WO2007/035620

[Patent Document 2] International Publication No. WO2008/024978

Non Patent Document

[Non Patent Document 1] Nature Reviews Cancer 5, 761-772 (2005)

[Non Patent Document 2] TRENDS in Molecular Medicine 6, 17-27 (2004)

[Non Patent Document 3] Clin Can Res 15, 9-14 (2009)

[Non Patent Document 4] Current Opinion in Pharmacology 8, 370-374 (2008)

[Non Patent Document 5] Drug Resistance Updates 12, 17-27 (2009)

[Non Patent Document 6] BMC Neuroscience 9 (Suppl 2), 2008

SUMMARY OF THE INVENTION

Problems to be Solved by the Invention

An object of the present invention is to provide a novel bicyclic compound which has an HSP90 inhibitory effect and a carcinostatic effect. Another object of the present invention is to provide a pharmaceutical agent which is based on the HSP90 inhibitory effect and is useful in the prevention and/or treatment of a disease involving HSP90, particularly, cancer.

Means for Solving the Problem

The present inventors have conducted diligent studies on a compound having an HSP90 inhibitory effect and consequently found that a novel compound represented by the general formula (I) shown below wherein $R^1$ represents a monocyclic or bicyclic unsaturated heterocyclic group has an excellent inhibitory effect on HSP90, further has an excellent cytostatic effect on cancer cells, and is useful as an agent for prevention or treatment of a disease involving HSP90, particularly, an anticancer agent. On the basis of the findings, the present invention has been completed.

Specifically, the present invention provides a compound represented by the following general formula (I) or a salt thereof:

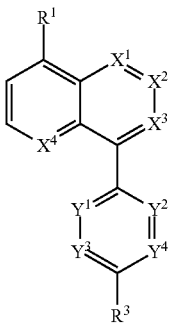

(I)

wherein at least one of $X^1$, $X^2$, $X^3$, and $X^4$ represents N or N-oxide and the rest thereof are the same or different and each represent C—$R^2$;

any one or two of $Y^1$, $Y^2$, $Y^3$, and $Y^4$ represent C—$R^4$ and the rest thereof are the same or different and each represent CH or N;

$R^1$ represents an optionally substituted monocyclic or bicyclic unsaturated heterocyclic group having 1 to 4 heteroatoms selected from N, S, and O;

$R^2$ represents a hydrogen atom, an optionally substituted alkyl group having 1 to 6 carbon atoms, an optionally substituted cycloalkyl group having 3 to 7 carbon atoms, or an optionally substituted alkenyl group having 2 to 6 carbon atoms;

$R^3$ represents a hydrogen atom, a halogen atom, a cyano group, an alkyl group having 1 to 6 carbon atoms, an alkoxy group having 1 to 6 carbon atoms, or —CO—$R^5$;

$R^4$ represents a hydrogen atom, a halogen atom, an alkyl group having 1 to 6 carbon atoms, an alkoxy group having 1 to 6 carbon atoms, —CO—$R^6$, —N($R^7$)($R^8$), or —S—$R^9$;

$R^5$ represents a hydroxyl group, an amino group, or an optionally substituted alkylamino group having 1 to 6 carbon atoms;

$R^6$ represents a hydroxyl group, an amino group optionally having a hydroxyl group, or an optionally substituted alkylamino group having 1 to 6 carbon atoms;

$R^7$ and $R^8$ are the same or different and each represent a hydrogen atom, an optionally substituted alkyl group having 1 to 6 carbon atoms, an optionally substituted cycloalkyl group having 3 to 7 carbon atoms, an optionally substituted aromatic hydrocarbon group, an optionally substituted saturated heterocyclic group, or an optionally substituted unsaturated heterocyclic group, or $R^7$ and $R^8$ together form a saturated heterocyclic group together with the nitrogen atom bonded thereto; and $R^9$ represents an optionally substituted cycloalkyl group having 3 to 7 carbon atoms, or an optionally substituted aromatic hydrocarbon group.

The present invention also provides a pharmaceutical agent comprising the compound represented by the general formula (I) or the salt thereof.

The present invention further provides a pharmaceutical composition comprising the compound represented by the general formula (I) or the salt thereof, and a pharmaceutically acceptable carrier.

The present invention further provides the compound represented by the general formula (I) or the salt thereof for the prevention or treatment of a disease involving HSP90, particularly, cancer.

The present invention further provides use of the compound represented by the general formula (I) or the salt thereof for the production of an agent for prevention or treatment of a disease involving HSP90, particularly, cancer.

The present invention further provides a method for preventing or treating a disease involving HSP90, particularly, cancer, comprising administering an effective amount of the compound represented by the general formula (I) or the salt thereof.

Effects of the Invention

The present invention provides a novel compound represented by the general formula (I) or a salt thereof, which is useful as an HSP90 inhibitor.

The compound of the present invention or the salt thereof has been shown to have excellent HSP90 inhibitory activity and exhibit a cytostatic effect on cancer cells. Thus, the compound of the present invention or the salt thereof is useful as an agent for prevention and/or treatment of a disease involving HSP90, for example, cancer, based on the excellent HSP90 inhibitory effect.

DETAILED DESCRIPTION OF THE INVENTION

The compound of the present invention represented by the general formula (I) is a bicyclic compound characteristically having a monocyclic or bicyclic unsaturated heterocyclic group at position 8 of a skeleton such as quinoline or quinazoline or at position 5 of a skeleton such as isoquinoline, and is a novel compound which has not been described in any of the Documents of Citation List.

In the present specification, examples of the "substituent" include a halogen atom, a hydroxyl group, a cyano group, an amino group, a nitro group, an oxo group, a carboxyl group, a carbamoyl group, an alkyl group, a cycloalkyl group, an alkenyl group, an alkynyl group, an alkoxy group, an acyl group, an acyloxy group, an alkoxycarbonyl group, a saturated heterocyclic group, an unsaturated heterocyclic group, an aromatic hydrocarbon group, a halogenoalkyl group, an aralkyl group, an unsaturated heterocyclic alkyl group, an alkylamino group, an acylamino group, an alkoxycarbonylamino group, an aralkyloxy group, an aminoacyloxy group, an unsaturated heterocyclic acyloxy group, and an alkyl-unsaturated heterocyclic group. The number of the substituent, if present, is typically 1 to 3.

Examples of the halogen atom as the substituent include a chlorine atom, a bromine atom, a fluorine atom, and an iodine atom.

The alkyl group as the substituent preferably refers to a linear or branched alkyl group having 1 to 6 carbon atoms. Examples thereof include a methyl group, an ethyl group, a n-propyl group, an isopropyl group, a n-butyl group, an isobutyl group, a sec-butyl group, a tert-butyl group, a pentyl group, and a hexyl group.

The cycloalkyl group as the substituent preferably refers to a cycloalkyl group having 3 to 7 carbon atoms. Examples thereof include a cyclopropyl group, a cyclobutyl group, a cyclopentyl group, a cyclohexyl group, and a cycloheptyl group.

The alkenyl group as the substituent preferably refers to an alkenyl group having 2 to 6 carbon atoms and containing a carbon-carbon double bond. Examples thereof include a vinyl group, an allyl group, a methylvinyl group, a propenyl group, a butenyl group, a pentenyl group, and a hexenyl group.

The alkynyl group as the substituent preferably refers to an alkynyl group having 2 to 6 carbon atoms and containing a carbon-carbon triple bond. Examples thereof include an ethynyl group and a propargyl group.

The alkoxy group as the substituent preferably refers to a linear or branched alkoxy group having 1 to 6 carbon atoms. Examples thereof include a methoxy group, an ethoxy group, a n-propoxy group, an isopropoxy group, a n-butoxy group, an isobutoxy group, and a tert-butoxy group.

The acyl group as the substituent preferably refers to an alkanoyl group having 1 to 6 carbon atoms or an aroyl group having 7 to 12 carbon atoms. Examples thereof include a formyl group, an acetyl group, a propionyl group, a n-butyryl group, an isobutyryl group, a valeryl group, an isovaleryl group, a pivaloyl group, and a benzoyl group.

The acyloxy group as the substituent refers to an oxy group substituted by the acyl group as exemplified above and is preferably an oxy group substituted by an alkanoyl group having 1 to 6 carbon atoms or an aroyl group having 7 to 12 carbon atoms. Examples thereof include a formyloxy group, an acetoxy group, a propionyloxy group, a n-butyryloxy group, an isobutyryloxy group, a valeryloxy group, an isovaleryloxy group, a pivaloyloxy group, and a benzoyloxy group.

The alkoxycarbonyl group as the substituent refers to a carbonyl group substituted by the alkoxy group as exemplified above and is preferably a carbonyl group substituted by an alkoxy group having 1 to 6 carbon atoms. Examples thereof include a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, and a tert-butoxycarbonyl group.

The saturated heterocyclic group as the substituent preferably refers to a monocyclic or bicyclic 5- to 10-membered saturated heterocyclic group having 1- to 4 heteroatoms selected from N, S, and O. Examples thereof include a pyrrolidinyl group, a piperidinyl group, a piperazinyl group, a hexamethyleneimino group, a morpholino group, a thiomorpholino group, a homopiperazinyl group, a tetrahydrofuranyl group, a tetrahydropyranyl group, a methylenedioxyphenyl group, an ethylenedioxyphenyl group, and a dihydrobenzofuranyl group.

The unsaturated heterocyclic group as the substituent preferably refers to a monocyclic or bicyclic 5- to 10-membered unsaturated heterocyclic group having 1 to 4 heteroatoms selected from N, S, and O. Examples thereof include an imidazolyl group, a thienyl group, a furyl group, a pyrrolyl group, an oxazolyl group, an isoxazolyl group, a thiazolyl group, an isothiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a benzofuranyl group, a benzimidazolyl group, a benzoxazolyl group, a benzothiazolyl group, a purinyl group, a quinolyl group, an isoquinolyl group, a quinazolinyl group, and a quinoxalyl group.

The aromatic hydrocarbon group as the substituent preferably refers to an aromatic hydrocarbon group having 6 to 14 carbon atoms. Examples thereof include a phenyl group and a naphthyl group.

The halogenoalkyl group as the substituent refers to a group in which one to all hydrogen atoms of the alkyl group as exemplified above are replaced by the halogen atom(s) as exemplified above, and is preferably a group in which one to all hydrogen atoms of the linear or branched alkyl group having 1 to 6 carbon atoms are replaced by the halogen atom(s). Examples thereof include a difluoromethyl group and a trifluoromethyl group.

The aralkyl group as the substituent preferably refers to a linear or branched alkyl group having 1 to 6 carbon atoms substituted by an aromatic hydrocarbon group having 6 to 14 carbon atoms. Examples thereof include a benzyl group, a phenylethyl group, a phenylpropyl group, a naphthylmethyl group, and a naphthylethyl group.

The saturated heterocyclic alkyl group as the substituent refers to the alkyl group, as exemplified above, substituted by the saturated heterocyclic group as exemplified above and is preferably the linear or branched alkyl group having 1 to 6 carbon atoms substituted by a monocyclic 5- to 7-membered saturated heterocyclic group having 1 or 2 heteroatoms selected from N, S, and O. Examples thereof include a morpholinomethyl group and a piperidinylethyl group.

The alkylamino group as the substituent refers to an amino group monosubstituted or disubstituted by the alkyl group as exemplified above and is preferably an amino group monosubstituted or disubstituted by a linear or branched alkyl group having 1 to 6 carbon atoms. Examples thereof include a methylamino group, an ethylamino group, a diethylamino group, a methylethylamino group, a cyclobutylmethylamino group, a dimethylaminomethyl group, and a 2-hydroxyethyl (methyl)aminomethyl group.

The acylamino group as the substituent refers to an amino group substituted by the acyl group as exemplified above and is preferably an amino group substituted by an alkanoyl group having 1 to 6 carbon atoms or an aroyl group having 7 to 12 carbon atoms. Examples thereof include a formylamino group, an acetylamino group, a propionylamino group, a butyrylamino group, a 2-methylpropionylamino group, a pivaloylamino group, a pentanoylamino group, a 3-methylbutyrylamino group, and a hexanoylamino group.

The alkoxycarbonylamino group as the substituent refers to an amino group substituted by the alkoxycarbonyl group as exemplified above and is preferably an amino group substituted by a carbonyl group bonded to an alkoxy group having 1 to 6 carbon atoms. Examples thereof include a methoxycarbonylamino group, an ethoxycarbonylamino group, a propoxycarbonylamino group, an isopropoxycarbonylamino group, a n-butoxycarbonylamino group, an isobutoxycarbonylamino group, a sec-butoxycarbonylamino group, and a tert-butoxycarbonylamino group.

The aralkyloxy group as the substituent refers to an oxy group having the aralkyl group as exemplified above and is preferably an oxy group substituted by a linear or branched alkyl group having 1 to 6 carbon atoms bonded to an aromatic hydrocarbon group having 6 to 14 carbon atoms. Examples thereof include a benzyloxy group, a phenethyloxy group, a phenylpropyloxy group, a naphthylmethyloxy group, and a naphthylethyloxy group.

The aminoacyloxy group as the substituent refers to an oxy group substituted by the acyl group, as exemplified above, bonded to an amino group and is preferably an oxy group substituted by an alkanoyl group having 1 to 6 carbon atoms or an aroyl group having 7 to 12 carbon atoms bonded to an amino group. Examples thereof include an aminoacetoxy group, a 2-aminopropionyloxy group, and a 2-amino-4-methylpentanoyloxy group.

The saturated heterocyclic acyloxy group as the substituent refers to an oxy group substituted by the acyl group, as exemplified above, bonded to the saturated heterocyclic group as exemplified above and is preferably an oxy group substituted by the alkanoyl group having 1 to 6 carbon atoms or the aroyl group having 7 to 12 carbon atoms bonded to the monocyclic or bicyclic 5- to 10-membered saturated heterocyclic group having 1 to 4 heteroatoms selected from N, S, and O. Examples thereof include a morpholinoacetoxy group.

In the general formula (I), at least one of $X^1$, $X^2$, $X^3$, and $X^4$ represents N or N-oxide and the rest thereof are the same or different and each represent C—$R^2$. Preferably, in the general formula (I), $X^2$ is C—$R^2$, at least one of $X^1$, $X^3$, and $X^4$ is N or N-oxide and each of the rest of $X^1$, $X^3$, and $X^4$ is CH. Examples of the bicyclic skeleton in the general formula (I) based on these definitions of $X^1$ to $X^4$ include the following structures:
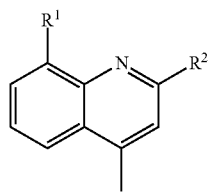 (A-1)
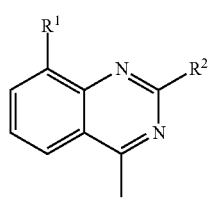 (A-2)
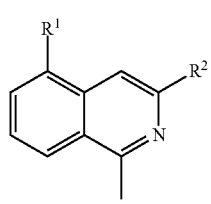 (A-3)
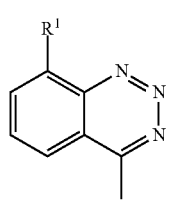 (A-4)
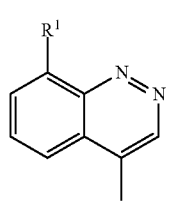 (A-5)
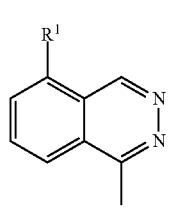 (A-6)
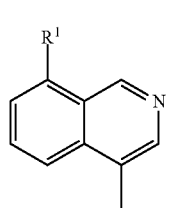 (A-7)
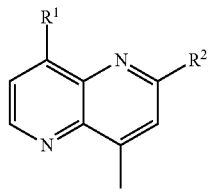 (A-8)
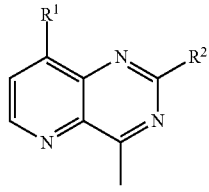 (A-9)
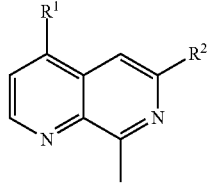 (A-10)
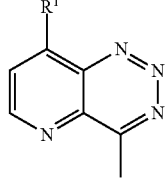 (A-11)
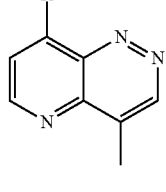 (A-12)
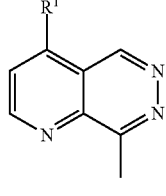 (A-13)
(A-14)
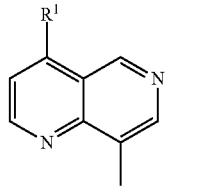 (A-15)
wherein $R^1$ and $R^2$ are as defined above.

Of these skeletons, (A-1), (A-2), (A-3), (A-8), (A-9), (A-10), and (A-15) are preferred. Particularly, (A-1), (A-2), and (A-3) are preferred.

In the general formula (I), the "monocyclic or bicyclic unsaturated heterocyclic group having 1 to 4 heteroatoms selected from N, S, and O" in the "optionally substituted monocyclic or bicyclic unsaturated heterocyclic group having 1 to 4 heteroatoms selected from N, S, and O" represented by $R^1$ is preferably a monocyclic or bicyclic 5- to 10-membered unsaturated heterocyclic group having 1 to 3 heteroatoms selected from N, S, and O, more preferably a monocyclic 5- to 6-membered unsaturated heterocyclic group having 1 to 3 heteroatoms selected from N, S, and O, or a bicyclic 9- to 10-membered unsaturated heterocyclic group having 1 to 3 heteroatoms selected from N, S, and O. Examples of the unsaturated heterocyclic group include an imidazolyl group, a pyrazolyl group, a thienyl group, a furyl group, a pyrrolyl group, an oxazolyl group, an isoxazolyl group, a thiazolyl group, an isothiazolyl group, a pyrazolyl group, a triazolyl group, a tetrazolyl group, a pyridyl group, a pyrazyl group, a pyrimidinyl group, a pyridazinyl group, an indolyl group, an isoindolyl group, a pyrrolopyridyl group, an indazolyl group, a methylenedioxyphenyl group, an ethylenedioxyphenyl group, a benzofuranyl group, a dihydrobenzofuranyl group, a benzimidazolyl group, a benzoxazolyl group, a benzothiazolyl group, a purinyl group, a quinolyl group, a tetrahydroquinolyl group, an isoquinolyl group, a quinazolinyl group, and a quinoxalinyl group. The unsaturated heterocyclic group is preferably an imidazolyl group, a thiazolyl group, an oxadiazolyl group, a thiadiazolyl group, a pyridyl group, a pyrazyl group, a pyrimidinyl group, a pyridazinyl group, a pyridopyrazyl group, a quinolyl group, an imidazopyridyl group, or a pyrrolopyridyl group, more preferably a quinolyl group, an imidazopyridyl group, a pyridopyrazyl group, a pyridyl group, an imidazolyl group, a pyrrolopyridyl group, or a pyrimidinyl group, further preferably a quinolyl group, an imidazopyridyl group, a pyridyl group, an imidazolyl group, or a pyrrolopyridyl group, particularly preferably a quinolyl group, a pyridyl group, or an imidazolyl group.

In the general formula (I), examples of the "substituent" in the unsaturated heterocyclic group represented by $R^1$ include the substituent as exemplified above. The number thereof is 1 to 3. The substituent is preferably a halogen atom, an amino group, an optionally substituted alkyl group having 1 to 6 carbon atoms, an optionally substituted alkoxy group having 1 to 6 carbon atoms, an optionally substituted alkylamino group having 1 to 6 carbon atoms, an optionally substituted acyl group having 1 to 6 carbon atoms, an optionally substituted carbamoyl group, an optionally substituted acylamino group having 1 to 6 carbon atoms, an optionally substituted aromatic hydrocarbon group, an optionally substituted unsaturated heterocyclic group, or an optionally substituted saturated heterocyclic group.

The substituent is more preferably a halogen atom; an amino group; an alkyl group having 1 to 6 carbon atoms and optionally having a substituent selected from a hydroxyl group, an amino group, an alkoxycarbonylamino group having 1 to 6 carbon atoms, and a saturated heterocyclic group; an alkoxy group having 1 to 6 carbon atoms; an alkylamino group having 1 to 6 carbon atoms and optionally having a cycloalkyl group having 3 to 7 carbon atoms; an acyl group having 1 to 6 carbon atoms; a carbamoyl group optionally having a substituent selected from an alkyl group having 1 to 6 carbon atoms, a saturated heterocyclic group optionally substituted by an alkyl group having 1 to 6 carbon atoms, and an aromatic hydrocarbon group; an acylamino group having 1 to 6 carbon atoms and optionally having a hydroxyl group; an unsaturated heterocyclic group optionally having a substituent selected from an alkyl group having 1 to 6 carbon atoms and a halogenoalkyl group having 1 to 6 carbon atoms; or an aromatic hydrocarbon group.

The substituent is even more preferably a halogen atom; an amino group; an alkyl group having 1 to 6 carbon atoms and optionally having a hydroxyl group; an alkoxy group having 1 to 6 carbon atoms; an alkylamino group having 1 to 6 carbon atoms; an acyl group having 1 to 6 carbon atoms; an acylamino group having 1 to 6 carbon atoms and optionally having a hydroxyl group; an unsaturated heterocyclic group optionally having a substituent selected from an alkyl group having 1 to 6 carbon atoms and a halogenoalkyl group having 1 to 6 carbon atoms; or an aromatic hydrocarbon group.

The substituent is further preferably an alkyl group having 1 to 6 carbon atoms; an alkylamino group having 1 to 6 carbon atoms; an acyl group having 1 to 6 carbon atoms; an acylamino group having 1 to 6 carbon atoms and optionally having a hydroxyl group; or an unsaturated heterocyclic group optionally having a substituent selected from an alkyl group having 1 to 6 carbon atoms and a halogenoalkyl group having 1 to 6 carbon atoms.

Examples of the halogen atom which may substitute on the unsaturated heterocyclic group represented by $R^1$ include the halogen atom as exemplified above. A bromine atom is preferred.

Examples of the "optionally substituted alkyl group having 1 to 6 carbon atoms" which may substitute on the unsaturated heterocyclic group represented by $R^1$ include the alkyl group having 1 to 6 carbon atoms as exemplified above which optionally has the substituent. An alkyl group having 1 to 6 carbon atoms and optionally having a substituent selected from a hydroxyl group, an amino group, an alkoxycarbonylamino group having 1 to 6 carbon atoms, and a saturated heterocyclic group is preferred. More specifically, for example, a methyl group, an ethyl group, a n-propyl group, an isopropyl group, a hydroxymethyl group, an aminoethyl group, a tert-butoxycarbonylaminoethyl group, a morpholinomethyl group is preferred.

Examples of the "optionally substituted alkoxy group having 1 to 6 carbon atoms" which may substitute on the unsaturated heterocyclic group represented by $R^1$ include the alkoxy group having 1 to 6 carbon atoms as exemplified above which optionally has the substituent. An unsubstituted alkoxy group having 1 to 6 carbon atoms is preferred. More specifically, a methoxy group or an ethoxy group is preferred.

Examples of the "optionally substituted alkylamino group having 1 to 6 carbon atoms" which may substitute on the unsaturated heterocyclic group represented by $R^1$ include the alkylamino group having 1 to 6 carbon atoms as exemplified above which optionally has the substituent. An alkylamino group having 1 to 6 carbon atoms and optionally having a cycloalkyl group having 3 to 7 carbon atoms is preferred. More specifically, for example, a methylamino group, an ethylamino group, a n-propylamino group, a cyclobutylmethylamino group is preferred.

The "optionally substituted acyl group" which may substitute on the unsaturated heterocyclic group represented by $R^1$ include the acyl group having 1 to 6 carbon atoms as exemplified above which optionally has the substituent. An unsubstituted acyl group having 1 to 6 carbon atoms is preferred. More specifically, for example, a formyl group, an acetyl group, a propionyl group is preferred.

The "optionally substituted carbamoyl group" which may substitute on the unsaturated heterocyclic group represented by $R^1$ include the carbamoyl group as exemplified above which optionally has the substituent. A carbamoyl group optionally having a substituent selected from an alkyl group having 1 to 6 carbon atoms, a saturated heterocyclic group optionally substituted by an alkyl group having 1 to 6 carbon atoms, and an aromatic hydrocarbon group is preferred. More specifically, for example, a methylcarbamoyl group, an ethylcarbamoyl group, a n-propylcarbamoyl group, a (1-methylpiperidin-4-yl)carbamoyl group, a phenylcarbamoyl group is preferred.

Examples of the "optionally substituted acylamino group having 1 to 6 carbon atoms" which may substitute on the unsaturated heterocyclic group represented by $R^1$ include the acylamino group having 1 to 6 carbon atoms as exemplified above which optionally has the substituent. An acylamino group having 1 to 6 carbon atoms and optionally having a hydroxyl group is preferred. More specifically, an acetylamino group, a 2-hydroxyacetylamino group, or a propionylamino group is preferred.

Examples of the "optionally substituted unsaturated heterocyclic group" which may substitute on the unsaturated heterocyclic group represented by $R^1$ include the unsaturated heterocyclic group as exemplified above which optionally has the substituent. An unsaturated heterocyclic group optionally having a substituent selected from an alkyl group having 1 to 6 carbon atoms and a halogenoalkyl group having 1 to 6 carbon atoms is preferred. More specifically, a 1-methyl-1H-pyrazol-4-yl group, a 1-ethyl-1H-pyrazol-4-yl group, a 1-isopropyl-1H-pyrazol-4-yl group, a 1-isobutyl-1H-pyrazol-4-yl group, a 1-difluoromethyl-1H-pyrazol-4-yl group, a 1-oxidopyridin-3-yl group, a pyridin-3-yl group, a pyridin-4-yl group, or a 6-methylpyridin-3-yl group is preferred.

Examples of the "optionally substituted aromatic hydrocarbon group" which may substitute on the unsaturated heterocyclic group represented by $R^1$ include the aromatic hydrocarbon group as exemplified above which optionally has the substituent. An unsubstituted aromatic hydrocarbon group is preferred. More specifically, for example, a phenyl group, a naphthyl group is preferred.

$R^1$ is preferably an optionally substituted monocyclic or bicyclic 5- to 10-membered unsaturated heterocyclic group having 1 to 3 heteroatoms selected from N, S, and O, more preferably a monocyclic or bicyclic 5- to 10-membered unsaturated heterocyclic group having 1 to 3 heteroatoms selected from N, S, and O and optionally having a substituent selected from a halogen atom, an amino group, an optionally substituted alkyl group having 1 to 6 carbon atoms, an optionally substituted alkoxy group having 1 to 6 carbon atoms, an optionally substituted alkylamino group having 1 to 6 carbon atoms, an optionally substituted acyl group having 1 to 6 carbon atoms, an optionally substituted acylamino group having 1 to 6 carbon atoms, an optionally substituted carbamoyl group, an optionally substituted aromatic hydrocarbon group, an optionally substituted unsaturated heterocyclic group, and an optionally substituted saturated heterocyclic group.

Of these groups, a monocyclic 5- to 6-membered unsaturated heterocyclic group having 1 to 3 heteroatoms selected from N, S, and O or a bicyclic 9- to 10-membered unsaturated heterocyclic group having 1 to 3 heteroatoms selected from N, S, and O is more preferred, which optionally has a substituent selected from: a halogen atom; an amino group; an alkyl group having 1 to 6 carbon atoms and optionally having a substituent selected from a hydroxyl group, an amino group, an alkoxycarbonylamino group having 1 to 6 carbon atoms, and a saturated heterocyclic group; an alkoxy group having 1 to 6 carbon atoms; an alkylamino group having 1 to 6 carbon atoms and optionally having a cycloalkyl group having 3 to 7 carbon atoms; an acyl group having 1 to 6 carbon atoms; a carbamoyl group optionally having a substituent selected from an alkyl group having 1 to 6 carbon atoms, a saturated heterocyclic group optionally substituted by an alkyl group having 1 to 6 carbon atoms, and an aromatic hydrocarbon group; an acylamino group having 1 to 6 carbon atoms and optionally having a hydroxyl group; an unsaturated heterocyclic group optionally having a substituent selected from an alkyl group having 1 to 6 carbon atoms and a halogenoalkyl group having 1 to 6 carbon atoms; and an aromatic hydrocarbon group.

Also, $R^1$ is even more preferably a monocyclic 5- to 6-membered unsaturated heterocyclic group having 1 to 3 heteroatoms selected from N, S, and O and optionally having a substituent selected from: a halogen atom; an amino group; an alkyl group having 1 to 6 carbon atoms and optionally having a substituent selected from a hydroxyl group, an amino group, an alkoxycarbonylamino group having 1 to 6 carbon atoms, and a saturated heterocyclic group; an alkoxy group having 1 to 6 carbon atoms; an alkylamino group having 1 to 6 carbon atoms and optionally having a cycloalkyl group having 3 to 7 carbon atoms; an acyl group having 1 to 6 carbon atoms; a carbamoyl group optionally having a substituent selected from an alkyl group having 1 to 6 carbon atoms, a saturated heterocyclic group optionally substituted by an alkyl group having 1 to 6 carbon atoms, and an aromatic hydrocarbon group; an acylamino group having 1 to 6 carbon atoms and optionally having a hydroxyl group; an unsaturated heterocyclic group optionally having a substituent selected from an alkyl group having 1 to 6 carbon atoms and a halogenoalkyl group having 1 to 6 carbon atoms; and an aromatic hydrocarbon group, or even more preferably a bicyclic 9- to 10-membered unsaturated heterocyclic group having 1 to 3 heteroatoms selected from N, S, and O and optionally having a substituent selected from an alkyl group having 1 to 6 carbon atoms and optionally having a saturated heterocyclic group, and an acyl group having 1 to 6 carbon atoms.

$R^1$ is further preferably a monocyclic 5- to 6-membered unsaturated heterocyclic group having 1 to 3 heteroatoms selected from N, S, and O and optionally having a substituent selected from: a halogen atom; an amino group; an alkyl group having 1 to 6 carbon atoms and optionally having a substituent selected from a hydroxyl group, an amino group, and an alkoxycarbonylamino group having 1 to 6 carbon atoms; an alkoxy group having 1 to 6 carbon atoms; an alkylamino group having 1 to 6 carbon atoms and optionally having a cycloalkyl group having 3 to 7 carbon atoms; an acylamino group having 1 to 6 carbon atoms and optionally having a hydroxyl group; an unsaturated heterocyclic group optionally having a substituent selected from an alkyl group having 1 to 6 carbon atoms and a halogenoalkyl group having 1 to 6 carbon atoms; and an aromatic hydrocarbon group, or further preferably a bicyclic 9- to 10-membered unsaturated heterocyclic group having 1 to 3 heteroatoms selected from N, S, and O and optionally having a substituent selected from an alkyl group having 1 to 6 carbon atoms and optionally having a saturated heterocyclic group, and an acyl group having 1 to 6 carbon atoms.

$R^1$ is further preferably a monocyclic 5- to 6-membered unsaturated heterocyclic group having 1 to 3 heteroatoms selected from N, S, and O and optionally having a substituent selected from: an alkyl group having 1 to 6 carbon atoms; an alkylamino group having 1 to 6 carbon atoms; an acylamino group having 1 to 6 carbon atoms and optionally having a hydroxyl group; and an unsaturated heterocyclic group optionally having a substituent selected from an alkyl group having 1 to 6 carbon atoms and a halogenoalkyl group having 1 to 6 carbon atoms, or further preferably a bicyclic 9- to 10-membered unsaturated heterocyclic group having 1 to 3 heteroatoms selected from N, S, and O and optionally having a substituent selected from an alkyl group having 1 to 6 carbon atoms and an acyl group having 1 to 6 carbon atoms.

$R^1$ is further preferably a monocyclic 5- to 6-membered unsaturated heterocyclic group having 1 to 3 heteroatoms selected from N, S, and O or a bicyclic 9- to 10-membered unsaturated heterocyclic group having 1 to 3 heteroatoms selected from N, S, and O, which optionally has a substituent selected from: a halogen atom; an amino group; an alkyl group having 1 to 6 carbon atoms and optionally having a substituent selected from a hydroxyl group, an amino group, an alkoxycarbonylamino group having 1 to 6 carbon atoms, and a saturated heterocyclic group; an alkoxy group having 1 to 6 carbon atoms; an alkylamino group having 1 to 6 carbon atoms and optionally having a cycloalkyl group having 3 to 7 carbon atoms; an acyl group having 1 to 6 carbon atoms; a carbamoyl group optionally having a substituent selected from an alkyl group having 1 to 6 carbon atoms, a saturated heterocyclic group optionally substituted by an alkyl group having 1 to 6 carbon atoms, and an aromatic hydrocarbon group; an acylamino group having 1 to 6 carbon atoms and optionally having a hydroxyl group; an unsaturated heterocyclic group optionally having a substituent selected from an alkyl group having 1 to 6 carbon atoms and a halogenoalkyl group having 1 to 6 carbon atoms; and an aromatic hydrocarbon group, wherein the monocyclic or bicyclic unsaturated heterocyclic group is an imidazolyl group, a pyrazolyl group, a thienyl group, a furyl group, a pyrrolyl group, an oxazolyl group, an isoxazolyl group, a thiazolyl group, an isothiazolyl group, a pyrazolyl group, a triazolyl group, a tetrazolyl group, a pyridyl group, a pyrazyl group, a pyrimidinyl group, a pyridazinyl group, an indolyl group, an isoindolyl group, a pyrrolopyridyl group, an indazolyl group, a methylenedioxyphenyl group, an ethylenedioxyphenyl group, a benzofuranyl group, a dihydrobenzofuranyl group, a benzimidazolyl group, a benzoxazolyl group, a benzothiazolyl group, a purinyl group, a quinolyl group, a tetrahydroquinolyl group, an isoquinolyl group, a quinazolinyl group, or a quinoxalyl group.

$R^1$ is further preferably a monocyclic 5- to 6-membered unsaturated heterocyclic group having 1 to 3 heteroatoms selected from N, S, and O and optionally having a substituent selected from: a halogen atom; an amino group; an alkyl group having 1 to 6 carbon atoms and optionally having a substituent selected from a hydroxyl group, an amino group, an alkoxycarbonylamino group having 1 to 6 carbon atoms, and a saturated heterocyclic group; an alkoxy group having 1 to 6 carbon atoms; an alkylamino group having 1 to 6 carbon atoms and optionally having a cycloalkyl group having 3 to 7 carbon atoms; an acyl group having 1 to 6 carbon atoms; a carbamoyl group optionally having a substituent selected from an alkyl group having 1 to 6 carbon atoms, a saturated heterocyclic group optionally substituted by an alkyl group having 1 to 6 carbon atoms, and an aromatic hydrocarbon group; an acylamino group having 1 to 6 carbon atoms and optionally having a hydroxyl group; an unsaturated heterocyclic group optionally having a substituent selected from an alkyl group having 1 to 6 carbon atoms and a halogenoalkyl group having 1 to 6 carbon atoms; and an aromatic hydrocarbon group, or further preferably a bicyclic 9- to 10-membered unsaturated heterocyclic group having 1 to 3 heteroatoms selected from N, S, and O and optionally having a substituent selected from an alkyl group having 1 to 6 carbon atoms and optionally having a saturated heterocyclic group, and an acyl group having 1 to 6 carbon atoms, wherein the monocyclic or bicyclic unsaturated heterocyclic group is an imidazolyl group, a pyrazolyl group, a thienyl group, a furyl group, a pyrrolyl group, an oxazolyl group, an isoxazolyl group, a thiazolyl group, an isothiazolyl group, a pyrazolyl group, a triazolyl group, a tetrazolyl group, a pyridyl group, a pyrazyl group, a pyrimidinyl group, a pyridazinyl group, an indolyl group, an isoindolyl group, a pyrrolopyridyl group, an indazolyl group, a methylenedioxyphenyl group, an ethylenedioxyphenyl group, a benzofuranyl group, a dihydrobenzofuranyl group, a benzimidazolyl group, a benzoxazolyl group, a benzothiazolyl group, a purinyl group, a quinolyl group, a tetrahydroquinolyl group, an isoquinolyl group, a quinazolinyl group, or a quinoxalyl group.

$R^1$ is further preferably a monocyclic 5- to 6-membered unsaturated heterocyclic group having 1 to 3 heteroatoms selected from N, S, and O and optionally having a substituent selected from: a halogen atom; an amino group; an alkyl group having 1 to 6 carbon atoms and optionally having a substituent selected from a hydroxyl group, an amino group, and an alkoxycarbonylamino group having 1 to 6 carbon atoms; an alkoxy group having 1 to 6 carbon atoms; an alkylamino group having 1 to 6 carbon atoms and optionally having a cycloalkyl group having 3 to 7 carbon atoms; an acylamino group having 1 to 6 carbon atoms and optionally having a hydroxyl group; an unsaturated heterocyclic group optionally having a substituent selected from an alkyl group having 1 to 6 carbon atoms and a halogenoalkyl group having 1 to 6 carbon atoms; and an aromatic hydrocarbon group, or further preferably a bicyclic 9- to 10-membered unsaturated heterocyclic group having 1 to 3 heteroatoms selected from N, S, and O and optionally having a substituent selected from an alkyl group having 1 to 6 carbon atoms and optionally having a saturated heterocyclic group, and an acyl group having 1 to 6 carbon atoms, wherein the monocyclic or bicyclic unsaturated heterocyclic group is an imidazolyl group, a thiazolyl group, an oxadiazolyl group, a thiadiazolyl group, a pyridyl group, a pyrazyl group, a pyrimidinyl group, a pyridazinyl group, a pyridopyrazyl group, a quinolyl group, an imidazopyridyl group, or a pyrrolopyridyl group.

$R^1$ is further preferably an unsaturated heterocyclic group selected from an imidazolyl group, a thiazolyl group, an oxadiazolyl group, a thiadiazolyl group, a pyridyl group, a pyrazyl group, a pyrimidinyl group, and a pyridazinyl group, optionally having a substituent selected from: an alkyl group having 1 to 6 carbon atoms; an alkylamino group having 1 to 6 carbon atoms; an acylamino group having 1 to 6 carbon atoms and optionally having a hydroxyl group; and an unsaturated heterocyclic group optionally having a substituent selected from an alkyl group having 1 to 6 carbon atoms and a halogenoalkyl group having 1 to 6 carbon atoms, or further preferably an unsaturated heterocyclic group selected from a pyridopyrazyl group, a quinolyl group, an imidazopyridyl group, and a pyrrolopyridyl group, optionally having a substituent selected from an alkyl group having 1 to 6 carbon atoms and an acyl group having 1 to 6 carbon atoms.

$R^1$ is particularly preferably an imidazolyl group or a pyridyl group optionally having a substituent selected from: an alkyl group having 1 to 6 carbon atoms; an alkylamino group having 1 to 6 carbon atoms; an acylamino group having 1 to 6 carbon atoms and optionally having a hydroxyl group; and an unsaturated heterocyclic group optionally having a substituent selected from an alkyl group having 1 to 6 carbon atoms and a halogenoalkyl group having 1 to 6 carbon atoms, or particularly preferably a quinolyl group optionally having a substituent selected from an alkyl group having 1 to 6 carbon atoms and an acyl group having 1 to 6 carbon atoms.

Specifically, preferable examples of $R^1$ include a thiazol-5-yl group, a 2-phenylthiazol-5-yl group, a 5-phenyl-1,3,4- oxadiazol-2-yl group, a 5-phenyl-1,3,4-thiadiazol-2-yl group, a 4-bromo-1H-imidazol-1-yl group, a 4-acetyl-1H-imidazol-1-yl group, a 4-phenyl-1H-imidazol-1-yl group, a 4-(pyridin-3-yl)-1H-imidazol-1-yl group, a 4-(pyridin-4-yl)-1H-imidazol-1-yl group, a 4-(1-oxidopyridin-3-yl)-1H-imidazol-1-yl group, a 4-(6-methylpyridin-3-yl)-1H-imidazol-1-yl group, a 4-(1-methyl-1H-pyrazol-4-yl)-1H-imidazol-1-yl group, a 4-(1-ethyl-1H-pyrazol-4-yl)-1H-imidazol-1-yl group, a 4-(1-isopropyl-1H-pyrazol-4-yl)-1H-imidazol-1-yl group, a 4-(1-isobutyl-1H-pyrazol-4-yl)-1H-imidazol-1-yl group, a 4-(1-difluoromethyl-1H-pyrazol-4-yl)-1H-imidazol-1-yl group, a 5-(6-ethylamino)pyrazin-2-yl group, a pyridin-3-yl group, a 5-aminopyridin-3-yl group, a 5-(hydroxymethyl)pyridin-3-yl group, a 5-(2-aminoethyl)pyridin-3-yl group, a 5-(tert-butoxycarbonylaminoethyl)pyridin-3-yl group, a 5-(morpholinomethyl)pyridin-3-yl group, a 5-methoxypyridin-3-yl group, a 6-methoxypyridin-3-yl group, a 5-(methylamino)pyridin-3-yl group, a 5-(propylamino)pyridin-3-yl group, a 5-(cyclobutylmethylamino)pyridin-3-yl group, a 5-acetamidopyridin-3-yl group, a 5-(2-hydroxyacetamido)pyridin-3-yl group, a 6-methylcarbamoyl-pyridin-3-yl group, a 4-propylcarbamoyl-pyridin-3-yl group, a 5-(1-methylpiperidin-4-yl)carbamoyl-pyridin-3-yl group, a 6-phenylcarbamoyl-pyridin-3-yl group, a pyrimidin-5-yl group, a 6-methoxypyridazin-3-yl group, a quinolin-3-yl group, a 6-methylquinolin-3-yl group, a 7-methylquinolin-3-yl group, a 6-(morpholinomethyl)quinolin-3-yl group, a 7-formylquinolin-3-yl group, a 1H-imidazo[4,5-b]pyridin-6-yl group, a 2-methyl-1H-imidazo[4,5-b]pyridin-6-yl group, a 2-ethyl-1H-imidazo[4,5-b]pyridin-6-yl group, a 7-methyl-1H-imidazo[4,5-b]pyridin-6-yl group, a 1H-pyrrolo[2,3-b]pyridin-5-yl group, a 1H-pyrrolo[3,2-b]pyridin-6-yl group, and a pyrido[2,3-b]pyrazin-7-yl group. $R^1$ is more preferably a 4-(1-methyl-1H-pyrazol-4-yl)-1H-imidazol-1-yl group, a quinolin-3-yl group, a 4-(pyridin-3-yl)-1H-imidazol-1-yl group, a 4-(6-methylpyridin-3-yl)-1H-imidazol-1-yl group, a 4-(1-difluoromethyl-1H-pyrazol-4-yl)-1H-imidazol-1-yl group, a 4-(pyridin-4-yl)-1H-imidazol-1-yl group, a 4-phenyl-1H-imidazol-1-yl group, or a 4-(1-ethyl-1H-pyrazol-4-yl)-1H-imidazol-1-yl group, particularly preferably a 4-(1-methyl-1H-pyrazol-4-yl)-1H-imidazol-1-yl group, a quinolin-3-yl group, or a 4-(pyridin-3-yl)-1H-imidazol-1-yl group.

In the general formula (I), examples of the "optionally substituted alkyl group having 1 to 6 carbon atoms" represented by $R^2$ include the alkyl group having 1 to 6 carbon atoms as exemplified above which optionally has the substituent. An alkyl group having 1 to 6 carbon atoms and optionally having a substituent selected from a halogen atom and a saturated heterocyclic group is preferred. More specifically, a methyl group, an ethyl group, a n-propyl group, an isopropyl group, a n-butyl group, an isobutyl group, a sec-butyl group, a tert-butyl group, a pentyl group, a hexyl group, a trifluoromethyl group, or a morpholinomethyl group is preferred.

In the general formula (I), examples of the "optionally substituted cycloalkyl group having 3 to 7 carbon atoms" represented by $R^2$ include the cycloalkyl group having 3 to 7 carbon atoms as exemplified above which optionally has the substituent. An unsubstituted cycloalkyl group having 3 to 7 carbon atoms is preferred. More specifically, a cyclopropyl group is preferred.

In the general formula (I), examples of the "optionally substituted alkenyl group having 2 to 6 carbon atoms" represented by $R^2$ include the alkenyl group having 2 to 6 carbon atoms as exemplified above which optionally has the substituent. An unsubstituted alkenyl group having 2 to 6 carbon atoms is preferred. More specifically, a vinyl group is preferred.

$R^2$ is preferably a hydrogen atom; an alkyl group having 1 to 6 carbon atoms and optionally having a substituent selected from a halogen atom and a saturated heterocyclic group; or a cycloalkyl group having 3 to 7 carbon atoms, more preferably a hydrogen atom; an alkyl group having 1 to 6 carbon atoms and optionally having a halogen atom; or a cycloalkyl group having 3 to 7 carbon atoms.

Any one or two of $Y^1, Y^2, Y^3$, and $Y^4$ represent C—$R^4$ and the rest thereof are the same or different and each represent CH or N. Of them, preferably, $Y^4$ is C—$R^4$ or N and each of $Y^1$ to $Y^3$ is CH, or each of $Y^2$ to $Y^4$ is CH and $Y^1$ is C—$R^4$. These preferred aspects are represented by the following structural formulas:

(b1)

(b2)

(b3)

wherein $R^3$ and $R^4$ are as defined above.

Of these structures, (b1) and (b2) are more preferred, and (b1) is particularly preferred.

In the general formula (I), examples of the "halogen atom" represented by $R^3$ include the halogen atom as exemplified above. A bromine atom is preferred.

In the general formula (I), examples of the "alkyl group having 1 to 6 carbon atoms" represented by $R^3$ include the alkyl group as exemplified above. A methyl group is preferred.

In the general formula (I), examples of the "alkoxy group having 1 to 6 carbon atoms" represented by $R^3$ include the alkoxy group as exemplified above. A methoxy group is preferred.

$R^3$ is preferably a hydrogen atom, a cyano group, an alkoxy group having 1 to 6 carbon atoms, or —CO—$R^5$, more preferably a cyano group or —CO—$R^5$, further preferably —CO—$R^5$.

In the general formula (I), examples of the "optionally substituted alkylamino group having 1 to 6 carbon atoms" represented by $R^5$ include the alkylamino group having 1 to 6 carbon atoms as exemplified above which optionally has the substituent. An alkylamino group having 1 to 6 carbon atoms and optionally having an alkylamino group having 1 to 6 carbon atoms (the alkyl moiety is optionally substituted by a hydroxyl group) is preferred. More specifically, a 2-hydroxyethylmethylaminomethylamino group or a dimethylaminomethylamino group is preferred.

$R^5$ is more preferably an amino group or an alkylamino group having 1 to 6 carbon atoms and optionally having an alkylamino group having 1 to 6 carbon atoms (the alkyl moiety is optionally substituted by a hydroxyl group), particularly preferably an amino group.

In the general formula (I), examples of the "halogen atom" represented by $R^4$ include the halogen atom as exemplified above. A chlorine atom or a fluorine atom is preferred.

In the general formula (I), examples of the "alkyl group having 1 to 6 carbon atoms" represented by $R^4$ include the alkyl group having 1 to 6 carbon atoms as exemplified above. A methyl group, an ethyl group, a n-propyl group, or an isopropyl group is preferred.

In the general formula (I), examples of the "alkoxy group having 1 to 6 carbon atoms" represented by $R^4$ include the alkoxy group having 1 to 6 carbon atoms as exemplified above. A methoxy group is preferred.

$R^4$ is preferably a hydrogen atom, a halogen atom, an alkyl group having 1 to 6 carbon atoms, an alkoxy group having 1 to 6 carbon atoms, or —$N(R^7)(R^8)$, more preferably a halogen atom, an alkyl group having 1 to 6 carbon atoms, or —$N(R^7)(R^8)$, particularly preferably —$N(R^7)(R^8)$.

In the general formula (I), examples of the "optionally substituted alkylamino group having 1 to 6 carbon atoms" represented by $R^6$ include the alkylamino group having 1 to 6 carbon atoms as exemplified above which optionally has the substituent.

$R^6$ is preferably an amino group or an alkylamino group having 1 to 6 carbon atoms, particularly preferably an amino group.

In the general formula (I), examples of the "optionally substituted alkyl group having 1 to 6 carbon atoms" represented by $R^7$ or $R^8$ include the alkyl group having 1 to 6 carbon atoms as exemplified above which optionally has the substituent. An alkyl group having 1 to 6 carbon atoms and optionally having a substituent selected from an alkoxy group having 1 to 6 carbon atoms, a cycloalkyl group having 3 to 7 carbon atoms, a saturated heterocyclic group, and an unsaturated heterocyclic group is preferred. More specifically, a methyl group, an ethyl group, a n-propyl group, an isopropyl group, a n-butyl group, an isobutyl group, a sec-butyl group, a tert-butyl group, a cyclopropylmethyl group, a 2-methoxyethyl group, a 2-isopropoxyethyl group, a tetrahydrofuranmethyl group, or a 2-pyridylethyl group is preferred.

In the general formula (I), examples of the "optionally substituted cycloalkyl group having 3 to 7 carbon atoms" represented by $R^7$ or $R^8$ include the cycloalkyl group having 3 to 7 carbon atoms as exemplified above which optionally has the substituent. A cycloalkyl group having 3 to 7 carbon atoms and optionally having a substituent selected from a hydroxyl group, an amino group, an aminoacyloxy group, and an unsaturated heterocyclic acyloxy group is preferred. More specifically, a 4-hydroxycyclohexyl group, a cycloheptyl group, a 4-(aminoacetoxy)cyclohexyl group, a 4-(2-aminopropionyloxy)cyclohexyl group, a 4-(2-amino-4-methylpentanoyloxy)cyclohexyl group, or a 4-(morpholinoacetoxy)cyclohexyl group is preferred.

In the general formula (I), examples of the "optionally substituted aromatic hydrocarbon group" represented by $R^7$ or $R^8$ include the aromatic hydrocarbon group having 6 to 14 carbon atoms as exemplified above which optionally has the substituent.

In the general formula (I), examples of the "optionally substituted saturated heterocyclic group" represented by $R^7$ or $R^8$ include the saturated heterocyclic group as exemplified above which optionally has the substituent. A saturated heterocyclic group optionally having an alkyl group having 1 to 6 carbon atoms is preferred. More specifically, for example, a 1-methylpiperidin-4-yl group is preferred.

In the general formula (I), examples of the "optionally substituted unsaturated heterocyclic group" represented by $R^7$ or $R^8$ include the unsaturated heterocyclic group as exemplified above which optionally has the substituent.

In the general formula (I), the "saturated heterocyclic group" which may be formed together by $R^7$ and $R^8$ together with the nitrogen atom bonded thereto refers to a monocyclic or bicyclic saturated heterocyclic group having, preferably, 1 to 4 atoms selected from an oxygen atom, a nitrogen atom, and a sulfur atom, and refers to, for example, a pyrrolidinyl group, a piperidinyl group, a piperazinyl group, a hexamethyleneimino group, a morpholino group, a thiomorpholino group, a homopiperazinyl group, a tetrahydrofuranyl group, or a tetrahydropyranyl group.

In the general formula (I), the combination of $R^7$ and $R^8$ is preferably a hydrogen atom as $R^7$ combined with a hydrogen atom, an optionally substituted alkyl group having 1 to 6 carbon atoms, an optionally substituted cycloalkyl group having 3 to 7 carbon atoms, or an optionally substituted monocyclic or bicyclic saturated heterocyclic group having 1 to 4 heteroatoms selected from N, S, and O as $R^8$, more preferably a hydrogen atom as $R^7$ combined with a hydrogen atom; an alkyl group having 1 to 6 carbon atoms and optionally having a substituent selected from an alkoxy group having 1 to 6 carbon atoms, a cycloalkyl group having 3 to 7 carbon atoms, a saturated heterocyclic group, and an unsaturated heterocyclic group; a cycloalkyl group having 3 to 7 carbon atoms and optionally having a substituent selected from a hydroxyl group, an amino group, an aminoacyloxy group and a saturated heterocyclic acyloxy group; or a monocyclic or bicyclic saturated heterocyclic group having 1 to 4 heteroatoms selected from N, S, and O and optionally having an alkyl group having 1 to 6 carbon atoms as $R^8$, further preferably a hydrogen atom as $R^7$ combined with a hydrogen atom; an alkyl group having 1 to 6 carbon atoms and optionally having a substituent selected from an alkoxy group having 1 to 6 carbon atoms, a cycloalkyl group having 3 to 7 carbon atoms, a saturated heterocyclic group, and an unsaturated heterocyclic group; or a cycloalkyl group having 3 to 7 carbon atoms and optionally having a substituent selected from a hydroxyl group, an amino group, an aminoacyloxy group, and a saturated heterocyclic acyloxy group as $R^8$.

In the general formula (I), examples of the "optionally substituted cycloalkyl group having 3 to 7 carbon atoms" represented by $R^9$ include the cycloalkyl group having 3 to 7 carbon atoms as exemplified above which optionally has the substituent.

In the general formula (I), examples of the "aromatic hydrocarbon group" in the "optionally substituted aromatic hydrocarbon group" represented by $R^9$ include the aromatic hydrocarbon group having 6 to 14 carbon atoms as exemplified above which optionally has the substituent.

$R^9$ is preferably an optionally substituted cycloalkyl group having 3 to 7 carbon atoms, or an optionally substituted aromatic hydrocarbon group having 6 to 14 carbon atoms.

The compound of the present invention is preferably a compound represented by the general formula (I) wherein $X^2$ is C—$R^2$, at least one of $X^1$, $X^3$, and $X^4$ is N or N-oxide and each of the rest of $X^1$, $X^3$, and $X^4$ is CH, $Y^4$ is C—$R^4$ or N and each of $Y^1$ to $Y^3$ is CH, or each of $Y^2$ to $Y^4$ is CH and $Y^1$ is C—R⁴, R¹ is an optionally substituted monocyclic or bicyclic unsaturated heterocyclic group having 1 to 4 heteroatoms selected from N, S, and O, R² is a hydrogen atom; an alkyl group having 1 to 6 carbon atoms and optionally having a substituent selected from a halogen atom and a saturated heterocyclic group; or a cycloalkyl group having 3 to 7 carbon atoms, R³ is a cyano group or —CO—R⁵ wherein R⁵ is an amino group or an alkylamino group having 1 to 6 carbon atoms and optionally having an alkylamino group having 1 to 6 carbon atoms (the alkyl moiety is optionally substituted by a hydroxyl group), and R⁴ is a hydrogen atom, a halogen atom, an alkyl group having 1 to 6 carbon atoms, an alkoxy group having 1 to 6 carbon atoms, or —N(R⁷)(R⁸) wherein R⁷ is a hydrogen atom, and R⁸ is a hydrogen atom; an alkyl group having 1 to 6 carbon atoms and optionally having a substituent selected from an alkoxy group having 1 to 6 carbon atoms, a cycloalkyl group having 3 to 7 carbon atoms, a saturated heterocyclic group, and an unsaturated heterocyclic group; a cycloalkyl group having 3 to 7 carbon atoms and optionally having a substituent selected from a hydroxyl group, an amino group, an aminoacyloxy group, and a saturated heterocyclic acyloxy group; or a monocyclic or bicyclic saturated heterocyclic group having 1 to 4 heteroatoms selected from N, S, and O and optionally having an alkyl group having 1 to 6 carbon atoms, more preferably a compound represented by the general formula (I) wherein X² is C—R², X⁴ is CH, at least one of X¹ and X³ is N or N-oxide and the other of X¹ and X³ is CH, Y⁴ is C—R⁴ or N and each of Y¹ to Y³ is CH, or each of Y² to Y⁴ is CH and Y¹ is C—R⁴, R¹ is an optionally substituted monocyclic or bicyclic unsaturated heterocyclic group having 1 to 4 heteroatoms selected from N, S, and O, R² is a hydrogen atom; an alkyl group having 1 to 6 carbon atoms and optionally having a halogen atom; or a cycloalkyl group having 3 to 7 carbon atoms, R³ is —CO—R⁵ wherein R⁵ is an amino group, and R⁴ is a halogen atom, an alkyl group having 1 to 6 carbon atoms, or —N(R⁷)(R⁸) wherein R⁷ is a hydrogen atom, and R⁸ is a hydrogen atom; an alkyl group having 1 to 6 carbon atoms and optionally having a substituent selected from an alkoxy group having 1 to 6 carbon atoms, a cycloalkyl group having 3 to 7 carbon atoms, a saturated heterocyclic group, and an unsaturated heterocyclic group; or a cycloalkyl group having 3 to 7 carbon atoms and optionally having a substituent selected from a hydroxyl group, an amino group, an aminoacyloxy group, and a saturated heterocyclic acyloxy group, particularly preferably a compound represented by the general formula (I) wherein X² is C—R², X⁴ is CH, at least one of X¹ and X³ is N or N-oxide and the other of X¹ and X³ is CH, Y⁴ is C—R⁴ or N and each of Y¹ to Y³ is CH, or each of Y² to Y⁴ is CH and Y¹ is C—R⁴, R¹ is a monocyclic 5- to 6-membered unsaturated heterocyclic group having 1 to 3 heteroatoms selected from N, S, and O and optionally having a substituent selected from: an alkyl group having 1 to 6 carbon atoms; an alkylamino group having 1 to 6 carbon atoms; an acylamino group having 1 to 6 carbon atoms and optionally having a hydroxyl group; and an unsaturated heterocyclic group optionally having a substituent selected from an alkyl group having 1 to 6 carbon atoms and a halogenoalkyl group having 1 to 6 carbon atoms, or a bicyclic 9- to 10-membered unsaturated heterocyclic group having 1 to 3 heteroatoms selected from N, S, and O and optionally having a substituent selected from an alkyl group having 1 to 6 carbon atoms and an acyl group having 1 to 6 carbon atoms, R² is a hydrogen atom; an alkyl group having 1 to 6 carbon atoms and optionally having a halogen atom; or a cycloalkyl group having 3 to 7 carbon atoms, R³ is —CO—R⁵ wherein R⁵ is an amino group, and R⁴ is a halogen atom, an alkyl group having 1 to 6 carbon atoms, or —N(R⁷)(R⁸) wherein R⁷ is a hydrogen atom, and R⁸ is a hydrogen atom; an alkyl group having 1 to 6 carbon atoms and optionally having a substituent selected from an alkoxy group having 1 to 6 carbon atoms, a cycloalkyl group having 3 to 7 carbon atoms, a saturated heterocyclic group, and an unsaturated heterocyclic group; or a cycloalkyl group having 3 to 7 carbon atoms and optionally having a substituent selected from a hydroxyl group, an amino group, an aminoacyloxy group, and a saturated heterocyclic acyloxy group.

The compound of the present invention can be produced according to, for example, the following reaction scheme:

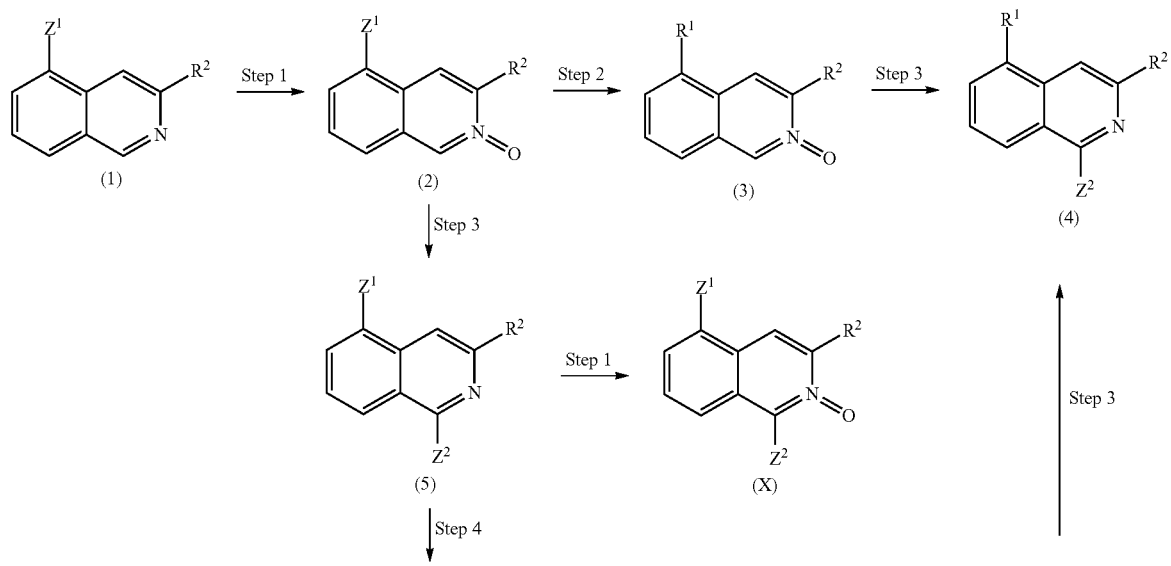

Reaction scheme 1

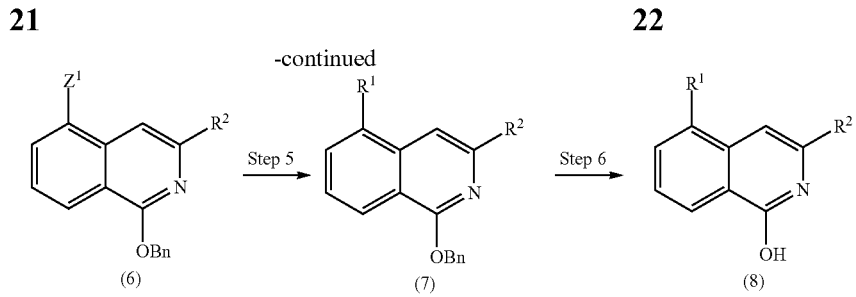

In the reaction scheme 1, $Z^1$ and $Z^2$ each represent a halogen atom, and $R^1$ and $R^2$ are as defined above.

<Step 1>

This step involves reacting an easily available compound represented by the general formula (1) or (5) with an oxidizing agent to produce an isoquinoline oxide compound represented by the general formula (2) or (X). Examples of the oxidizing agent include hydrogen peroxide and meta-chloroperbenzoic acid. The oxidizing agent is preferably meta-chloroperbenzoic acid and is preferably used at 1 to 5 equivalents. The reaction temperature is preferably 0° C. to the boiling point of a solvent. The reaction time is preferably 30 minutes to 50 hours. A halogen solvent (e.g., chloroform and dichloromethane), a hydrocarbon solvent (e.g., hexane, heptane, and toluene), or an ether solvent (e.g., ethylene glycol dimethyl ether and tetrahydrofuran), or a mixed solvent thereof can be used as a reaction solvent.

<Step 2>

This step involves introducing $R^1$ to the compound represented by the general formula (2) by a Suzuki coupling method based on reaction with a boronic acid and a halogen compound or a coupling method using an azole to produce an isoquinoline compound represented by the general formula (3).

The Suzuki coupling method can be performed according to the method described in Chemical Review, 1995, 95, 2457-2483. A palladium complex such as tetrakis(triphenylphosphine)palladium ($Pd(PPh_3)_4$), [1-1'-bis(diphenylphosphino)ferrocene]dichloropalladium ($PdCl_2dppf$), or tris(dibenzylideneacetone)dipalladium ($Pd_2dba_3$) can be used in the reaction. Alternatively, combinations of palladium with various phosphine ligands may be used. The boronic acid or boronic acid ester corresponding to $R^1$ can be synthesized by a usual method known in the art.

The coupling method using an azole can be carried out at a reaction temperature of room temperature to the boiling point of a solvent using 1 to 10 equivalents of the azole in the presence of a base. Examples of the base that can be used include sodium carbonate, potassium carbonate, cesium carbonate, tripotassium phosphate, and sodium hydride. Examples of the azole that can be used include imidazole, pyrazole, triazole, thiazole, and oxazole. The reaction time can be 30 minutes to 50 hours. Alternatively, the reaction may be performed by the addition of a metal such as palladium or copper.

The solvent used is not particularly limited as long as the solvent is inert to this reaction. For example, an ether solvent (e.g., tetrahydrofuran, 1,2-dimethoxyethane, and dioxane) or an aprotic highly polar solvent (e.g., dimethylformamide, dimethylacetamide, and dimethyl sulfoxide), or a mixed solvent thereof can be used. In the case of using an easily available halogen compound corresponding to $R^1$, $Z^1$ in the compound represented by the general formula (2) is converted to dihydroxyboron or dialkoxyboron. Then, the isoquinoline compound represented by the general formula (3) can be produced by the Suzuki coupling method or the coupling method using an azole in the same way as above.

<Step 3>

This step involves introducing $Z^2$ to the compound represented by the general formula (2), (3), or (8) through reaction with a halogenating agent to produce an isoquinoline compound represented by the general formula (4) or (5).

Examples of the halogenating agent include phosphorus oxychloride, phosphorus oxybromide, thionyl chloride, and tetrabutyl ammonium bromide. The halogenating agent is preferably phosphorus oxychloride and is preferably used at 1 to 5 equivalents. The reaction temperature is preferably 0° C. to the boiling point of a solvent. The reaction time is preferably 30 minutes to 50 hours. A halogen solvent (e.g., chloroform and dichloromethane), a hydrocarbon solvent (e.g., hexane, heptane, and toluene), or an ether solvent (e.g., ethylene glycol dimethyl ether and tetrahydrofuran), or a mixed solvent thereof can be used as a reaction solvent.

<Step 4>

This step involves introducing an alkoxy group to $Z^2$ in the compound represented by the general formula (5) through reaction with benzyl alcohol to produce an isoquinoline compound represented by the general formula (6).

One or more of potassium hydroxide, sodium hydroxide, potassium carbonate, and sodium carbonate can be used as a base and is preferably used at 1 to 5 equivalents. TDA or PEG can be used as an additive and is preferably used at 0.1 to 1 equivalents. The reaction temperature is preferably 0° C. to the boiling point of a solvent. The reaction time is preferably 30 minutes to 50 hours. A hydrocarbon solvent (e.g., hexane, heptane, and toluene) or an ether solvent (e.g., ethylene glycol dimethyl ether and tetrahydrofuran), or a mixed solvent thereof can be used as a reaction solvent.

<Step 5>

This step involves introducing $R^1$ to the compound represented by the general formula (6) by a Suzuki coupling method based on reaction with a boronic acid and a halogen compound or a coupling method using an azole to produce a heterocyclic compound represented by the general formula (7).

This step can be carried out in the same way as in <Step 2>.

<Step 6>

This step involves hydrogenating the compound represented by the general formula (7) and deprotecting the benzyl group to produce a heterocyclic compound represented by the general formula (8).

Examples of the hydrogen source include hydrogen and cyclohexene. The hydrogen source is preferably cyclohexene and is preferably used at 1 to 100 equivalents. The reaction temperature is preferably 0° C. to the boiling point of a solvent. The reaction time is preferably 30 minutes to 50 hours. An alcohol solvent (e.g., ethanol and methanol) can be used as a reaction solvent.

Reaction scheme 2

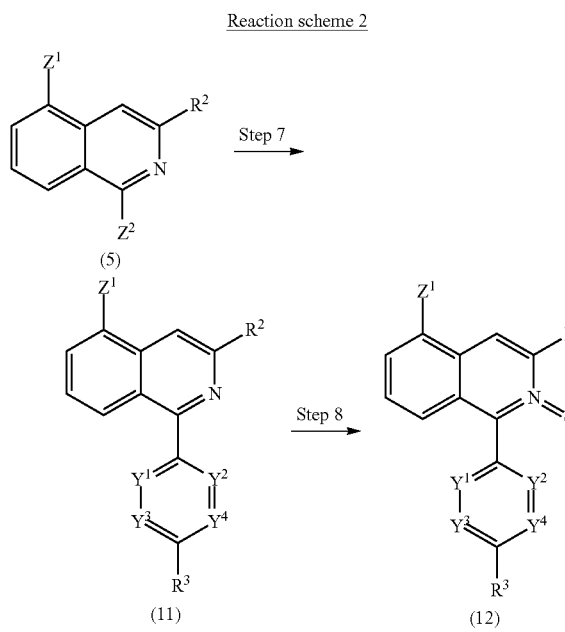

In the reaction scheme 2, $Z^1$, $Z^2$, $R^2$, $R^3$, $Y^1$, $Y^2$, $Y^3$, and $Y^4$ are as defined above.
<Step 7>

This step involves subjecting the compound represented by the general formula (5) to a Suzuki coupling method based on reaction with a boronic acid and a halogen compound or a coupling method using an azole to produce an isoquinoline compound represented by the general formula (11).

This step can be carried out in the same way as in <Step 2>.
<Step 8>

This step involves producing an isoquinoline compound represented by the general formula (12) through oxidation reaction from the compound represented by the general formula (11).

This step can be carried out in the same way as in <Step 1>.

Reaction scheme 3

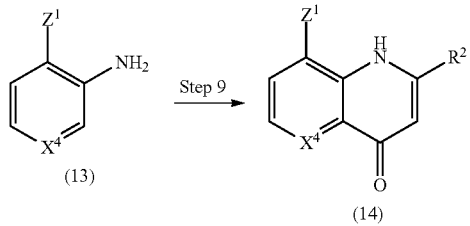

In the reaction scheme 3, $Z^1$, $R^2$, and $X^4$ are as defined above.
<Step 9>

This step involves reacting the compound represented by the general formula (13) with beta keto ester, beta formyl ester, or alkoxymethylene-substituted Meldrum's acid for cyclization to produce a heterocyclic compound represented by the general formula (14).

Examples of an acid promoting the cyclization include sulfuric acid, hydrochloric acid, polyphosphoric acid, and nitric acid. The acid is preferably polyphosphoric acid and is preferably used at 1 to 1000 equivalents. The reaction temperature is preferably 0° C. to 250° C. The reaction time is preferably 30 minutes to 50 hours. A halogen solvent (e.g., chloroform and dichloromethane), a hydrocarbon solvent (e.g., hexane, heptane, and toluene), or an ether solvent (e.g., ethylene glycol dimethyl ether, tetrahydrofuran, and Dowtherm), or a mixed solvent thereof can be used as a reaction solvent.

Reaction scheme 4

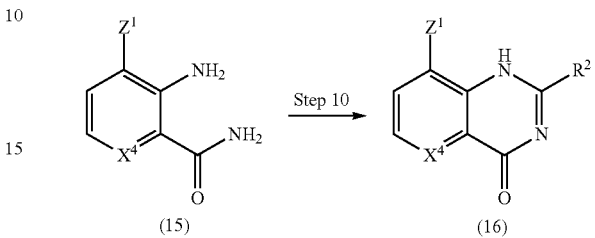

In the reaction scheme 4, $Z^1$, $R^2$, and $X^4$ are as defined above.
<Step 10>

This step involves reacting the compound represented by the general formula (15) with corresponding ester, orthoester, or aldehyde for cyclization to produce a heterocyclic compound represented by the general formula (16). In the case of using ester, a base is used for promoting the reaction. Examples of the base include sodium hydroxide, sodium ethylate, and sodium methylate. The base is preferably sodium ethylate and is preferably used at 0.1 to 100 equivalents.

In the case of using orthoester, an acid is used for promoting the reaction. Examples of the acid include hydrochloric acid, sulfuric acid, tosylic acid, and mesylic acid. The acid is preferably tosylic acid and is preferably used at 0.1 to 100 equivalents.

In the case of using aldehyde, an inorganic salt is used for promoting the reaction. Examples of the inorganic salt include iron chloride, iron bromide, and iron iodide. The inorganic salt is preferably iron chloride and is preferably used at 0.1 to 100 equivalents.

The reaction temperature is preferably 0° C. to 150° C. The reaction time is preferably 30 minutes to 50 hours. A highly polar solvent (e.g., ethanol, methanol, water, DMF, NMP, and DMSO) can be used as a reaction solvent.

Reaction scheme 5

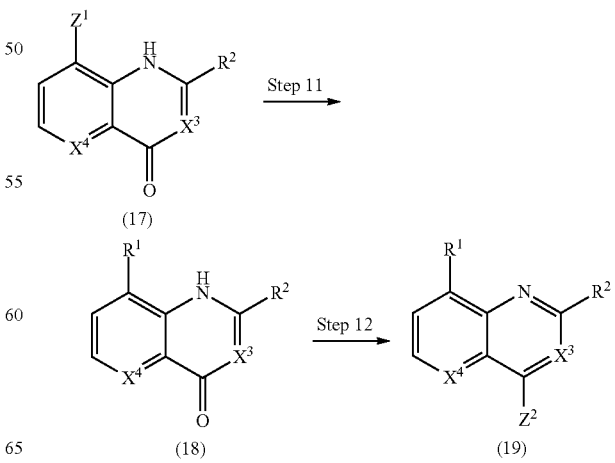

In the reaction scheme 5, $Z^1, Z^2, R^1, R^2, R^3, X^3, X^4, Y^1, Y^2, Y^3$, and $Y^4$ are as defined above.

<Step 11>

This step involves subjecting the compound represented by the general formula (17) to a Suzuki coupling method based on reaction with a boronic acid and a halogen compound or a coupling method using an azole to produce a heterocyclic compound represented by the general formula (18).

This step can be carried out in the same way as in <Step 2>.

<Step 12>

This step involves introducing $Z^2$ to the compound represented by the general formula (18) through reaction with a halogenating agent to produce a heterocyclic compound represented by the general formula (19).

This step can be carried out in the same way as in <Step 3>.

Reaction scheme 6

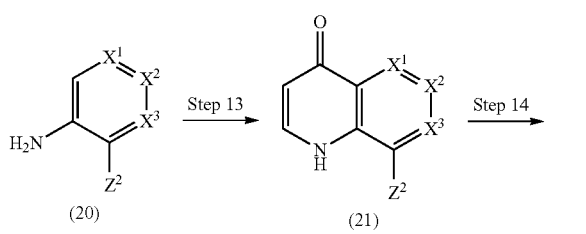

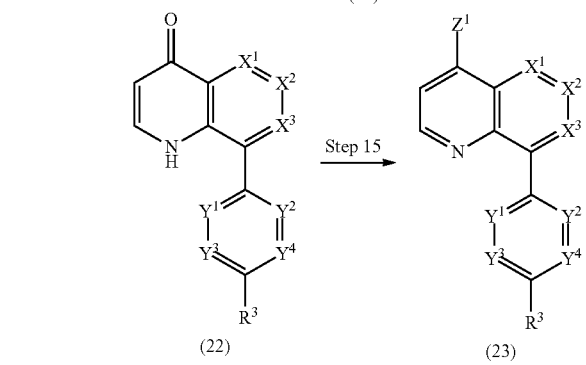

In the reaction scheme 6, $Z^1, Z^2, R^2, R^3, X^1, X^2, X^3, Y^1, Y^2, Y^3$, and $Y^4$ are as defined above.

<Step 13>

This step involves reacting the compound represented by the general formula (20) with alkoxymethylene-substituted Meldrum's acid for cyclization to produce a heterocyclic compound represented by the general formula (21).

This step can be carried out in the same way as in <Step 9>.

<Step 14>

This step involves reacting $Z^2$ in the compound represented by the general formula (21) with a boronic acid by a Suzuki coupling method to produce a compound represented by the general formula (22).

This step can be carried out in the same way as in <Step 2> using the Suzuki coupling method.

<Step 15>

This step involves introducing $Z^2$ to the compound represented by the general formula (22) through reaction with a halogenating agent to produce a heterocyclic compound represented by the general formula (23).

This step can be carried out in the same way as in <Step 3>.

Reaction scheme 7

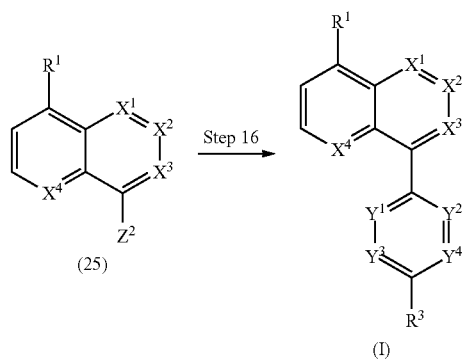

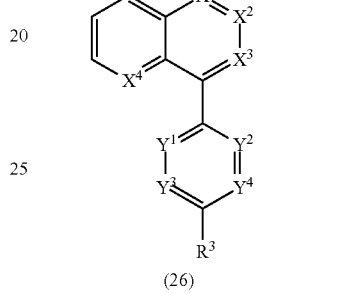

In the reaction scheme 7, $Z^1, Z^2, R^1, R^2, R^3, X^1, X^2, X^3, X^4, Y^1, Y^2, Y^3$, and $Y^4$ are as defined above.

<Step 16>

This step involves reacting $Z^2$ in the compound represented by the general formula (25) with a boronic acid by a Suzuki coupling method to produce the compound represented by the general formula (I).

This step can be carried out in the same way as in <Step 2> using the Suzuki coupling method.

<Step 17>

This step involves subjecting the compound represented by the general formula (26) to a Suzuki coupling method based on reaction with a boronic acid and a halogen compound or a coupling method using an azole to produce the compound represented by the general formula (I).

This step can be carried out in the same way as in <Step 2>.

The heterocyclic group represented by $R^1$, the alkyl group represented by $R^2$, the substituent (such as nitrile, ester, or nitro group) represented by $R^3$, or $R^4$ in any of $Y^1, Y^2, Y^3$, and $Y^4$ in the general formula (I) can be subjected to reaction by a usual method known in the art at any stage to produce the desired compound.

For example, in the case of $R^1$ containing a nitrogen atom, N-oxide can be synthesized through oxidation reaction. $R^2$ can be halogenated at the benzyl position and subjected to substitution reaction with a nucleophilic agent. In the case of a nitrile group as $R^3$, a carboxamide compound can be produced by a usual hydrolysis method known in the art. Alternatively, in the case of an ester group as $R^3$, a carboxylic acid compound can be produced by hydrolysis and can be further reacted with amine to produce the desired amide compound. In the case of a nitro group as $R^3$, an amino compound can be produced by catalytic reduction etc. and can be further reacted with carboxylic acid, isocyanate, etc. to produce the desired amide compound, urea compound, etc.

For example, in the case of a halogen atom as R⁴, the desired amine compound or thioether compound can be produced.

In <Step 1> to <Step 17> above, if a reactive substituent that causes reaction other than the intended one is present in substituent introduction or functional group conversion, a protective group may be introduced, if necessary, to the reactive substituent in advance by means known per se in the art and removed, after the intended reaction, by means known in the art to produce each compound. After the completion of reaction, the compound of interest obtained in each of these steps is recovered from the reaction mixture according to a routine method. For example, the reaction mixture is appropriately neutralized, and insoluble matter, if present, is removed by filtration. Then, the reaction solution is subjected to extraction with a water-immiscible organic solvent such as toluene, ethyl acetate, or chloroform. After washing with water etc., the organic layer containing the compound of interest is concentrated under reduced pressure to distill off the solvent. In this way, the compound of interest is obtained. The obtained compound of interest can be separated and purified, if necessary, by a routine method, for example, recrystallization, reprecipitation, or any of other methods routinely used for the separation and purification of usual organic compounds (e.g., column adsorption chromatography using a carrier such as silica gel, alumina, or magnesium-silica gel Florisil; partition column chromatography or ion-exchange chromatography using a carrier such as Sephadex LH-20 (manufactured by GE Healthcare Japan Corp. (formerly Pharmacia)), Amberlite XAD-11 (manufactured by Rohm and Haas Company), or Diaion HP-20 (manufactured by Mitsubishi Chemical Corp.); or normal-phase or reverse-phase column chromatography using silica gel or alkylated silica gel; preferably, silica gel column chromatography). Compound (I) obtained in a free form can be converted to its pharmacologically acceptable salt by a method known per se in the art or a method equivalent thereto. Alternatively, compound (I) obtained in a salt form can be converted to a free form or any of other salts of interest by a method known per se in the art or a method equivalent thereto.

Compound (I) may have isomers such as optical isomers, stereoisomers, positional isomers, and rotational isomers. Any one of these isomers and mixtures thereof are also encompassed by compound (I). For example, compound (I) may have optical isomers. In such a case, an optical isomer separated from a racemate is also encompassed by compound (I). These isomers can be obtained each individually as a single compound by synthesis and separation approaches (concentration, solvent extraction, column chromatography, recrystallization, etc.) known per se in the art.

Compound (I) may be in a crystalline form. Compounds having single crystal forms and crystal polymorphs are also encompassed by compound (I). The crystals can be produced by crystallization using a crystallization method known per se in the art. Compound (I) may be in a solvate (e.g., hydrate) or non-solvate form. Both of them are encompassed by compound (I).

Compounds labeled with isotopes (e.g., ³H, ¹⁴C, ³⁵S, and ¹²⁵I) are also encompassed by compound (I).

A prodrug of compound (I) or the salt thereof (hereinafter, abbreviated to compound (I)) refers to a compound which is converted to the compound (I) due to a reaction induced by, for example, an enzyme, gastric acid under physiological conditions in vivo, i.e., a compound which is converted to the compound (I) through, for example, enzymatic oxidation, reduction, hydrolysis or a compound which is converted to the compound (I) through hydrolysis etc. induced by gastric acid etc. Alternatively, the prodrug of compound (I) may be a compound which is converted to the compound (I) under physiological conditions as described in pages 163 to 198 of Vol. 7 Molecular Design in "Iyakuhin No Kaihatsu (Pharmaceutical Development in English)" published by Hirokawa Shoten Co., Ltd. (1990).

The compound (I) of the present invention has excellent HSP90 inhibitory activity and excellent cancer cell growth inhibitory activity and is useful as a pharmaceutical agent such as an anticancer agent. Also, the compound (I) of the present invention is highly soluble in water and orally administrable and as such, is useful as an orally administrable pharmaceutical agent such as an orally administrable anticancer agent. Examples of malignant tumors to which compound (I) can be applied include head and neck cancer, esophageal cancer, gastric cancer, colon cancer, rectal cancer, liver cancer, cystic duct cancer, biliary cancer, pancreatic cancer, lung cancer, breast cancer, ovary cancer, uterine cervix cancer, uterine body cancer, renal cancer, bladder cancer, prostatic cancer, orchioncus, bone and soft-tissue sarcoma, leukemia, malignant lymphoma, multiple sclerosis, skin cancer, brain tumor, and mesothelioma.

In order to use the compound (I) of the present invention as a pharmaceutical agent, compound (I) is mixed, if necessary, with a pharmaceutically acceptable carrier to prepare a pharmaceutical composition. Various dosage forms can be adopted according to preventive or therapeutic purposes. The forms may be any of, for example, oral formulations, injections, suppositories, ointments, and patches. Preferably, an oral formulation is adopted. These dosage forms can each be produced by a routine formulation method known by those skilled in the art.

Various organic or inorganic carrier materials routinely used as pharmaceutical materials are used as the pharmaceutically acceptable carrier. Solid preparations are formulated using, for example, an excipient, a binder, a disintegrant, a lubricant, a coloring agent. Liquid preparations are formulated using, for example, a solvent, a solubilizer, a suspending agent, a tonicity agent, a buffer, a soothing agent. In addition, pharmaceutical additives such as an antiseptic, an antioxidant, a coloring agent, a sweetening agent, and a stabilizer may be used, if necessary.

In the case of preparing oral solid preparations, the compound (I) of the present invention is supplemented with an excipient or with, if necessary, for example, an excipient, a binder, a disintegrant, a lubricant, a coloring agent, a corrigent. Then, tablets, coated tablets, granules, powders, capsules, etc. can be produced by a routine method.

In the case of preparing injections, the compound (I) of the present invention is supplemented with, for example, a pH adjuster, a buffer, a stabilizer, a tonicity agent, a local anesthetic. Hypodermic, intramuscular, and intravenous injections can be produced by a routine method.

The amount of the compound (I) of the present invention to be contained in each of the dosage units described above varies depending on the symptoms of a recipient patient or the dosage form, etc. In general, approximately 0.05 to 1000 mg for oral formulations, approximately 0.01 to 500 mg for injections, or approximately 1 to 1000 mg for suppositories is desirable per unit dosage.

The daily dose of a drug having any of the dosage forms differs depending on the symptoms, body weight, age, sex, etc. of a patient and cannot be normalized. The daily dose in adult (body weight: 50 kg) can be usually approximately 0.05 to 5000 mg, preferably 0.1 to 1000 mg, which is preferably administered once a day or at approximately two or three divided doses per day.

EXAMPLES

Hereinafter, the present invention will be described specifically with reference to Examples and Test Examples. However, these examples are provided for illustrative purposes and do not limit the scope of the present invention.

$^1$H-NMR spectra were measured using tetramethylsilane (TMS) as an internal standard. δ values for chemical shifts were indicated by ppm. The chemical shifts were indicated with the number of protons, an absorption pattern, and a coupling constant (J value) within parentheses.

The following symbols related to absorption patterns are used: s=singlet, d=doublet, t=triplet, q=quartet, dd=double doublet, ddd=double double doublet, dt=double triplet, m=multiplet, br=broad, and br s=broad singlet.

Also, the following symbols related to the structural formulas of compounds may be used: Me=methyl, Et=ethyl, tBu=tert-butyl, Ph=phenyl, Ac=acetyl, Boc=tert-butoxycarbonyl, TFA=trifluoroacetic acid, MsOH=methanesulfonic acid, DMF=dimethylformamide, THF=tetrahydrofuran, NMP=N-methylpyrrolidinone, and CDI=carbonyldiimidazole.

Example 1

2-(Ethylamino)-4-(5-(4-(1-methyl-1H-pyrazol-4-yl)-1H-imidazol-1-yl)isoquinolin-1-yl)benzamide (1)

Example 1(1)

5-Bromoisoquinoline-2-oxide (1a)

Aqueous meta-chloroperbenzoic acid (65%, 29 g) was added to a solution of 5-bromoisoquinoline (20.7 g) in chloroform (250 ml), and the mixture was stirred at room temperature for 1 hour. The reaction solution was neutralized with an aqueous sodium hydroxide solution with cooling in an ice bath and partitioned into organic and aqueous layers. The organic layer was washed with brine. The organic layer thus washed was dried over anhydrous sodium sulfate. Then, the solvent was distilled off, and small amounts of chloroform and diethyl ether were added to the residue. The deposit was filtrated to obtain compound (1a) (11.8 g, 50%).

Example 1(2)

1-Chloro-5-bromoisoquinoline (1b)

Phosphorus oxychloride (5 ml) was added to a suspension of compound (1a) (7.83 g) in chloroform (120 ml), and the mixture was stirred overnight at 50° C. The solvent was distilled off under reduced pressure, and chloroform was added to the residue. The reaction solution was neutralized with an aqueous sodium hydroxide solution with cooling in an ice bath and partitioned into organic and aqueous layers. The organic layer was washed with brine. The organic layer thus washed was dried over anhydrous sodium sulfate. Then, the solvent was distilled off, and small amounts of chloroform and diethyl ether were added to the residue. The deposit was filtrated to obtain compound (1b) (5.83 g, 65%) as a white solid.

Example 1(3)

1-(Benzyloxy)-5-bromoisoquinoline (1c)

A suspension of compound (1b) (0.242 g), benzyl alcohol (0.162 g), potassium hydroxide (0.224 g), potassium carbonate (0.138 g), and tris(2-(2-methoxyethoxy)ethyl)amine (0.032 ml) in toluene (6 ml) was stirred at 120° C. for 1 hour. The reaction solution was partitioned between ethyl acetate and water. The organic layer was washed with brine and then dried over anhydrous sodium sulfate. The solvent was distilled off, and the residue was then purified by neutral silica gel column chromatography (n-hexane/ethyl acetate) to obtain compound (1c) (0.621 g, 99%) as a pale yellow solid.

Example 1(4)

1-Chloro-5-(4-(1-methyl-1H-pyrazol-4-yl)-1H-imidazol-1-yl)isoquinoline (1d)

Compound (1c) (3.03 g), 4-(1H-imidazol-4-yl)-1-methyl-1H-pyrazole hydrochloride (1.96 g), 8-quinolinol (0.280 g), copper(I) oxide (0.280 g), PEG (Mn=3400) (1.90 g), and cesium carbonate (12.5 g) were suspended in DMSO (20 ml). The suspension was purged with nitrogen, then sealed in the tube, and stirred overnight at 125° C. After cooling, the reaction solution was partitioned between ethyl acetate and water. The organic layer was washed with brine and then dried over anhydrous sodium sulfate. The solvent was distilled off, and the residue was then purified by neutral silica gel column chromatography (chloroform/methanol) to obtain a white solid (2.60 g). The obtained white solid (2.60 g) and carbon-supported palladium hydroxide (2.60 g) were suspended in cyclohexene (68 ml) and ethanol (34 ml), and the suspension was stirred at 80° C. for 4 hours in a nitrogen atmosphere. After cooling, a mixed solution of chloroform and methanol (5:1) was added thereto, and insoluble matter was filtered off using celite. The solvent in the filtrate was distilled off. Then, chloroform was added to the residue, and the deposit was filtrated to obtain a white solid (1.47 g). Phosphorus oxychloride (7.6 ml) was added to the obtained white solid (1.11 g), and the mixture was heated to reflux for 2 hours. The solvent was distilled off under reduced pressure, and chloroform was added to the residue. The reaction solution was neutralized with an aqueous sodium hydroxide solution with cooling in an ice bath and partitioned into organic and aqueous layers. The organic layer was washed with brine. The organic layer thus washed was dried over anhydrous sodium sulfate. Then, the solvent was distilled off, and small amounts of chloroform and diethyl ether were added to the residue. The deposit was filtrated to obtain compound (1d) (0.929 g, yield based on 3 steps: 33%) as a white solid.

Example 1(5)

2-(Ethylamino)-4-(5-(4-(1-methyl-1H-pyrazol-4-yl)-1H-imidazol-1-yl)isoquinolin-1-yl)benzamide (1)

Pd(PPh$_3$)$_4$ (0.012 g) was added to a solution of compound (1d) (0.062 g), 4-cyano-3-(ethylamino)phenylboronic acid pinacol ester (0.071 g), and an aqueous sodium carbonate solution (2 M, 1.5 mL) in ethylene glycol dimethyl ether (3.0 mL) in a nitrogen atmosphere, and the mixture was stirred at 85° C. for 3 hours. The reaction solution was partitioned between ethyl acetate and water. The organic layer was washed with brine and then dried over anhydrous sodium sulfate. The solvent was distilled off, and the obtained residue was used in the next reaction. An aqueous sodium hydroxide solution (4 M, 0.093 mL) and a 30% aqueous hydrogen peroxide solution (0.045 mL) were added to a solution of the obtained residue in DMSO (3 mL) and ethanol (1.5 mL) at room temperature, and the mixture was stirred for 30 minutes. Water was added to the reaction solution, and the deposit was collected by filtration, then washed with water and ether by sprinkling, and then dried under reduced pressure to obtain compound (1) (0.040 g, yield based on 2 steps: 45%) as a pale yellow solid.

Example 2

4-(5-(5-Aminopyridin-3-yl)isoquinolin-1-yl)-2-(4-hydroxycyclohexylamino)benzamide (2)

Example 2(1)

4-(5-Bromoisoquinolin-1-yl)-2-(4-hydroxycyclohexylamino)benzonitrile (2a)

Pd(PPh$_3$)$_4$ (1.39 g) was added to a solution of compound (1b) (5.83 g), 4-cyano-3-(4-hydroxycyclohexylamino)phenylboronic acid pinacol ester (7.80 g), and an aqueous sodium carbonate solution (2 M, 40 mL) in ethylene glycol dimethyl ether (80 mL) in a nitrogen atmosphere, and the mixture was stirred at 85° C. for 3 hours. The reaction solution was partitioned between ethyl acetate and water. The organic layer was washed with brine and then dried over anhydrous sodium sulfate. The solvent was distilled off, and the residue was purified by neutral silica gel column chromatography (chloroform/methanol) to obtain compound (2a) (14.8 g, yield: 62%) as a white solid.

Example 2(2)

2-(4-Hydroxycyclohexylamino)-4-(5-(4,4,5,5,-tetramethyl-1,3,2-dioxaborolan-2-yl)isoquinolin-1-yl)benzonitrile (2b)

A suspension of compound (2a) (2.56 g), bis(pinacolato)diboron (1.79 g), PdCl$_2$dppf (0.478 g), and potassium acetate (2.3 g) in dioxane (20 mL) was stirred at 85° C. for 3 hours in a nitrogen atmosphere. Chloroform was added to the reaction solution, and insoluble matter was filtered off using celite. The solvent in the filtrate was distilled off, and the obtained residue was purified by neutral silica gel column chromatography (n-hexane/ethyl acetate) to obtain compound (2b) (1.38 g, 50%) as a white solid.

Example 2(3)

4-(5-(5-Aminopyridin-3-yl)isoquinolin-1-yl)-2-(4-hydroxycyclohexylamino)benzamide (2)

Pd(PPh$_3$)$_4$ (0.013 g) was added to a solution of compound (2b) (0.102 g), 3-amino-5-bromopyridine (0.042 g), and an aqueous sodium carbonate solution (2 M, 1.5 mL) in ethylene glycol dimethyl ether (3 mL) in a nitrogen atmosphere, and the mixture was stirred at 85° C. for 3 hours. The reaction solution was partitioned between ethyl acetate and water. The organic layer was washed with brine and then dried over anhydrous sodium sulfate. The solvent was distilled off. An aqueous sodium hydroxide solution (4 M, 0.093 mL) and a 300 aqueous hydrogen peroxide solution (0.045 mL) were added to a solution of the obtained residue in DMSO (3 mL) and ethanol (1.5 mL) at room temperature, and the mixture was stirred for 30 minutes. Water was added to the reaction solution, and the deposit was collected by filtration, then washed with water and ether by sprinkling, and then dried under reduced pressure to obtain compound (2) (0.045 g, yield based on 2 steps: 45%) as a pale yellow solid.

Example 3

2-(Ethylamino)-4-(8-(4-(1-methyl-1H-pyrazol-4-yl)-1H-imidazol-1-yl)-2-(trifluoromethyl)quinolin-4-yl)benzamide (3)

Example 3(1)

8-Iodo-2-(trifluoromethyl)quinolin-4(1H)-one (3a)

A mixture of 2-iodoaniline (25.0 g), ethyl 4,4,4-trifluoro-3-oxobutanoate (20.8 g), and PPA (78.0 g) was stirred at 180° C. for 1 hour. After cooling, the reaction solution was neutralized with an aqueous sodium hydroxide solution, and the deposit was filtered and washed with water. The filtrate was rendered acidic with hydrochloric acid, and the deposit was filtered and washed with water. The filtration residues were dried under reduced pressure to obtain compound (3a) (16.2 g, 42%) as a white solid.

Example 3(2)

4-Chloro-8-(4-(1-methyl-1H-pyrazol-4-yl)-1H-imidazol-1-yl)-2-(trifluoromethyl)quinoline (3b)

Compound (3a) (2.58 g), 4-(1H-imidazol-4-yl)-1-methyl-1H-pyrazole hydrochloride (1.54 g), 8-quinolinol (0.220 g), copper(I) oxide (0.220 g), PEG (Mn=3400) (1.50 g), and cesium carbonate (9.80 g) were suspended in DMSO (16 ml). The suspension was purged with nitrogen, then sealed in the tube, and stirred overnight at 125° C. After cooling, a mixed solution of chloroform and methanol (5:1) was added thereto, and insoluble matter was filtered off using celite. The aqueous layer was rendered acidic with hydrochloric acid, and the deposit was filtered and washed with water. The filtration residue was dried under reduced pressure to obtain a white solid (1.36 g). Phosphorus oxychloride (13 ml) was added to the obtained white solid (1.36 g), and the mixture was heated to reflux for 2 hours. The solvent was distilled off under reduced pressure, and chloroform was added to the residue. The reaction solution was neutralized with an aqueous sodium hydroxide solution with cooling in an ice bath and partitioned into organic and aqueous layers. The organic layer was washed with brine. The organic layer thus washed was dried over anhydrous sodium sulfate. Then, the solvent was distilled off, and the residue was purified by neutral silica gel column chromatography (chloroform/methanol) to obtain compound (3b) (1.08 g, yield based on 2 steps: 38%) as a white solid.

Example 3(3)

2-(Ethylamino)-4-(8-(4-(1-methyl-1H-pyrazol-4-yl)-1H-imidazol-1-yl)-2-(trifluoromethyl)quinolin-4-yl)benzamide (3)

Pd(PPh$_3$)$_4$ (0.011 g) was added to a solution of compound (3b) (0.07 g), 4-cyano-3-(ethylamino)phenylboronic acid pinacol ester (0.065 g), and an aqueous sodium carbonate solution (2 M, 1.5 mL) in ethylene glycol dimethyl ether (3.0 mL) in a nitrogen atmosphere, and the mixture was stirred at 85° C. for 3 hours. The reaction solution was partitioned between ethyl acetate and water. The organic layer was washed with brine and then dried over anhydrous sodium sulfate. The solvent was distilled off, and the obtained residue was used in the next reaction. An aqueous sodium hydroxide solution (4 M, 0.093 mL) and a 30% aqueous hydrogen peroxide solution (0.045 mL) were added to a solution of the obtained residue in DMSO (3 mL) and ethanol (1.5 mL) at room temperature, and the mixture was stirred for 30 minutes. Water was added to the reaction solution, and the deposit was collected by filtration, then washed with water and ether by sprinkling, and then dried under reduced pressure to obtain compound (3) (0.061 g, yield based on 2 steps: 65%) as a pale yellow solid.

Example 4

2-Amino-4-(8-(4-(1-methyl-1H-pyrazol-4-yl)-1H-imidazol-1-yl)-2-(trifluoromethyl)quinazolin-4-yl) benzamide (4)

Example 4(1)

8-Iodo-2-(trifluoromethyl)quinazolin-4(1H)-one (4a)

EDCI hydrochloride (18.4 g) and 1-hydroxybenzotriazole (9.5 g) were added to a solution of 2-amino-3-iodobenzoic acid (16.4 g) synthesized using the method described in Journal of Medicinal Chemistry, 2004, 47 (6), 1448-1464 in DMF (120 mL), and subsequently ammonia water (21.2 ml) was added thereto. The reaction solution was stirred at room temperature for 3 hours. Water was added to the reaction solution, and the deposit was filtrated and dried under reduced pressure to obtain 2-amino-3-iodobenzamide (12.8 g). 60% sodium hydride (2.29 g) was added to a solution of the obtained 2-amino-3-iodobenzamide (5.0 g) in ethanol (95 ml), then ethyl trifluoroacetate (10.8 g) was added thereto, and the mixture was heated to reflux for 15 hours. After cooling, water was added thereto, and the reaction solution was rendered acidic by the addition of 6 N hydrochloric acid. Then, the deposit was filtrated and dried under reduced pressure to obtain compound (4a) (6.4 g, yield based on 2 steps: 77%).

Example 4(2)

4-Chloro-8-(4-(1-methyl-1H-pyrazol-4-yl)-1H-imidazol-1-yl)-2-(trifluoromethyl)quinoline (4b)

Compound (4b) was obtained (yield based on 2 steps: 52%) according to Example 3(2) using compound (4a) instead of compound (3a).

Example 4(3)

2-Amino-4-(8-(4-(1-methyl-1H-pyrazol-4-yl)-1H-imidazol-1-yl)-2-(trifluoromethyl)quinazolin-4-yl) benzamide (4)

Compound (4) was obtained as a pale yellow solid (yield based on 2 steps: 16%) according to Example 1(5) using compound (4b) instead of compound (1d) and 3-amino-4-cyanophenylboronic acid pinacol ester instead of 4-cyano-3-(ethylamino)phenylboronic acid pinacol ester.

Example 5

2-(Tert-butylamino)-4-(2'-(trifluoromethyl)-3,8'-biquinolin-4'-yl)benzamide (5)

Example 5(1)

4'-Chloro-2'-(trifluoromethyl)-3,8'-bisquinoline (5a)

PdCl$_2$dppf (0.458 g) was added to a solution of compound (3a) (2.72 g), 3-quinolineboronic acid (1.66 g), and an aqueous sodium carbonate solution (2 M, 2.7 mL) in ethylene glycol dimethyl ether (5.3 mL) in a nitrogen atmosphere, and the mixture was stirred at 150° C. for 10 minutes under microwave irradiation. The reaction solution was partitioned between ethyl acetate and water. The organic layer was washed with brine and then dried over anhydrous sodium sulfate. The solvent was distilled off. Chloroform was added to the obtained residue, and the deposit was collected by filtration. The filtration residue (2.20 g) was used in the next reaction without being purified. Phosphorus oxychloride (10 ml) was added to the obtained filtration residue (2.20 g), and the mixture was heated to reflux for 2 hours. The solvent was distilled off under reduced pressure, and chloroform was added to the residue. The reaction solution was neutralized with an aqueous sodium hydroxide solution with cooling in an ice bath and partitioned into organic and aqueous layers. The organic layer was washed with brine. The organic layer thus washed was dried over anhydrous sodium sulfate. Then, the solvent was distilled off, and the residue was purified by neutral silica gel column chromatography (n-hexane/ethyl acetate) to obtain compound (5a) (1.76 g, yield based on 2 steps: 61%) as a white solid.

Example 5(2)

2-(Tert-butylamino)-4-(2'-(trifluoromethyl)-3,8'-biquinolin-4'-yl)benzamide (5)

Compound (5) was obtained as a pale yellow solid (yield based on 2 steps: 90%) according to Example 3(3) using compound (5a) instead of compound (3b) and 3-(tert-butylamino)-4-cyanophenylboronic acid pinacol ester instead of 4-cyano-3-(ethylamino)phenylboronic acid pinacol ester.

Example 6

2-(4-Hydroxycyclohexylamino)-4-(5-(quinolin-3-yl) isoquinolin-1-yl)benzamide (6)

3-(1-Chloroisoquinolin-5-yl)quinoline was obtained according to Example 5(1) using compound (1a) instead of compound (3a) and Pd(PPh$_3$)$_4$ instead of PdCl$_2$dppf. Compound (6) was obtained as a white solid (yield based on 4 steps: 57%) according to Example 1(5) using the obtained 3-(1-chloroisoquinolin-5-yl)quinoline instead of compound (1d) and 4-cyano-3-(4-hydroxycyclohexylamino)phenylboronic acid pinacol ester instead of 4-cyano-3-(ethylamino) phenylboronic acid pinacol ester.

Example 7

2-(4-Hydroxycyclohexylamino)-4-(3-methyl-5-(quinolin-3-yl)isoquinolin-1-yl)benzamide (7)

5-Bromo-3-methylisoquinoline-2-oxide was obtained according to Example 1(1) using 5-bromo-3-methylisoquinoline instead of 5-bromoisoquinoline. Compound (7) was obtained as a white solid (yield based on 5 steps: 14%) according to Example 6 using the obtained 5-bromo-3-methylisoquinoline-2-oxide instead of compound (1a).

Example 8

1-(4-Carbamoyl-3-(4-hydroxycyclohexylamino)phenyl)-3-methyl-5-(quinolin-3-yl)isoquinoline-2-oxide (8)

Example 8(1)

5-Bromo-1-chloro-3-methylisoquinoline (8a)

Compound (8a) was obtained as a white solid (yield based on 2 steps: 61%) according to Examples 1(1) and 1(2) using 5-bromo-3-methylisoquinoline instead of 5-bromoisoquinoline.

Example 8(2)

1-(4-Carbamoyl-3-(4-hydroxycyclohexylamino)phenyl)-3-methyl-5-(quinolin-3-yl)isoquinoline-2-oxide (8)

4-(5-Bromo-3-methylisoquinolin-1-yl)-2-(4-hydroxycyclohexylamino)benzonitrile was obtained according to Example 2(1) using compound (8a) instead of compound (1b). 5-Bromo-1-(4-cyano-3-(4-hydroxycyclohexylamino)phenyl)-3-methylisoquinoline-2-oxide was obtained according to Example 1(1) using the obtained 4-(5-bromo-3-methylisoquinolin-1-yl)-2-(4-hydroxycyclohexylamino)benzonitrile instead of 5-bromoisoquinoline. Compound (8) was obtained (yield based on 4 steps: 9%) according to Example 1(5) using the obtained 5-bromo-1-(4-cyano-3-(4-hydroxycyclohexylamino)phenyl)-3-methylisoquinoline-2-oxide instead of compound (1d) and 3-quinolineboronic acid instead of 4-cyano-3-(ethylamino)phenylboronic acid pinacol ester.

Example 9

2-(4-Hydroxycyclohexylamino)-4-(5-(6-methylquinolin-3-yl)isoquinolin-1-yl)benzamide (9)

Compound (9) was obtained as a pale yellow solid (yield based on 2 steps: 60%) according to Example 2(3) using 3-bromo-6-methylquinoline instead of 3-amino-5-bromopyridine.

Example 10

2-(4-Hydroxycyclohexylamino)-4-(5-(7-methyl-1H-imidazo[4,5-b]pyridin-6-yl)isoquinolin-1-yl)benzamide (10)

Compound (10) was obtained as a pale yellow solid (yield based on 2 steps: 19%) according to Example 2(3) using 6-bromo-7-methyl-1H-imidazo[4,5-b]pyridine instead of 3-amino-5-bromopyridine and PdCl$_2$dppf instead of Pd(PPh$_3$)$_4$.

Example 11

2-(4-Hydroxycyclohexylamino)-4-(5-(7-methylquinolin-3-yl)isoquinolin-1-yl)benzamide (11)

Compound (11) was obtained as a pale yellow solid (yield based on 2 steps: 63%) according to Example 2(3) using 3-bromo-7-methylquinolin instead of 3-amino-5-bromopyridine.

Example 12

4-(5-(7-Methyl-1H-imidazo[4,5-b]pyridin-6-yl)isoquinolin-1-yl)-2-(4-hydroxycyclohexylamino)benzamide (12)

Compound (12) was obtained as a pale yellow solid (yield based on 2 steps: 17%) according to Example 2(3) using 6-bromo-1H-imidazo[4,5-b]pyridine instead of 3-amino-5-bromopyridine and PdCl$_2$dppf instead of Pd(PPh$_3$)$_4$.

Example 13

2-(4-Hydroxycyclohexylamino)-4-(5-(pyrido[2,3-b]pyrazin-7-yl)isoquinolin-1-yl)benzamide (13)

Compound (13) was obtained as a pale yellow solid (yield based on 2 steps: 30%) according to Example 2(3) using 7-bromo-pyrido[2,3-b]pyrazin instead of 3-amino-5-bromopyridine.

Example 14

4-(5-(1H-Pyrrolo[2,3-b]pyridin-5-yl)isoquinolin-1-yl)-2-(4-hydroxycyclohexylamino)benzamide (14)

Compound (14) was obtained as a pale yellow solid (yield based on 2 steps: 68%) according to Example 2(3) using 5-bromo-1H-pyrrolo[2,3-b]pyridine instead of 3-amino-5-bromopyridine and PdCl$_2$dppf instead of Pd(PPh$_3$)$_4$.

Example 15

2-(4-Hydroxycyclohexylamino)-4-(5-(pyridin-3-yl)isoquinolin-1-yl)benzamide (15)

Compound (15) was obtained as a pale yellow solid (yield based on 2 steps: 58%) according to Example 2(3) using 3-bromopyridin instead of 3-amino-5-bromopyridine.

Example 16

2-(4-Hydroxycyclohexylamino)-4-(5-(6-methoxypyridin-3-yl)isoquinolin-1-yl)benzamide (16)

Compound (16) was obtained as a pale yellow solid (yield based on 2 steps: 57%) according to Example 2(3) using 3-bromo-6-methoxypyridin instead of 3-amino-5-bromopyridine.

Example 17

2-(4-Hydroxycyclohexylamino)-4-(5-(5-(hydroxymethyl)pyridin-3-yl)isoquinolin-1-yl)benzamide (17)

Compound (17) was obtained as a pale yellow solid (yield based on 2 steps: 40%) according to Example 2(3) using 3-bromo-5-(hydroxymethyl)pyridin instead of 3-amino-5-bromopyridine.

Example 18

2-(4-Hydroxycyclohexylamino)-4-(5-(thiazol-5-yl)isoquinolin-1-yl)benzamide (18)

Compound (18) was obtained as a pale yellow solid (yield based on 2 steps: 75%) according to Example 2(3) using 5-bromothiazol instead of 3-amino-5-bromopyridine.

Example 19

Tert-butyl 2-(5-(1-(4-carbamoyl-3-(4-hydroxycyclo-hexylamino)phenyl)isoquinolin-5-yl)pyridin-3-yl)ethylcarbamate (19)

Compound (19) was obtained as a pale yellow solid (yield based on 2 steps: 49%) according to Example 2(3) using tert-butyl 2-(5-bromopyridin-3-yl)ethylcarbamate instead of 3-amino-5-bromopyridine.

Example 20

4-(5-(5-(2-Aminoethyl)pyridin-3-yl)isoquinolin-1-yl)-2-(4-hydroxycyclohexylamino)benzamide (20)

A solution of compound (19) (0.047 g) in TFA was stirred at room temperature for 3 hours. The solvent was distilled off, and chloroform was added to the residue. The reaction solution was neutralized with an aqueous sodium bicarbonate solution and partitioned into organic and aqueous layers. The organic layer was washed with brine and then dried over anhydrous sodium sulfate. The solvent was distilled off, and diethyl ether was added to the residue. The deposit was filtrated to obtain compound (20) (0.022 g, yield: 60%) as a white solid.

Example 21

2-(4-Hydroxycyclohexylamino)-4-(5-(5-phenyl-1,3,4-oxadiazol-2-yl)isoquinolin-1-yl)benzamide (21)

Compound (21) was obtained as a pale yellow solid (yield based on 2 steps: 40%) according to Example 2(3) using 2-bromo-5-phenyl-1,3,4-oxadiazol instead of 3-amino-5-bromopyridine.

Example 22

2-(4-Hydroxycyclohexylamino)-4-(5-(2-phenylthiazol-5-yl)isoquinolin-1-yl)benzamide (22)

Compound (22) was obtained as a pale yellow solid (yield based on 2 steps: 55%) according to Example 2(3) using 5-bromo-2-phenylthiazol instead of 3-amino-5-bromopyridine.

Example 23

2-(4-Hydroxycyclohexylamino)-4-(5-(5-phenyl-1,3,4-thiadiazol-2-yl)isoquinolin-1-yl)benzamide (23)

Compound (23) was obtained as a pale yellow solid (yield based on 2 steps: 30%) according to Example 2(3) using 2-bromo-5-phenyl-1,3,4-thiadiazol instead of 3-amino-5-bromopyridine.

Example 24

2-(4-Hydroxycyclohexylamino)-4-(5-(5-methoxypyridin-3-yl)isoquinolin-1-yl)benzamide (24)

Compound (24) was obtained as a pale yellow solid (yield based on 2 steps: 64%) according to Example 2(3) using 3-bromo-5-methoxypyridin instead of 3-amino-5-bromopyridine.

Example 25

2-(4-Hydroxycyclohexylamino)-4-(5-(4-(pyridin-4-yl)-1H-imidazol-1-yl)isoquinolin-1-yl)benzamide (25)

1-Chloro-5-(4-(pyridin-4-yl)-1H-imidazol-1-yl)isoquinoline was obtained according to Example 1(4) using 4-(1H-imidazol-4-yl)pyridine dihydrochloride instead of 4-(1H-imidazol-4-yl)-1-methyl-1H-pyrazole hydrochloride. Compound (25) was obtained as a pale yellow solid (yield based on 5 steps: 3%) according to Example 1(5) using the obtained 1-chloro-5-(4-(pyridin-4-yl)-1H-imidazol-1-yl)isoquinoline instead of compound (1d) and 4-cyano-3-(4-hydroxycyclohexylamino)phenylboronic acid pinacol ester instead of 4-cyano-3-(ethylamino)phenylboronic acid pinacol ester.

Example 26

2-(4-Hydroxycyclohexylamino)-4-(5-(5-(morpholinomethyl)pyridin-3-yl)isoquinolin-1-yl)benzamide (26)

Compound (26) was obtained as a pale yellow solid (yield based on 2 steps: 57%) according to Example 2(3) using 4-((5-bromopyridin-3-yl)methyl)morpholine instead of 3-amino-5-bromopyridine.

Example 27

4-(5-(5-Acetamidepyridin-3-yl)isoquinolin-1-yl)-2-(4-hydroxycyclohexylamino)benzamide (27)

Compound (27) was obtained as a pale yellow solid (yield based on 2 steps: 58%) according to Example 2(3) using N-(5-bromopyridin-3yl)acetamide instead of 3-amino-5-bromopyridine.

Example 28

4-(5-(5-(2-Hydroxyacetamide)pyridin-3-yl)isoquinolin-1-yl)-2-(4-hydroxycyclohexylamino)benzamide (28)

Compound (28) was obtained as a pale yellow solid (yield based on 2 steps: 25%) according to Example 2(3) using 2-(5-bromopyridin-3-ylamino)-2-oxoethylacetate instead of 3-amino-5-bromopyridine.

Example 29

5-(1-(4-Carbamoyl-3-(4-hydroxycyclohexylamino)phenyl)isoquinolin-5-yl)-N-propylnicotinamide (29)

Compound (29) was obtained as a pale yellow solid (yield based on 2 steps: 65%) according to Example 2(3) using 5-bromo-N-propylnicotinamide instead of 3-amino-5-bromopyridine.

Example 30

5-(1-(4-Carbamoyl-3-(4-hydroxycyclohexylamino)
phenyl)isoquinolin-5-yl)-N-(1-methylpiperidin-4-yl)
nicotinamide (30)

Compound (30) was obtained as a pale yellow solid (yield based on 2 steps: 41%) according to Example 2(3) using 5-bromo-N-(1-methylpiperidin-4-yl)nicotinamide instead of 3-amino-5-bromopyridine.

Example 31

2-(4-Hydroxycyclohexylamino)-4-(3-(morpholinomethyl)-5-(quinolin-3-yl)isoquinolin-1-yl)benzamide (31)

5-Bromo-3-methylisoquinoline-2-oxide was obtained according to Example 1(1) using 5-bromo-3-methylisoquinoline instead of 5-bromoisoquinoline. 3-(1-Chloro-3-methylisoquinolin-5-yl)quinoline was obtained according to Example 5(1) using the obtained 5-bromo-3-methylisoquinoline-2-oxide instead of compound (3a) and Pd(PPh$_3$)$_4$ instead of PdCl$_2$dppf. A suspension of the obtained 3-(1-chloro-3-methylisoquinolin-5-yl)quinoline (0.151 g), NBS (0.098 g), and AIBN (0.017 g) in carbon tetrachloride (5 ml) was heated to reflux overnight. After cooling, insoluble matter was filtered off using celite. THF (3 ml), morpholine (0.1 ml), and diisopropylethylamine (0.2 ml) were added to the filtrate, and the mixture was stirred at room temperature for 3 hours. The solvent was distilled off, and the residue was partitioned between ethyl acetate and water. The organic layer was washed with brine. The organic layer thus washed was dried over anhydrous sodium sulfate. Then, the solvent was distilled off, and the residue was purified by neutral silica gel column chromatography (chloroform/methanol) to obtain 4-((1-chloro-5-(quinolin-3-yl)isoquinolin-3-yl)methyl)morpholine (25 mg). Compound (31) was obtained as a pale yellow solid (yield based on 7 steps: 1%) according to Example 1(5) using the obtained 4-((1-chloro-5-(quinolin-3-yl)isoquinolin-3-yl)methyl)morpholine instead of compound (1d) and 4-cyano-3-(4-hydroxycyclohexylamino)phenylboronic acid pinacol ester instead of 4-cyano-3-(ethylamino)phenylboronic acid pinacol ester.

Example 32

2-(4-Hydroxycyclohexylamino)-4-(5-(4-(pyridin-3-yl)-1H-imidazol-1-yl)isoquinolin-1-yl)benzamide (32)

1-Chloro-5-(4-(pyridin-3-yl)-1H-imidazol-1-yl)isoquinoline was obtained according to Example 1(4) using 3-(1H-imidazol-4-yl)pyridine dihydrochloride instead of 4-(1H-imidazol-4-yl)-1-methyl-1H-pyrazole hydrochloride. Compound (32) was obtained as a pale yellow solid (yield based on 5 steps: 1%) according to Example 1(5) using the obtained 1-chloro-5-(4-(pyridin-3-yl)-1H-imidazol-1-yl)isoquinoline instead of compound (1d) and 4-cyano-3-(4-hydroxycyclohexylamino)phenylboronic acid pinacol ester instead of 4-cyano-3-(ethylamino)phenylboronic acid pinacol ester.

Example 33

4-(2-Carbamoyl-5-(5-(quinolin-3-yl)isoquinolin-1-yl)phenylamino)cyclohexyl-2-aminoacetate (33)

A solution of compound (6) (0.67 g), 2-(t-butoxycarbonylamino)acetic acid (0.60 g), EDCI hydrochloride (0.675 g), and 4-N,N-dimethylaminopyridine (0.017 g) in dimethylformamide (9 ml) was stirred overnight at room temperature. The reaction solution was partitioned between ethyl acetate and water. The organic layer was washed with brine. The organic layer thus washed was dried over anhydrous sodium sulfate. Then, the solvent was distilled off, and the residue was used in the next reaction without being purified. Trifluoroacetic acid (2 ml) was added to a solution of the residue in methylene chloride (4 ml), and the mixture was stirred overnight at room temperature. The reaction solution was partitioned between chloroform and water. The organic layer was neutralized with an aqueous sodium bicarbonate solution and washed with brine. The organic layer thus washed was dried over anhydrous sodium sulfate. Then, the solvent was distilled off, and the residue was purified by neutral silica gel column chromatography (chloroform/methanol) to obtain compound (33) (0.54 g, yield based on 2 steps: 72%) as a white solid.

Example 34

2-(4-Hydroxycyclohexylamino)-4-(5-(5-(methylamino)pyridin-3-yl)isoquinolin-1-yl)benzamide (34)

Tert-butyl 5-(1-(4-carbamoyl-3-(4-hydroxycyclohexylamino)phenyl)isoquinolin-5-yl)pyridin-3-yl(methyl)carbamate was obtained according to Example 2(3) using tert-butyl 5-bromopyridin-3-yl(methyl)carbamate instead of 3-amino-5-bromopyridine. A solution of the obtained compound (0.070 g) in trifluoroacetic acid (2 ml) was stirred at room temperature for 1 hour. The solvent was distilled off. Then, potassium carbonate (0.5 g) and methanol (3 ml) were added to the residue, and the mixture was stirred at room temperature for 1 hour. Water was added to the reaction solution, followed by extraction with ethyl acetate. The organic layer was washed with water and brine in this order and then dried over anhydrous sodium sulfate. The solvent was distilled off, and acetonitrile was then added to the residue. The deposit was filtrated to obtain compound (34) (0.036 g, yield based on 3 steps: 51%) as a pale yellow solid.

Example 35

2-(4-Hydroxycyclohexylamino)-4-(5-(5-(propylamino)pyridin-3-yl)isoquinolin-1-yl)benzamide (35)

Compound (35) was obtained as a pale yellow solid (0.036 g, yield based on 3 steps: 17%) according to Example 34 using 5-bromopyridin-3-yl(propyl)carbamate instead of tert-butyl 5-bromopyridin-3-yl(methyl)carbamate.

Example 36

4-(5-(5-(Cyclobutylmethylamino)pyridin-3-yl)isoquinolin-1-yl)-2-(4-hydroxycyclohexylamino)benzamide (36)

Compound (36) was obtained as a pale yellow solid (0.036 g, yield based on 3 steps: 39%) according to Example 34 using 5-bromopyridin-3-yl(cyclopropylmethyl)carbamate instead of tert-butyl 5-bromopyridin-3-yl(methyl)carbamate

Example 37

2-(4-Hydroxycyclohexylamino)-N-(((2-hydroxyethyl)(methyl)amino)methyl)-4-(5-(quinolin-3-yl)isoquinolin-1-yl)benzamide (37)

A solution of paraformaldehyde (0.122 g), 2-(methylamino)ethanol (0.330 g), and acetic acid (0.13 ml) in ethanol (4 ml) was stirred at 80° C. for 2 hours. After cooling, a solution of compound (6) (0.200 g) in methylene chloride (4 ml) was added to the reaction solution, and the mixture was stirred overnight at room temperature. The reaction solution was partitioned between chloroform and water. The organic layer was neutralized with an aqueous sodium bicarbonate solution, then washed with brine, and then dried over anhydrous sodium sulfate. The solvent was distilled off, and the residue was then purified by neutral silica gel column chromatography (chloroform/methanol) to obtain compound (37) (0.130 g, 56%) as a pale yellow solid.

Example 38

N-((dimethylamino)methyl)-2-(4-hydroxycyclohexylamino)-4-(5-(quinolin-3-yl)isoquinolin-1-yl)benzamide (38)

A solution of compound (6) (0.050 g) and N,N-dimethylmethylene ammonium iodide (0.025 g) in methylene chloride (1 ml) was stirred overnight at room temperature. The reaction solution was partitioned between chloroform and water. The organic layer was neutralized with an aqueous sodium bicarbonate solution, then washed with brine, and then dried over anhydrous sodium sulfate. The solvent was distilled off, and the residue was then purified by neutral silica gel column chromatography (chloroform/methanol) to obtain compound (38) (0.053 g, 95%) as a pale yellow solid.

Example 39

4-(5-(1H-Pyrrolo[3,2-b]pyridin-6-yl)isoquinolin-1-yl)-2-(4-hydroxycyclohexylamino)benzamide (39)

Compound (39) was obtained as a pale yellow solid (yield based on 2 steps: 59%) according to Example 2(3) using 6-bromo-1H-pyrrolo[3,2-b]pyridine instead of 3-amino-5-bromopyridine and PdCl$_2$dppf instead of Pd(PPh$_3$)$_4$.

Example 40

2-(4-Hydroxycyclohexylamino)-4-(5-(2-methyl-1H-imidazo[4,5-b]pyridin-6-yl)isoquinolin-1-yl)benzamide (40)

Compound (40) was obtained as a pale yellow solid (yield based on 2 steps: 23%) according to Example 2(3) using 6-bromo-2-methyl-1H-pyrrolo[4,5-b]pyridine instead of 3-amino-5-bromopyridine.

Example 41

4-(5-(2-Ethyl-1H-imidazo[4,5-b]pyridin-6-yl)isoquinolin-1-yl)-2-(4-hydroxycyclohexylamino)benzamide (41)

Compound (41) was obtained as a pale yellow solid (yield based on 2 steps: 47%) according to Example 2(3) using 6-bromo-2-ethyl-1H-pyrrolo[4,5-b]pyridine instead of 3-amino-5-bromopyridine and PdCl$_2$dppf instead of Pd(PPh$_3$)$_4$.

Example 42

4-(5-(Quinolin-3-yl)isoquinolin-1-yl)benzamide (42)

Compound (42) was obtained as a white solid (yield based on 4 steps: 37%) according to Example 6 using 4-cyanophenylboronic acid instead of 4-cyano-3-(4-hydroxycyclohexylamino)phenylboronic acid pinacol ester.

Example 43

2-(4-Hydroxycyclohexylamino)-4-(5-(pyrimidin-5-yl)isoquinolin-1-yl)benzamide (43)

Compound (43) was obtained as a pale yellow solid (yield based on 2 steps: 54%) according to Example 2(3) using 5-bromopyrimidin instead of 3-amino-5-bromopyridine.

Example 44

2,5-Dimethyl-4-(5-(quinolin-3-yl)isoquinolin-1-yl)benz

Compound (44) was obtained as a white solid (yield based on 4 steps: 33%) according to Example 6 using 4-cyano-2,5-dimethylphenylboronic acid instead of 4-cyano-3-(4-hydroxycyclohexylamino)phenylboronic acid pinacol ester.

Example 45

4-(5-(7-Formylquinolin-3-yl)isoquinolin-1-yl)-2-(4-hydroxycyclohexylamino)benzamide (45)

Compound (45) was obtained as a pale yellow solid (yield based on 2 steps: 20%) according to Example 2(3) using 3-bromo-7-formylquinolin instead of 3-amino-5-bromopyridine.

Example 46

4-(5-(6-Ethylamino)pyrazin-2-yl)isoquinolin-1-yl)-2-(4-hydroxycyclohexylamino)benzamide (46)

Compound (46) was obtained as a pale yellow solid (yield based on 2 steps: 30%) according to Example 2(3) using 2-amino-6-bromopyrazin instead of 3-amino-5-bromopyridine.

Example 47

2-(4-Hydroxycyclohexylamino)-4-(5-(6-methoxypyridazin-3-yl)isoquinolin-1-yl)benzamide (47)

Compound (47) was obtained as a pale yellow solid (yield based on 2 steps: 51%) according to Example 2(3) using 2-bromo-5-methoxypyridazin instead of 3-amino-5-bromopyridine.

Example 48

2-(4-Hydroxycyclohexylamino)-4-(5-(4-(1-methyl-1H-pyrazol-4-yl)-1H-imidazol-1-yl)isoquinolin-1-yl)benzamide (48)

Compound (48) was obtained as a pale yellow solid (yield based on 2 steps: 53%) according to Example 1(5) using

Example 49

2-(4-Hydroxycyclohexylamino)-4-(5-(6-(morpholinomethyl)quinolin-3-yl)isoquinolin-1-yl)benzamide (49)

Compound (49) was obtained as a pale yellow solid (yield based on 2 steps: 45%) according to Example 2(3) using 4-((3 bromoquinolin-6-yl)methyl)morpholine instead of 3-amino-5-bromopyridine.

Example 50

3-Methyl-4-(5-(4-(pyridin-3-yl)-1H-imidazol-1-yl)isoquinolin-1-yl)benzamide (50)

Compound (50) was obtained as a pale yellow solid (yield based on 5 steps: 9%) according to Example 32 using 4-cyano-2-methylphenylboronic acid instead of 4-cyano-3-(4-hydroxycyclohexylamino)phenylboronic acid pinacol ester.

Example 51

3-Methyl-4-(5-(4-(pyridin-4-yl)-1H-imidazol-1-yl)isoquinolin-1-yl)benzamide (51)

Compound (51) was obtained as a pale yellow solid (yield based on 5 steps: 14%) according to Example 25 using 4-cyano-2-methylphenylboronic acid instead of 4-cyano-3-(4-hydroxycyclohexylamino)phenylboronic acid pinacol ester.

Example 52

2-(4-Hydroxycyclohexylamino)-4-(5-(4-(1-isobutyl-1H-pyrazol-4-yl)-1H-imidazol-1-yl)isoquinolin-1-yl)benzamide (52)

A suspension of compound (2b) (0.188 g), 4-(1H-imidazol-4-yl)-1-isobutyl-1H-pyrazole (0.0837 g), and copper(I) oxide (0.003 g) in MeOH (200 mL) was stirred, open to air, at room temperature for 2 days. Chloroform was added to the reaction solution, which was then filtered using celite. The solvent was distilled off, and the residue was purified by neutral silica gel column chromatography (chloroform/methanol) to obtain a white solid. An aqueous sodium hydroxide solution (4 M, 0.093 mL) and a 30% aqueous hydrogen peroxide solution (0.045 mL) were added to a solution of the obtained white solid in DMSO (3 mL) and ethanol (1.5 mL) at room temperature, and the mixture was stirred for 30 minutes. Water was added to the reaction solution, and the deposit was collected by filtration, then washed with water and ether by sprinkling, and then dried under reduced pressure to obtain compound (52) (0.040 g, yield based on 2 steps: 26%) as a pale yellow solid.

Example 53

2-(4-Hydroxycyclohexylamino)-4-(5-(4-(1-isopropyl-1H-pyrazol-4-yl)-1H-imidazol-1-yl)isoquinolin-1-yl)benzamide (53)

Compound (53) was obtained as a pale yellow solid (yield based on 2 steps: 8%) according to Example 52 using 4-(1H-imidazol-4-yl)-1-isopropyl-1H-pyrazole instead of 4-(1H-imidazol-4-yl)-1-isobutyl-1H-pyrazole.

Example 54

4-(5-(4-Bromo-1H-imidazol-1-yl)isoquinolin-1-yl)-2-(4-hydroxycyclohexylamino)benzamide (54)

Compound (54) was obtained as a pale yellow solid (yield based on 2 steps: 22%) according to Example 52 using 4-bromo-1H-imidazol instead of 4-(1H-imidazol-4-yl)-1-isobutyl-1H-pyrazole.

Example 55

4-(5-(4-Acetyl-1H-imidazol-1-yl)isoquinolin-1-yl)-2-(4-hydroxycyclohexylamino)benzamide (55)

Compound (55) was obtained as a pale yellow solid (yield based on 2 steps: 20%) according to Example 52 using 4-acetyl-1H-imidazol instead of 4-(1H-imidazol-4-yl)-1-isobutyl-1H-pyrazole.

Example 56

5-(1-(4-Carbamoyl-3-(4-hydroxycyclohexylamino)phenyl)isoquinolin-5-yl)-N-methylpicolinamide (56)

Compound (56) was obtained as a pale yellow solid (yield based on 2 steps: 56%) according to Example 2(3) using 5-bromo-N-propylpicolinamide instead of 3-amino-5-bromopyridine.

Example 57

5-(1-(4-Carbamoyl-3-(4-hydroxycyclohexylamino)phenyl)isoquinolin-5-yl)-N-phenylpicolinamide (57)

Compound (57) was obtained as a pale yellow solid (yield based on 2 steps: 55%) according to Example 2(3) using 5-bromo-N-phenylpicolinamide instead of 3-amino-5-bromopyridine.

Example 58

4-(5-(4-(1-Methyl-1H-pyrazol-4-yl)-1H-imidazol-1-yl)isoquinolin-1-yl)-2-(methylamino)benzamide (58)

Compound (58) was obtained as a pale yellow solid (yield based on 2 steps: 53%) according to Example 1(5) using 4-cyano-3-methylaminophenylboronic acid pinacol ester instead of 4-cyano-3-(ethylamino)phenylboronic acid pinacol ester.

Example 59

4-(5-(4-(1-Methyl-1H-pyrazol-4-yl)-1H-imidazol-1-yl)isoquinolin-1-yl)-2-((tetrahydrofuran-2-yl)methylamino)benzamide (59)

Compound (59) was obtained as a pale yellow solid (yield based on 2 steps: 55%) according to Example 1(5) using 4-cyano-3-((tetrahydrofuran-2-yl)methylamino)phenylboronic acid pinacol ester instead of 4-cyano-3-(ethylamino)phenylboronic acid pinacol ester.

Example 60

4-(5-(4-(1-Methyl-1H-pyrazol-4-yl)-1H-imidazol-1-yl)isoquinolin-1-yl)-2-(2-(pyridin-2-yl)ethylamino)benzamide (60)

Compound (60) was obtained as a pale yellow solid (yield based on 2 steps: 52%) according to Example 1(5) using 4-cyano-3-(2-(pyridin-2-yl)ethylamino)phenylboronic acid pinacol ester instead of 4-cyano-3-(ethylamino)phenylboronic acid pinacol ester.

Example 61

2-(Isopropylamino)-4-(5-(4-(1-methyl-1H-pyrazol-4-yl)-1H-imidazol-1-yl)isoquinolin-1-yl)benzamide (61)

Compound (61) was obtained as a pale yellow solid (yield based on 2 steps: 34%) according to Example 1(5) using 4-cyano-3-(isopropylamino)phenylboronic acid pinacol ester instead of 4-cyano-3-(ethylamino)phenylboronic acid pinacol ester.

Example 62

2-(2-Methoxyethylamino)-4-(5-(4-(1-methyl-1H-pyrazol-4-yl)-1H-imidazol-1-yl)isoquinolin-1-yl)benzamide (62)

Compound (62) was obtained as a pale yellow solid (yield based on 2 steps: 55%) according to Example 1(5) using 4-cyano-3-(2-methoxyethylamino)phenylboronic acid pinacol ester instead of 4-cyano-3-(ethylamino)phenylboronic acid pinacol ester.

Example 63

2-(Cycloheptylamino)-4-(5-(4-(1-methyl-1H-pyrazol-4-yl)-1H-imidazol-1-yl)isoquinolin-1-yl)benzamide (63)

Compound (63) was obtained as a pale yellow solid (yield based on 2 steps: 59%) according to Example 1(5) using 4-cyano-3-(cycloheptylamino)phenylboronic acid pinacol ester instead of 4-cyano-3-(ethylamino)phenylboronic acid pinacol ester.

Example 64

2-(Isopropylmethylamino)-4-(8-(4-(1-methyl-1H-pyrazol-4-yl)-1H-imidazol-1-yl)-2-(trifluoromethyl)quinolin-4-yl)benzamide (64)

Compound (64) was obtained as a pale yellow solid (yield based on 2 steps: 64%) according to Example 3(3) using 4-cyano-3-(isopropylamino)phenylboronic acid pinacol ester instead of 4-cyano-3-(ethylamino)phenylboronic acid pinacol ester.

Example 65

2-(Cyclopropylmethylamino)-4-(8-(4-(1-methyl-1H-pyrazol-4-yl)-1H-imidazol-1-yl)-2-(trifluoromethyl)quinolin-4-yl)benzamide (65)

Compound (65) was obtained as a pale yellow solid (yield based on 2 steps: 50%) according to Example 3(3) using 4-cyano-3-(cyclopropylmethylamino)phenylboronic acid pinacol ester instead of 4-cyano-3-(ethylamino)phenylboronic acid pinacol ester.

Example 66

2-(Ethylamino)-4-(3-methyl-5-(4-(1-methyl-1H-pyrazol-4-yl)-1H-imidazol-1-yl)isoquinolin-1-yl)benzamide (66)

1-(Benzyloxy)-5-bromo-3-methylisoquinoline was obtained according to Example 1(3) using compound (8a) instead of compound (1b). 1-Chloro-3-methyl-5-(4-(1-methyl-1H-pyrazol-4-yl)-1H-imidazol-1-yl)isoquinoline was obtained according to Example 1(4) using the obtained 1-(benzyloxy)-5-bromo-3-methylisoquinoline instead of compound (1c). Compound (66) was obtained as a white solid (yield based on 6 steps: 27%) according to Example 1(5) using the obtained 1-chloro-3-methyl-5-(4-(1-methyl-1H-pyrazol-4-yl)-1H-imidazol-1-yl)isoquinoline instead of compound (1d).

Example 67

2-(Isopropylamino)-4-(3-methyl-5-(4-(1-methyl-1H-pyrazol-4-yl)-1H-imidazol-1-yl)isoquinolin-1-yl)benzamide (67)

Compound (67) was obtained as a pale yellow solid (yield based on 6 steps: 19%) according to Example 66 using 4-cyano-3-(isopropylamino)phenylboronic acid pinacol ester instead of 4-cyano-3-(ethylamino)phenylboronic acid pinacol ester.

Example 68

2-(Cyclopropylmethylamino)-4-(3-methyl-5-(4-(1-methyl-1H-pyrazol-4-yl)-1H-imidazol-1-yl)isoquinolin-1-yl)benzamide (68)

Compound (68) was obtained as a white solid (yield based on 6 steps: 18%) according to Example 66 using 4-cyano-3-(cyclopropylmethylamino)phenylboronic acid pinacol ester instead of 4-cyano-3-(ethylamino)phenylboronic acid pinacol ester.

Example 69

2-Amino-4-(8-(4-(1-methyl-1H-pyrazol-4-yl)-1H-imidazol-1-yl)-2-(trifluoromethyl)quinolin-4-yl)benzamide (69)

Compound (69) was obtained as a pale yellow solid (yield based on 2 steps: 77%) according to Example 3(3) using 3-amino-4-cyanophenylboronic acid pinacol ester instead of 4-cyano-3-(ethylamino)phenylboronic acid pinacol ester.

Example 70

2-Fluoro-4-(8-(4-(1-methyl-1H-pyrazol-4-yl)-1H-imidazol-1-yl)-2-(trifluoromethyl)quinolin-4-yl)benzamide (70)

Compound (70) was obtained as a pale yellow solid (yield based on 2 steps: 24%) according to Example 3(3) using 4-cyano-3-fluorophenylboronic acid instead of 4-cyano-3-(ethylamino)phenylboronic acid pinacol ester.

Example 71

2-Amino-4-(3-methyl-5-(4-(1-methyl-1H-pyrazol-4-yl)-1H-imidazol-1-yl)isoquinolin-1-yl)benzamide (71)

Compound (71) was obtained as a white solid (yield based on 6 steps: 22%) according to Example 66 using 3-amino-4-cyanophenylboronic acid pinacol ester instead of 4-cyano-3-(ethylamino)phenylboronic acid pinacol ester.

Example 72

2-Ethylamino-4-(4-(4-(1-methyl-1H-pyrazol-4-yl)-1H-imidazol-1-yl)1,7-naphthyridin-8-yl)benzamide (72)

A suspension of 3-amino-2-chloropyridine (17.6 g) and 5-(methoxymethylene)-2,2-dimethyl-1,3-dioxane-4,6-dione (25.5 g) in isopropanol (274 ml) was heated to reflux for 5 minutes. After cooling, the deposit was filtrated to obtain 5-((2-chloropyridin-3-ylamino)methylene)-2,2-dimethyl-1,3-dioxane-4,6-dione (34.8 g). The obtained 5-((2-chloropyridin-3-ylamino)methylene)-2,2-dimethyl-1,3-dioxane-4,6-dione (8.2 g) was gradually added to Dowtherm heated to 220° C., and the mixture was heated at 220° C. for 30 minutes. After cooling, hexane (300 ml) was added to the reaction solution, and the deposit was filtrated to obtain 8-chloro-1,7-naphthyridin-4(1H)-one (2.02 g). 4-(4-Chloro-1,7-naphthyridin-8-yl)-2-(ethylamino)benzonitrile (0.107 g) was obtained according to Example 5(1) using the obtained 8-chloro-1,7-naphthyridin-4(1H)-one (0.295 g) instead of compound (3a) and 4-cyano-3-(ethylamino)phenylboronic acid pinacol ester instead of 3-quinolineboronic acid. A suspension of the obtained 4-(4-chloro-1,7-naphthyridin-8-yl)-2-(ethylamino)benzonitrile (0.0491 g), 4-(1H-imidazol-4-yl)-1-methyl-1H-pyrazole hydrochloride (0.035 g), copper (II) oxide nanoparticles (0.06 g), and potassium carbonate (0.0883 g) in DMF (1.5 ml) was stirred overnight at 125° C. The reaction solution was partitioned between ethyl acetate and water. The organic layer was washed with brine. The organic layer thus washed was dried over anhydrous sodium sulfate. Then, the solvent was distilled off, and the residue was purified by neutral silica gel column chromatography (chloroform/methanol) to obtain 2-(ethylamino)-4-(4-(4-(1-methyl-1H-pyrazol-4-yl)-1H-imidazol-1-yl)-1,7-naphthyridin-8yl)benzonitrile. An aqueous sodium hydroxide solution (4 M, 0.093 mL) and a 30% aqueous hydrogen peroxide solution (0.045 mL) were added to a solution of the obtained 2-(ethylamino)-4-(4-(4-(1-methyl-1H-pyrazol-4-yl)-1H-imidazol-1-yl)-1,7-naphthyridin-8yl)benzonitrile in DMSO (3 mL) at room temperature, and the mixture was stirred for 30 minutes. Water was added to the reaction solution, and the deposit was collected by filtration, then washed with water and ether by sprinkling, and then dried under reduced pressure to obtain compound (72) (0.040 g, yield based on 6 steps: 4%) as a pale yellow solid.

Example 73

3-Amino-4-(8-(4-(1-methyl-1H-pyrazol-4-yl)-1H-imidazol-1-yl)-2-(trifluoromethyl)quinolin-4-yl)benzamide (73)

Compound (73) was obtained as a pale yellow solid (yield based on 2 steps: 16%) according to Example 3(3) using 2-amino-4-cyanophenylboronic acid pinacol ester instead of 4-cyano-3-(ethylamino)phenylboronic acid pinacol ester.

Example 74

3-Amino-4-(3-methyl-5-(4-(1-methyl-1H-pyrazol-4-yl)-1H-imidazol-1-yl)isoquinolin-1-yl)benzamide (74)

Compound (74) was obtained as a white solid (yield based on 6 steps: 12%) according to Example 66 using 2-amino-4-cyanophenylboronic acid pinacol ester instead of 4-cyano-3-(ethylamino)phenylboronic acid pinacol ester.

Example 75

3-Amino-4-(8-(4-(1-methyl-1H-pyrazol-4-yl)-1H-imidazol-1-yl)-2-(trifluoromethyl)quinazolin-4-yl)benzamide (75)

Compound (75) was obtained as a white solid (yield based on 2 steps: 14%) according to Example 4(3) using 2-amino-4-cyanophenylboronic acid pinacol ester instead of 3-amino-4-cyanophenylboronic acid pinacol ester.

Example 76

2-(Tert-butylamino)-4-(8-(4-(pyridin-3-yl)-1H-imidazol-1-yl)-2-(trifluoromethyl)quinolin-4-yl)benzamide (76)

4-Chloro-8-(4-(pyridin-3-yl)-1H-imidazol-1 yl)-2-(trifluoromethyl)quinoline was obtained according to Example 3(2) using 3-(1H-imidazol-4-yl)pyridin 2 hydrochloride instead of 4-(1H-imidazol-4-yl)-1-methyl-1H-pyrazole hydrochloride. Compound (76) was obtained as a pale yellow solid (yield based on 4 steps: 32%) according to Example 3(3) using the obtained 4-chloro-8-(4-(pyridin-3-yl)-1H-imidazol-1-yl)-2-(trifluoromethyl)quinoline instead of compound (3b) and 3-(tert-butylamino)-4-cyanophenylboronic acid pinacol ester instead of 4-cyano-3-(ethylamino)phenylboronic acid pinacol ester.

Example 77

2-(Ethylamino)-4-(8-(4-(pyridin-3-yl)-1H-imidazol-1-yl)-2-(trifluoromethyl)quinolin-4-yl)benzamide (77)

Compound (77) was obtained as a pale yellow solid (yield based on 4 steps: 30%) according to Example 76 using 4-cyano-3-(ethylamino)phenylboronic acid pinacol ester instead of 3-(tert-butylamino)-4-cyanophenylboronic acid pinacol ester.

Example 78

2-Amino-4-(8-(4-(pyridin-3-yl)-1H-imidazol-1-yl)-2-(trifluoromethyl)quinolin-4-yl)benzamide (78)

Compound (78) was obtained as a pale yellow solid (yield based on 4 steps: 30%) according to Example 76 using 3-amino-4-cyanophenylboronic acid pinacol ester instead of 3-(tert-butylamino)-4-cyanophenylboronic acid pinacol ester.

Example 79

2-(Tert-butylamino)-4-(8-(4-(1-methyl-1H-pyrazol-4-yl)-1H-imidazol-1-yl)-2-(trifluoromethyl)quinazolin-4-yl)benzamide (79)

A suspension of compound (4b) (0.757 g), 3-(tert-butylamino)-4-cyanophenylboronic acid pinacol ester (0.720 g), PdCl$_2$dppf (0.163 g), and potassium phosphate (1.30 g) in dioxane (10 ml) was stirred overnight at 90° C. in a nitrogen atmosphere. After cooling, chloroform was added thereto, and insoluble matter was filtered off using celite. The solvent in the filtrate was distilled off under reduced pressure. The residue was purified by neutral silica gel column chromatography (chloroform/methanol) to obtain 2-(tert-butylamino)-4-(8-(4-(1-methyl-1H-pyrazol-4-yl)-1H-imidazol-1-yl)quinazolin-4-yl)benzonitrile (0.655 g) as a white solid. An aqueous sodium hydroxide solution (4 M, 0.640 mL) and a 30% aqueous hydrogen peroxide solution (0.300 mL) were added to a solution of the obtained 2-(tert-butylamino)-4-(8-(4-(1-methyl-1H-pyrazol-4-yl)-1H-imidazol-1-yl)quinazolin-4-yl)benzonitrile (0.655 g) in DMSO (8 mL) and ethanol (4 mL) at room temperature, and the mixture was stirred for 30 minutes. Water was added to the reaction solution, and the deposit was collected by filtration, then washed with water and ether by sprinkling, and then dried under reduced pressure to obtain compound (79) (0.530 g, yield based on 2 steps: 50%) as a pale yellow solid.

Example 80

2-(Ethylamino)-4-(8-(4-(1-methyl-1H-pyrazol-4-yl)-1H-imidazol-1-yl)-2-(trifluoromethyl)quinazolin-4-yl)benzamide (80)

Compound (80) was obtained as a pale yellow solid (yield based on 2 steps: 40%) according to Example 79 using 4-cyano-3-(ethylamino)phenylboronic acid pinacol ester instead of 3-(tert-butylamino)-4-cyanophenylboronic acid pinacol ester.

Example 81

2-Chloro-4-(8-(4-(1-methyl-1H-pyrazol-4-yl)-1H-imidazol-1-yl)-2-(trifluoromethyl)quinolin-4-yl)benzamide (81)

Compound (81) was obtained as a pale yellow solid (yield based on 2 steps: 16%) according to Example 3(3) using 3-chloro-4-cyanophenylboronic acid pinacol ester instead of 4-cyano-3-(ethylamino)phenylboronic acid pinacol ester.

Example 82

2-Chloro-4-(3-methyl-5-(4-(1-methyl-1H-pyrazol-4-yl)-1H-imidazol-1-yl)isoquinolin-1-yl)benzamide (82)

Compound (82) was obtained as a white solid (yield based on 6 steps: 18%) according to Example 66 using 3-chloro-4-cyanophenylboronic acid pinacol ester instead of 4-cyano-3-(ethylamino)phenylboronic acid pinacol ester.

Example 83

5-(8-(4-(1-Methyl-1H-pyrazol-4-yl)-1H-imidazol-1-yl)-2-(trifluoromethyl)quinolin-4-yl)picolinamide (83)

Compound (83) was obtained as a pale yellow solid (yield based on 2 steps: 40%) according to Example 3(3) using 6-cyanopyridin-3-ylboronic acid instead of 4-cyano-3-(ethylamino)phenylboronic acid pinacol ester.

Example 84

3-Methyl-4-(8-(4-(1-methyl-1H-pyrazol-4-yl)-1H-imidazol-1-yl)-2-(trifluoromethyl)quinolin-4-yl)benzamide (84)

Compound (84) was obtained as a white solid (yield based on 2 steps: 68%) according to Example 3(3) using 4-cyano-2-methylphenylboronic acid instead of 4-cyano-3-(ethylamino)phenylboronic acid pinacol ester.

Example 85

2-(Tert-butylamino)-4-(8-(4-(1-methyl-1H-pyrazol-4-yl)-1H-imidazol-1-yl)-2-(trifluoromethyl)quinazolin-4-yl)benzamide (85)

Compound (85) was obtained as a pale yellow solid (yield based on 2 steps: 31%) according to Example 79 using 4-cyano-2-methylphenylboronic acid instead of 3-(tert-butylamino)-4-cyanophenylboronic acid pinacol ester.

Example 86

2-(Tert-butylamino)-4-(8-(4-(1-methyl-1H-pyrazol-4-yl)-1H-imidazol-1-yl)-2-(trifluoromethyl)quinolin-4-yl)benzamide (86)

Compound (86) was obtained as a pale yellow solid (yield based on 2 steps: 66%) according to Example 3(3) using 3-(tert-butylamino)-4-cyanophenylboronic acid pinacol ester instead of 4-cyano-3-(ethylamino)phenylboronic acid pinacol ester.

Example 87

4-(8-(4-(1-Methyl-1H-pyrazol-4-yl)-1H-imidazol-1-yl)-2-(trifluoromethyl)quinolin-4-yl)-3-(propylamino)benzamide (87)

Compound (87) was obtained as a pale yellow solid (yield based on 2 steps: 35%) according to Example 3(3) using 4-cyano-2-(propylamino)phenylboronic acid pinacol ester instead of 4-cyano-3-(ethylamino)phenylboronic acid pinacol ester.

Example 88

5-(8-(4-(Pyridin-3-yl)-1H-imidazol-1-yl)-2-(trifluoromethyl)quinolin-4-yl)picolinamide (88)

Compound (88) was obtained as a pale yellow solid (yield based on 4 steps: 15%) according to Example 76 using 6-cyanopyridin-3-ylboronic acid instead of 3-(tert-butylamino)-4-cyanophenylboronic acid pinacol ester.

Example 89

4-(8-(4-(1-Ethyl-1H-pyrazol-4-yl)-1H-imidazol-1-yl)-2-(trifluoromethyl)quinolin-4-yl)-2-(ethylamino)benzamide (89)

4-Chloro-8-(4-(1-ethyl-1H-pyrazol-4-yl)-1H-imidazol-1-yl)-2-(trifluoromethyl)quinoline was obtained according to Example 3(2) using 4-(1H-imidazol-4-yl)-1-ethyl-1H-pyrazole hydrochloride instead of 4-(1H-imidazol-4-yl)-1-methyl-1H-pyrazole hydrochloride. Compound (89) was obtained as a pale yellow solid (yield based on 4 steps: 13%) according to Example 3(3) using the obtained 4-chloro-8-(4-(1-ethyl-1H-pyrazol-4-yl)-1H-imidazol-1-yl)-2-(trifluoromethyl)quinoline instead of compound (3b).

Example 90

2-(Tert-butylamino)-4-(8-(4-(1-ethyl-1H-pyrazol-4-yl)-1H-imidazol-1-yl)-2-(trifluoromethyl)quinolin-4-yl)benzamide (90)

Compound (90) was obtained as a pale yellow solid (yield based on 4 steps: 15%) according to Example 89 using 3-(tert-butylamino)-4-cyanophenylboronic acid pinacol ester instead of 4-cyano-3-(ethylamino)phenylboronic acid pinacol ester.

Example 91

4-(8-(4-(1-Difluoromethyl-1H-pyrazol-4-yl)-1H-imidazol-1-yl)-2-(trifluoromethyl)quinolin-4-yl)-2-(ethylamino)benzamide (91)

4-Chloro-8-(4-(1-(difluoromethyl)-1H-pyrazol-4-yl)-1H-imidazol-1-yl)-2-(trifluoromethyl)quinoline was obtained according to Example 3(2) using 1-(difluoromethyl)-4-(1H-imidazol-4-yl)-1H-pyrazole hydrochloride instead of 4-(1H-imidazol-4-yl)-1-methyl-1H-pyrazole hydrochloride. Compound (91) was obtained as a pale yellow solid (yield based on 4 steps: 10%) according to Example 3(3) using the obtained 4-chloro-8-(4-(1-(difluoromethyl)-1H-pyrazol-4-yl)-1H-imidazol-1-yl)-2-(trifluoromethyl)quinoline instead of compound (3b).

Example 92

2-(Tert-butylamino)-4-(8-(4-(1-difluoromethyl-1H-pyrazol-4-yl)-1H-imidazol-1-yl)-2-(trifluoromethyl)quinolin-4-yl)benzamide (92)

Compound (92) was obtained as a pale yellow solid (yield based on 4 steps: 14%) according to Example 91 using 3-(tert-butylamino)-4-cyanophenylboronic acid pinacol ester instead of 4-cyano-3-(ethylamino)phenylboronic acid pinacol ester.

Example 93

2-(Tert-butylamino)-4-(3-methyl-5-(4-(1-methyl-1H-pyrazol-4-yl)-1H-imidazol-1-yl)isoquinolin-1-yl)benzamide (93)

Compound (93) was obtained as a pale yellow solid (yield based on 6 steps: 19%) according to Example 66 using 3-(tert-butylamino)-4-cyanophenylboronic acid pinacol ester instead of 4-cyano-3-(ethylamino)phenylboronic acid pinacol ester.

Example 94

4-(8-(4-(1-Difluoromethyl-1H-pyrazol-4-yl)-1H-imidazol-1-yl)-2-(trifluoromethyl)quinolin-4-yl)-3-methylbenzamide (94)

Compound (94) was obtained as a pale yellow solid (yield based on 4 steps: 15%) according to Example 91 using 4-cyano-2-methylphenylboronic acid instead of 4-cyano-3-(ethylamino)phenylboronic acid pinacol ester.

Example 95

3-Methyl-4-(3-methyl-5-(4-(1-methyl-1H-pyrazol-4-yl)-1H-imidazol-1-yl)isoquinolin-1-yl)benzamide (95)

Compound (95) was obtained as a pale yellow solid (yield based on 6 steps: 22%) according to Example 66 using 4-cyano-2-methylphenylboronic acid instead of 4-cyano-3-(ethylamino)phenylboronic acid pinacol ester.

Example 96

2-(Tert-butylamino)-4-(5-(4-(1-methyl-1H-pyrazol-4-yl)-1H-imidazol-1-yl)isoquinolin-1-yl)benzamide (96)

Compound (96) was obtained as a pale yellow solid (yield based on 2 steps: 59%) according to Example 1(5) using 3-(tert-butylamino)-4-cyanophenylboronic acid pinacol ester instead of 4-cyano-3-(ethylamino)phenylboronic acid pinacol ester.

Example 97

2-(Tert-butylamino)-4-(2-methyl-8-(4-(1-methyl-1H-pyrazol-4-yl)-1H-imidazol-1-yl)quinolin-4-yl)benzamide (97)

8-Bromo-2-methylquinolin-4(1H)-one was obtained according to Example 3(1) using 2-bromoaniline instead of 2-iodoaniline and ethyl 3-oxobutanoate instead of ethyl 4,4,4-trifluoro-3-oxobutanoate. 4-Chloro-2-methyl-8-(4-(1-methyl-1H-pyrazol-4-yl)-1H-imidazol-1-yl)quinoline was obtained according to Example 3(2) using the obtained 8-bromo-2-methylquinolin-4(1H)-one instead of compound (3a). Compound (97) was obtained as a pale yellow solid (yield based on 5 steps: 9%) according to Example 3(3) using the obtained 4-chloro-2-methyl-8-(4-(1-methyl-1H-pyrazol-4-yl)-1H-imidazol-1-yl)quinoline instead of compound (3b) and 3-(tert-butylamino)-4-cyanophenylboronic acid pinacol ester instead of 4-cyano-3-(ethylamino)phenylboronic acid pinacol ester.

Example 98

2-(2-Methoxyethylamino)-4-(3-methyl-5-(4-(1-methyl-1H-pyrazol-4-yl)-1H-imidazol-1-yl)isoquinolin-1-yl)benzamide (98)

Compound (98) was obtained as a pale yellow solid (yield based on 5 steps: 3%) according to Example 97 using 4-cyano-3-(2-methoxyethylamino)phenylboronic acid pinacol ester instead of 3-(tert-butylamino)-4-cyanophenylboronic acid pinacol ester.

Example 99

2-(Tert-butylamino)-4-(8-(4-(6-methylpyridin-3-yl)-1H-imidazol-1-yl)-2-(trifluoromethyl)quinolin-4-yl)benzamide (99)

4-Chloro-8-(4-(6-methylpyridin-3-yl)-1H-imidazol-1-yl)-2-(trifluoromethyl)quinoline was obtained according to Example 3(2) using 5-(1H-imidazol-4-yl)-2-methylpyridine dihydrochloride instead of 4-(1H-imidazol-4-yl)-1-methyl-1H-pyrazole hydrochloride. Compound (99) was obtained as a pale yellow solid (yield based on 4 steps: 15%) according to Example 3(3) using the obtained 4-chloro-8-(4-(6-methylpyridin-3-yl)-1H-imidazol-1-yl)-2-(trifluoromethyl)quinoline instead of compound (3b) and 3-(tert-butylamino)-4-cyanophenylboronic acid pinacol ester instead of 4-cyano-3-(ethylamino)phenylboronic acid pinacol ester.

Example 100

3-Methyl-4-(8-(4-(6-methylpyridin-3-yl)-1H-imidazol-1-yl)-2-(trifluoromethyl)quinolin-4-yl)benzamide (100)

Compound (100) was obtained as a pale yellow solid (yield based on 4 steps: 14%) according to Example 99 using 4-cyano-2-methylphenylboronic acid instead of 3-(tert-butylamino)-4-cyanophenylboronic acid pinacol ester.

Example 101

2-Amino-4-(2-methyl-8-(4-(1-methyl-1H-pyrazol-4-yl)-1H-imidazol-1-yl)quinolin-4-yl)benzamide (101)

Compound (101) was obtained as a pale yellow solid (yield based on 5 steps: 4%) according to Example 97 using 3-amino-4-cyanophenylboronic acid pinacol ester instead of 3-(tert-butylamino)-4-cyanophenylboronic acid pinacol ester.

Example 102

3-Methyl-4-(2-methyl-8-(4-(1-methyl-1H-pyrazol-4-yl)-1H-imidazol-1-yl)quinolin-4-yl)benzamide (102)

Compound (102) was obtained as a pale yellow solid (yield based on 5 steps: 5%) according to Example 97 using 4-cyano-2-methylphenylboronic acid pinacol ester instead of 3-(tert-butylamino)-4-cyanophenylboronic acid pinacol ester.

Example 103

2-(Tert-butylamino)-4-(2-ethyl-8-(4-(1-methyl-1H-pyrazol-4-yl)-1H-imidazol-1-yl)quinolin-4-yl)benzamide (103)

8-Bromo-2-ethylquinolin-4(1H)-one was obtained according to Example 3(1) using 2-bromoaniline instead of 2-iodoaniline and ethyl 3-oxopentanoate instead of ethyl 4,4,4-trifluoro-3-oxobutanoate. 4-Chloro-2-ethyl-8-(4-(1-methyl-1H-pyrazol-4-yl)-1H-imidazol-1-yl)quinoline was obtained according to Example 3(2) using the obtained 8-bromo-2-ethylquinolin-4(1H)-one instead of compound (3a). Compound (103) was obtained as a pale yellow solid (yield based on 5 steps: 10) according to Example 3(3) using the obtained 4-chloro-2-ethyl-8-(4-(1-methyl-1H-pyrazol-4-yl)-1H-imidazol-1-yl)quinoline instead of compound (3b) and 3-(tert-butylamino)-4-cyanophenylboronic acid pinacol ester instead of 4-cyano-3-(ethylamino)phenylboronic acid pinacol ester.

Example 104

2-Amino-4-(2-ethyl-8-(4-(1-methyl-1H-pyrazol-4-yl)-1H-imidazol-1-yl)quinolin-4-yl)benzamide (104)

Compound (104) was obtained as a pale yellow solid (yield based on 5 steps: 1%) according to Example 103 using 3-amino-4-cyanophenylboronic acid pinacol ester instead of 3-(tert-butylamino)-4-cyanophenylboronic acid pinacol ester.

Example 105

2-(Tert-butylamino)-4-(2-cyclopropyl-8-(4-(1-methyl-1H-pyrazol-4-yl)-1H-imidazol-1-yl)quinolin-4-yl)benzamide (105)

8-Bromo-2-cyclopropylquinolin-4(1H)-one was obtained according to Example 3(1) using 2-bromoaniline instead of 2-iodoaniline and ethyl 3-cyclopropyl-3-oxopropanoate instead of ethyl 4,4,4-trifluoro-3-oxobutanoate. 4-Chloro-2-cyclopropyl-8-(4-(1-methyl-1H-pyrazol-4-yl)-1H-imidazol-1-yl)quinoline was obtained according to Example 3(2) using the obtained 8-bromo-2-cyclopropylquinolin-4(1H)-one instead of compound (3a). Compound (105) was obtained as a pale yellow solid (yield based on 5 steps: 0.4%) according to Example 3(3) using the obtained 4-chloro-2-cyclopropyl-8-(4-(1-methyl-1H-pyrazol-4-yl)-1H-imidazol-1-yl)quinoline instead of compound (3b) and 3-(tert-butylamino)-4-cyanophenylboronic acid pinacol ester instead of 4-cyano-3-(ethylamino)phenylboronic acid pinacol ester.

Example 106

2-Amino-4-(2-cyclopropyl-8-(4-(1-methyl-1H-pyrazol-4-yl)-1H-imidazol-1-yl)quinolin-4-yl)benzamide (106)

Compound (106) was obtained as a pale yellow solid (yield based on 5 steps: 0.3%) according to Example 105 using 3-amino-4-cyanophenylboronic acid pinacol ester instead of 3-(tert-butylamino)-4-cyanophenylboronic acid pinacol ester.

Example 107

2-(Tert-butylamino)-4-(8-(4-phenyl-1H-imidazol-1-yl)-2-(trifluoromethyl)quinolin-4-yl)benzamide (107)

4-Chloro-8-(4-phenyl-1H-imidazol-1-yl)-2-(trifluoromethyl)quinoline was obtained according to Example 3(2) using 4-phenyl-1H-imidazole instead of 4-(1H-imidazol-4-yl)-1-methyl-1H-pyrazole hydrochloride. Compound (107) was obtained as a pale yellow solid (yield based on 4 steps: 44%) according to Example 3(3) using the obtained 4-chloro-8-(4-phenyl-1H-imidazol-1-yl)-2-(trifluoromethyl)quinoline instead of compound (3b) and 3-(tert-butylamino)-4-

Example 108

2-Amino-4-(8-(4-phenyl-1H-imidazol-1-yl)-2-(trifluoromethyl)quinolin-4-yl)benzamide (108)

Compound (108) was obtained as a pale yellow solid (yield based on 4 steps: 30%) according to Example 107 using 3-amino-4-cyanophenylboronic acid pinacol ester instead of 3-(tert-butylamino)-4-cyanophenylboronic acid pinacol ester.

Example 109

2-(Isopropoxyethylamino)-4-(8-(4-phenyl-1H-imidazol-1-yl)-2-(trifluoromethyl)quinolin-4-yl)benzamide (109)

Compound (109) was obtained as a pale yellow solid (yield based on 4 steps: 40%) according to Example 107 using 4-cyano-3-(2-isopropoxyethylamino)phenylboronic acid pinacol ester instead of 3-(tert-butylamino)-4-cyanophenylboronic acid pinacol ester.

Example 110

2-Amino-4-(2'-(trifluoromethyl)-3,8'-biquinolin-4'-yl)benzamide (110)

Compound (110) was obtained as a pale yellow solid (yield based on 2 steps: 72%) according to Example 5(2) using 3-amino-4-cyanophenylboronic acid pinacol ester instead of 3-(tert-butylamino)-4-cyanophenylboronic acid pinacol ester.

Example 111

2-(2-Isopropoxyethylamino)-4-(2'-(trifluoromethyl)-3,8'-biquinolin-4'-yl)benzamide (111)

Compound (111) was obtained as a pale yellow solid (yield based on 2 steps: 42%) according to Example 5(2) using 4-cyano 3-(2-isopropoxyethylamino)phenylboronic acid pinacol ester instead of 3-(tert-butylamino)-4-cyanophenylboronic acid pinacol ester.

Example 112

2-(Tert-butylamino)-4-(2-isopropyl-8-(4-(1-methyl-1H-pyrazol-4-yl)-1H-imidazol-1-yl)quinolin-4-yl)benzamide (112)

8-bromo-2-isopropylquinolin-4(1H)-one was obtained according to Example 3(1) using ethyl 3-isopropyl-3-oxopropanoate instead of ethyl 4,4,4-trifluoro-3-oxobutanoate. 4-Chloro-2-isopropyl-8-(4-(1-methyl-1H-pyrazol-4-yl)-1H-imidazol-1-yl)quinoline was obtained according to Example 3(2) using the obtained 8-bromo-2-isopropylquinolin-4(1H)-one instead of compound (3a). Compound (112) was obtained as a pale yellow solid (yield based on 5 steps: 17%) according to Example 3(3) using the obtained 4-chloro-2-isopropyl-8-(4-(1-methyl-1H-pyrazol-4-yl)-1H-imidazol-1-yl)quinoline instead of compound (3b) and 3-(tert-butylamino)-4-cyanophenylboronic acid pinacol ester instead of 4-cyano-3-(ethylamino)phenylboronic acid pinacol ester.

Example 113

2-Amino-4-(2-isopropyl-8-(4-(1-methyl-1H-pyrazol-4-yl)-1H-imidazol-1-yl)quinolin-4-yl)benzamide (113)

Compound (113) was obtained as a pale yellow solid (yield based on 5 steps: 8%) according to Example 112 using 3-amino-4-cyanophenylboronic acid pinacol ester instead of 3-(tert-butylamino)-4-cyanophenylboronic acid pinacol ester.

Example 114

2-(4-Hydroxycyclohexylamino)-4-(8-(quinolin-3-yl)-2-(trifluoromethyl)quinazolin-4-yl)benzamide (114)

Example 114(1)

8-Chloro-2-(trifluoromethyl)quinazolin-4(1H)-one (114a)

Compound (114a) was obtained (yield based on 2 steps: 59%) according to Example 4(1) using 2-amino-3-chlorobenzoic acid instead of 2-amino-3-iodobenzoic acid.

Example 114(2)

2-(4-Hydroxycyclohexylamino)-4-(8-(quinolin-3-yl)-2-(trifluoromethyl)quinazolin-4-yl)benzamide (114)

A suspension of compound (114a) (0.57 g), 3-quinolineboronic acid (0.45 g), $Pd_2dba_3$ (0.031 g), X-Phos (0.064 g), and potassium phosphate (1.4 g) in butanol was stirred at 100° C. for 15 hours in a nitrogen atmosphere. After cooling, the reaction solution was partitioned between ethyl acetate and water. The organic layer was washed with brine and then dried over anhydrous sodium sulfate. The solvent was distilled off, and the residue was then purified by neutral silica gel column chromatography (chloroform/methanol) to obtain 8-(quinolin-3-yl)-2-(trifluoromethyl)quinazolin-4(1H)-one (0.49 g) as a white solid. Phosphorus oxychloride (5 ml) was added to the obtained 8-(quinolin-3-yl)-2-(trifluoromethyl)quinazolin-4(1H)-one (0.49 g), and the mixture was heated to reflux for 13 hours. The solvent was distilled off under reduced pressure, and ethyl acetate was added to the residue. The reaction solution was neutralized with an aqueous sodium bicarbonate solution with cooling in an ice bath and partitioned into organic and aqueous layers. The organic layer was washed with brine. The organic layer thus washed was dried over anhydrous sodium sulfate. Then, the solvent was distilled off, and the residue was purified by neutral silica gel column chromatography (chloroform/methanol) to obtain 4-chloro-8-(quinolin-3-yl)-2-(trifluoromethyl)quinazoline (0.43 g) as a white solid. Compound (114) was obtained as a yellow solid (yield based on 4 steps: 25%) according to Example 1(5) using the obtained 4-chloro-8-(quinolin-3-yl)-2-(trifluoromethyl)quinazoline instead of compound (1d) and 4-cyano-3-(4-hydroxycyclohexylamino)phenylboronic acid pinacol ester instead of 4-cyano-3-(ethylamino)phenylboronic acid pinacol ester.

Example 115

4-(2-Cyclopropyl-8-(quinolin-3-yl)quinazolin-4-yl)-2-(4-hydroxycyclohexylamino)benzamide (115)

EDCI hydrochloride (22.0 g) and 1-hydroxybenzotriazole (11.4 g) were added to a solution of 2-amino-3-chlorobenzoic acid (12.8 g) in DMF (100 mL), and subsequently ammonia water (22.0 ml) was added thereto. The reaction solution was stirred at room temperature for 3 hours. Water was added to the reaction solution, and the deposit was filtrated and dried under reduced pressure to obtain 2-amino-3-chlorobenzamide (9.7 g). Iron(III) chloride hexahydrate (6.3 g) and cyclopropanecarbaldehyde (1.3 ml) were added to a suspension of the obtained 2-amino-3-chlorobenzamide (2.0 g) in water (30 ml), and the mixture was stirred overnight at 100° C. After cooling, water was added to the reaction solution, and the deposit was filtrated and dried under reduced pressure to obtain 8-chloro-2-cyclopropylquinazolin-4(1H)-one (2.0 g). Compound (115) was obtained as a yellow solid (yield based on 6 steps: 18%) according to Example 114(2) using the obtained 8-chloro-2-cyclopropylquinazolin-4(1H)-one instead of compound (114a).

Example 116

4-(2-Ethyl-8-(quinolin-3-yl)quinazolin-4-yl)-2-(4-hydroxycyclohexylamino)benzamide (116)

Compound (116) was obtained as a pale yellow solid (yield based on 6 steps: 13%) according to Example 115 using propionaldehyde instead of cyclopropanecarbaldehyde.

Example 117

4-(3,8'-Biquinolin-4'-yl)-2-(4-hydroxycyclohexylamino)benzamide (117)

A suspension of 2-bromoaniline (20.9 g) and 5-(methoxymethylene)-2,2-dimethyl-1,3-dioxane-4,6-dione (22.6 g) in 2-propanol (240 ml) was heated to reflux for 1 hour. The reaction solution was cooled to 0° C., and the deposit was then filtrated to obtain a pale yellow solid (35.0 g). A suspension of the obtained pale yellow solid (10.0 g) in Dowtherm (100 ml) was heated at 210° C. for 1 hour. After cooling, hexane (100 ml) was added to the reaction solution, and the deposit was filtrated to obtain 8-bromoquinolin-4(1H)-one (6.3 g). Phosphorus oxychloride (5.9 ml) was added to 8-bromoquinolin-4(1H)-one (9 g), and the mixture was heated to reflux for 2 hours. The solvent was distilled off under reduced pressure, and chloroform was added to the residue. The reaction solution was neutralized with an aqueous sodium hydroxide solution with cooling in an ice bath and partitioned into organic and aqueous layers. The organic layer was washed with brine. The organic layer thus washed was dried over anhydrous sodium sulfate. Then, the solvent was distilled off, and the residue was purified by neutral silica gel column chromatography (chloroform/methanol) to obtain 8-bromo-4-chloroquinoline (8.3 g) as a white solid.

Pd(PPh$_3$)$_4$ (0.0581 g) was added to a solution of the obtained 8-bromo-4-chloroquinoline (0.242 g), 3-quinolineboronic acid (0.163 g), and an aqueous sodium carbonate solution (2 M, 1.5 mL) in ethylene glycol dimethyl ether (3.0 mL) in a nitrogen atmosphere, and the mixture was stirred at 85° C. for 3 hours. The reaction solution was partitioned between ethyl acetate and water. The organic layer was washed with brine and then dried over anhydrous sodium sulfate. The solvent was distilled off, and the residue was purified by neutral silica gel column chromatography (chloroform/methanol) to obtain 4'-chloro-3,8'-biquinoline (0.114 g) as a white solid. Compound (117) was obtained as a pale yellow solid (yield based on 6 steps: 37%) according to Example 3(3) using the obtained 4'-chloro-3,8'-biquinoline instead of compound (3b) and 4-cyano-3-(4-hydroxycyclohexylamino)phenylboronic acid pinacol ester instead of 4-cyano-3-(ethylamino)phenylboronic acid pinacol ester.

Example 118

2-Amino-4-(8-(4-(6-methylpyridin-3-yl)-1H-imidazol-1-yl)-2-(trifluoromethyl)quinolin-4-yl)benzamide (118)

Compound (118) was obtained as a pale yellow solid (yield based on 4 steps: 150) according to Example 99 using 3-amino-4-cyanophenylboronic acid pinacol ester instead of 3-(tert-butylamino)-4-cyanophenylboronic acid pinacol ester.

Example 119

2-(Ethylamino)-4-(4-(4-(1-methyl-1H-pyrazol-4-yl)-1H-imidazol-1-yl)quinolin-8-yl)benzamide (119)

A suspension of 2-bromoaniline (20.9 g) and 5-(methoxymethylene)-2,2-dimethyl-1,3-dioxane-4,6-dione (22.6 g) in 2-propanol (240 ml) was heated to reflux for 1 hour. The reaction solution was cooled to 0° C., and the deposit was then filtrated to obtain a pale yellow solid (35.0 g). A suspension of the obtained pale yellow solid (10.0 g) in Dowtherm (100 ml) was heated at 210° C. for 1 hour. After cooling, hexane (100 ml) was added to the reaction solution, and the deposit was filtrated to obtain 8-bromoquinolin-4(1H)-one (6.3 g). Thionyl chloride (5.9 ml) was added to 8-bromoquinolin-4(1H)-one (9.0 g), and the mixture was heated to reflux for 2 hours. The solvent was distilled off under reduced pressure, and chloroform was added to the residue. The reaction solution was neutralized with an aqueous sodium hydroxide solution with cooling in an ice bath and partitioned into organic and aqueous layers. The organic layer was washed with brine. The organic layer thus washed was dried over anhydrous sodium sulfate. Then, the solvent was distilled off, and the residue was purified by neutral silica gel column chromatography (chloroform/methanol) to obtain 8-bromo-4-chloroquinoline (8.3 g) as a white solid. The obtained 8-bromo-4-chloroquinoline (0.050 g), 4-(1H-imidazol-4-yl)-1-methyl-1H-pyrazole hydrochloride (0.045 g), 8-quinolinol (0.0045 g), copper(I) oxide (0.0015 g), PEG (Mn=3400) (0.010 g), and cesium carbonate (0.17 g) were suspended in DMSO (2.1 ml). The suspension was purged with nitrogen, then sealed in the tube, and stirred at 110° C. for 2 hours. After cooling, the reaction solution was partitioned between ethyl acetate and water. The organic layer was washed with brine and then dried over anhydrous sodium sulfate to obtain 8-bromo-4-(4-(1-methyl-1H-pyrazol-4-yl)-1H-imidazol-1-yl)quinoline as a pale yellow solid (0.073 g). Compound (119) was obtained as a pale yellow solid (yield based on 6 steps: 17%) according to Example 1(5) using the obtained 8-bromo-4-(4-(1-methyl-1H-pyrazol-4-yl)-1H-imidazol-1-yl)quinoline instead of compound (1d).

Example 120

2-Amino-4-(2'-ethyl-3,8'-biquinolin-4'-yl)benzamide (120)

8-Bromo-2-ethylquinolin-4(1H)-one was obtained according to Example 3(1) using 2-bromoaniline instead of 2-iodoaniline and ethyl 3-oxopentanoate instead of ethyl 4,4,4-trifluoro-3-oxobutanoate. 4'-Chloro-4'-ethyl-3,8'-biquinoline was obtained according to Example 5(1) using the obtained 8-bromo-2-ethylquinolin-4(1H)-one instead of compound (3a). Compound (120) was obtained as a pale yellow solid (yield based on 5 steps: 3%) according to Example 3(3) using the obtained 4'-chloro-4'-ethyl-3,8'-biquinoline instead of compound (3b) and 3-amino-4-cyanophenylboronic acid pinacol ester instead of 4-cyano-3-(ethylamino)phenylboronic acid pinacol ester.

Example 121

2-Amino-4-(2'-isopropyl-3,8'-biquinolin-4'-yl)benzamide (121)

Compound (121) was obtained as a pale yellow solid (yield based on 5 steps: 14%) according to Example 120 using methyl 3-isopropyl-3-oxopropanoate instead of ethyl 3-oxopentanoate.

Example 122

2-Amino-4-(2-ethyl-8-(4-(pyridin-3-yl)-1H-imidazol-1-yl)quinolin-4-yl)benzamide (122)

Compound (122) was obtained as a pale yellow solid (yield based on 5 steps: 3%) according to Example 103 using 5-(1H-imidazol-4-yl)pyridine dihydrochloride instead of 4-(1H-imidazol-4-yl)-1-methyl-1H-pyrazole hydrochloride and 3-amino-4-cyanophenylboronic acid pinacol ester instead of 3-(tert-butylamino)-4-cyanophenylboronic acid pinacol ester.

Example 123

2-Amino-4-(2-isopropyl-8-(4-(pyridin-3-yl)-1H-imidazol-1-yl)quinolin-4-yl)benzamide (123)

Compound (123) was obtained as a pale yellow solid (yield based on 5 steps: 5%) according to Example 112 using 5-(1H-imidazol-4-yl)pyridin 2 hydrochloride instead of 4-(1H-imidazol-4-yl)-1-methyl-1H-pyrazol hydrochloride and 3-amino-4-cyanophenylboronic acid pinacol ester instead of 3-(tert-butylamino)-4-cyanophenylboronic acid pinacol ester.

Example 124

2-Amino-4-(2-ethyl-8-(4-(6-methylpyridin-3-yl)-1H-imidazol-1-yl)quinolin-4-yl)benzamide (124)

Compound (124) was obtained as a pale yellow solid (yield based on 5 steps: 2%) according to Example 103 using 5-(1H-imidazol-4-yl)-2-methylpyridin 2 hydrochloride instead of 4-(1H-imidazol-4-yl)-1-methyl-1H-pyrazol hydrochloride and 3-amino-4-cyanophenylboronic acid pinacol ester instead of 3-(tert-butylamino)-4-cyanophenylboronic acid pinacol ester.

Example 125

2-Amino-4-(2-isopropyl-8-(4-(6-methylpyridin-3-yl)-1H-imidazol-1-yl)quinolin-4-yl)benzamide (125)

Compound (125) was obtained as a pale yellow solid (yield based on 5 steps: 4%) according to Example 112 using 5-(1H-imidazol-4-yl)-2-methylpyridin 2 hydrochloride instead of 4-(1H-imidazol-4-yl)-1-methyl-1H-pyrazol hydrochloride and 3-amino-4-cyanophenylboronic acid pinacol ester instead of 3-(tert-butylamino)-4-cyanophenylboronic acid pinacol ester.

Example 126

2-(Tert-butylamino)-4-(5-(quinolin-3-yl)isoquinolin-1-yl)benzamide (126)

Compound (126) was obtained as a white solid (yield based on 3 steps: 40%) according to Example 6 using 3-(tert-butylamino)-4-cyanophenylboronic acid pinacol ester instead of 4-cyano-3-(4-hydroxycyclohexylamino)phenylboronic acid pinacol ester.

Example 127

2-(Tert-butylamino)-4-(5-(4-pyridin-3-yl)-1H-imidazol-1-yl)isoquinolin-1-yl)benzamide (127)

Compound (127) was obtained as a pale yellow solid (yield based on 5 steps: 18%) according to Example 32 using 3-(tert-butylamino)-4-cyanophenylboronic acid pinacol ester instead of 4-cyano-3-(4-hydroxycyclohexylamino)phenylboronic acid pinacol ester.

Example 128

2-Amino-4-(5-(4-(1-methyl-1H-pyrazol-4-yl)-1H-imidazol-1-yl)isoquinolin-1-yl)benzamide (128)

Compound (128) was obtained as a pale yellow solid (yield based on 2 steps: 560) according to Example 1(5) using 3-amino-4-cyanophenylboronic acid pinacol ester instead of 4-cyano-3-(ethylamino)phenylboronic acid pinacol ester.

Example 129

3-(1-(4-(3-Amino-4-carbamoylphenyl)-2-isopropylquinolin-8-yl)-1H-pyrazol-4-yl)pyridine 1-oxide (129)

8-Bromo-2-isopropylquinolin-4(1H)-one was obtained according to Example 3(1) using 2-bromoaniline instead of 2-iodoaniline and methyl 3-isopropyl-3-oxopropanoate instead of ethyl 3-oxopentanoate. 4-Chloro-2-isopropyl-8-(4-(pyridin-3-yl)-1H-imidazol-1-yl)quinoline was obtained according to Example 3(2) using the obtained 8-bromo-2-isopropylquinolin-4(1H)-one instead of compound (3a) and 5-(1H-imidazol-4-yl)pyridine dihydrochloride instead of 4-(1H-imidazol-4-yl)-1-methyl-1H-pyrazole hydrochloride. 3-(1-(4-Chloro-2-isopropylquinolin-8-yl)-1H-imidazol-4-yl)pyridine 1-oxide was obtained according to Example 1(1) using the obtained 4-chloro-2-isopropyl-8-(4-(pyridin-3-yl)-1H-imidazol-1-yl)quinoline instead of 5-bromoisoquinoline. Compound (129) was obtained (yield based on 5 steps: 1.5%) according to Example 2(1) using the obtained 3-(1-(4-chloro-2-isopropylquinolin-8-yl)-1H-imidazol-4-yl)pyridine 1-oxide instead of compound (1b) and 3-amino-4-carbamoylphenylboronic acid hydrochloride instead of 4-cyano-3-(4-hydroxycyclohexylamino)phenylboronic acid pinacol ester.

Example 130

2-(Tert-butylamino)-4-(8-(4-(1-methyl-1H-pyrazol-4-yl)-1H-imidazol-1-yl)quinolin-4-yl)benzamide (130)

A suspension of 2-bromoaniline (20.9 g) and 5-(methoxymethylene)-2,2-dimethyl-1,3-dioxane-4,6-dione (22.6 g) in isopropanol (240 ml) was heated to reflux for 1 hour. After cooling, the deposit was filtrated to obtain 5-((2-bromophenylamino)methylene)-2,2-dimethyl-1,3-dioxane-4,6-dione (34.8 g). A suspension of the obtained 5-((2-bromophenylamino)methylene)-2,2-dimethyl-1,3-dioxane-4,6-dione (10.8 g) in Dowtherm (100 ml) was heated at 210° C. for 1 hour. After cooling, hexane (100 ml) was added to the reaction solution. The deposit was filtrated to obtain 8-bromoquinolin-4(1H)-one (6.3 g). 4-Chloro-8-(4-(1-methyl-1H-pyrazol-4-yl)-1H-imidazol-1-yl)quinoline was obtained according to Example 3(2) using the obtained 8-bromoquinolin-4(1H)-one instead of compound (3a). Compound (130) was obtained as a pale yellow solid (yield based on 6 steps: 3.4%) according to Example 3(3) using 3-(tert-butylamino)-4-cyanophenylboronic acid pinacol ester instead of 4-cyano-3-(ethylamino)phenylboronic acid pinacol ester.

Example 131

2-(Tert-butylamino)-4-(8-(4-(pyridin-3-yl)-1H-imidazol-1-yl)quinolin-4-yl)benzamide (131)

Compound (131) was obtained as a pale yellow solid (yield based on 6 steps: 8.0%) according to Example 130 using 5-(1H-imidazol-4-yl)pyridine dihydrochloride instead of 4-(1H-imidazol-4-yl)-1-methyl-1H-pyrazole hydrochloride.

Example 132

2-Amino-4-(8-(4-(1-methyl-1H-pyrazol-4-yl)-1H-imidazol-1-yl)quinolin-4-yl)benzamide (132)

Compound (132) was obtained as a pale yellow solid (yield based on 6 steps: 2.2%) according to Example 130 using 3-amino-4-cyanophenylboronic acid pinacol ester instead of 3-(tert-butylamino)-4-cyanophenylboronic acid pinacol ester.

Example 133

2-(Tert-butylamino)-4-(8-(4-(pyridin-3-yl)-1H-imidazol-1-yl)quinolin-4-yl)benzamide (133)

Compound (133) was obtained as a pale yellow solid (yield based on 6 steps: 7.3%) according to Example 131 using 3-amino-4-cyanophenylboronic acid pinacol ester instead of 3-(tert-butylamino)-4-cyanophenylboronic acid pinacol ester.

Comparative Example 1

2-(4-Hydroxycyclohexylamino)-4-(1-(quinolin-3-yl)isoquinolin-5-yl)benzamide 3-(5-Bromoisoquinolin-1-yl)quinoline was obtained according to Example 2(1) using 3-quinolineboronic acid instead of 4-cyano-3-(4-hydroxycyclohexylamino)phenylboronic acid pinacol ester. A compound of Comparative Example 1 was obtained as a pale yellow solid (yield based on 3 steps: 24%) according to Example 2(3) using the obtained 3-(5-bromoisoquinolin-1-yl)quinoline instead of compound (2b) and 4-cyano-3-(4-hydroxycyclohexylamino)phenylboronic acid pinacol ester instead of 4-cyano-3-(ethylamino)phenylboronic acid pinacol ester.

Comparative Example 2

2-(4-Hydroxycyclohexylamino)-4-(4-(quinolin-3-yl)quinazolin-8-yl)benzamide

Tosylic acid dihydrate (0.038 g) was added to a suspension of 2-amino-3-iodobenzamide (0.513 g) supplemented with methyl orthoformate (5 ml) and NMP (1 ml), and the mixture was heated to reflux for 3 hours. After cooling, water was added to the reaction solution, and the deposit was filtrated and dried under reduced pressure to obtain 8-iodoquinazolin-4(1H)-one (0.481 g). Phosphorus oxychloride (10 ml) was added to the obtained 8-iodoquinazolin-4(1H)-one (1.17 g), and the mixture was heated to reflux for 8 hours. The solvent was distilled off under reduced pressure, and chloroform was added to the residue. The reaction solution was neutralized with an aqueous sodium hydroxide solution with cooling in an ice bath and partitioned into organic and aqueous layers. The organic layer was washed with brine. The organic layer thus washed was dried over anhydrous sodium sulfate. Then, the solvent was distilled off, and the residue was purified by neutral silica gel column chromatography (chloroform/ethyl acetate) to obtain 4-chloro-8-iodoquinazoline (0.946 g). 4-(4-Chloroquinazolin-8-yl)-2-(4-hydroxycyclohexylamino)benzonitrile was obtained according to Example 2(1) using the obtained 4-chloro-8-iodoquinazoline instead of compound (1b) and $PdCl_2dppf$ instead of $Pd(PPh_3)_4$. A compound of Comparative Example 2 was obtained as a pale yellow solid (yield based on 5 steps: 10%) according to Example 79 using the obtained 4-(4-chloroquinazolin-8-yl)-2-(4-hydroxycyclohexylamino)benzonitrile instead of compound (4b) and 3-quinolineboronic acid instead of 3-(tert-butylamino)-4-cyanophenylboronic acid pinacol ester.

Comparative Example 3

2-(Ethylamino)-4-(1-(4-(1-methyl-1H-pyrazol-4-yl)-1H-imidazol-1-yl)isoquinolin-5-yl)benzamide Compound (1b) (0.050 g), 4-(1H-imidazol-4-yl)-1-methyl-1H-pyrazole hydrochloride (0.045 g), 8-quinolinol (0.0045 g), copper(I) oxide (0.0015 g), PEG (Mn=3400) (0.010 g), and cesium carbonate (0.17 g) were suspended in DMSO (2.1 ml). The suspension was purged with nitrogen, then sealed in the tube, and stirred at 110° C. for 2 hours. After cooling, the reaction solution was partitioned between ethyl acetate and water. The organic layer was washed with brine and then dried over anhydrous sodium sulfate to obtain a pale yellow solid (0.073 g). A compound of Comparative Example 3 was obtained as a pale yellow solid (0.035 g, yield based on 3 steps: 39%) according to Example 1(5) using the obtained pale yellow solid (0.073 g) instead of compound (1d).

The structural formulas and physical properties of the compounds synthesized in Examples and Comparative Examples above are shown in the following tables:

TABLE 1

| Cpd No. | Structural formula | Physical property |
|---|---|---|
| 1 | (structure) | ¹H-NMR (DMSO-d₆): δ 8.65 (1H, d, J = 5.9 Hz), 8.15-8.22 (2H, m), 7.9-8.15 (4H, m), 7.73-7.82 (4H, m), 7.52 (1H, d, J = 6.1 Hz), 7.27 (1H, brs), 6.88 (1H, s), 6.79 (1H, d, J = 8.9 Hz), 3.87 (3H, s), 3.05-3.25 (2H, m), 1.20 (3H, t, J = 7.1 Hz); LRMS (ESI) m/z 438 [M + H]⁺. |
| 2 | (structure) | ¹H-NMR (DMSO-d₆): δ 8.57 (1H, d, J = 5.9 Hz), 8.30 (1H, d, J = 7.6 Hz), 8.03-8.09 (2H, m), 7.93 (1H, brs), 7.66-7.80 (5H, m), 7.23 (1H, brs), 7.04 (1H, s), 6.91 (1H, s), 6.73 (1H, d, J = 8.1 Hz), 5.53 (2H, s), 4.50 (1H, d, J = 4.1 Hz), 3.92 (3H, s), 3.30-3.60 (2H, m), 1.75-2.05 (4H, m), 1.10-1.35 (4H, m); LRMS (ESI) m/z 454 [M + H]⁺. |
| 3 | (structure) | ¹H-NMR (DMSO-d₆): δ 8.20-8.31 (2H, m), 8.11 (1H, d, J = 7.3 Hz), 7.80-8.11 (7H, m), 7.73 (1H, s), 7.32 (1H, brs), 6.85 (1H, s), 6.74 (1H, d, J = 7.9 Hz), 3.88 (3H, s), 3.10-3.50 (2H, m), 1.20 (3H, t, J = 7.1 Hz); LRMS (ESI) m/z 506 [M + H]⁺. |

TABLE 1-continued
| Cpd No. | Structural formula | Physical property |
|---|---|---|
| 4 | 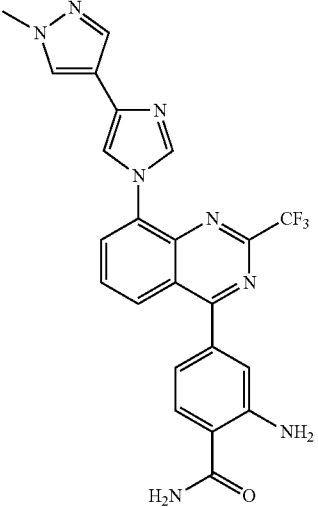 | $^1$H-NMR (DMSO-$d_6$): δ 8.36 (1H, d, J = 7.3 Hz), 8.33 (1H, s), 8.26 (1H, d, J = 8.5 Hz), 8.05 (1H, t, J = 8.1 Hz), 7.90-8.00 (3H, m), 7.79 (1H, d, J = 7.8 Hz), 7.73 (1H, s), 7.31 (1H, brs), 7.18 (1H, s), 6.85-6.95 (3H, m), 3.88 (3H, s); LRMS (ESI) m/z 479 [M + H]$^+$. |
| 5 | 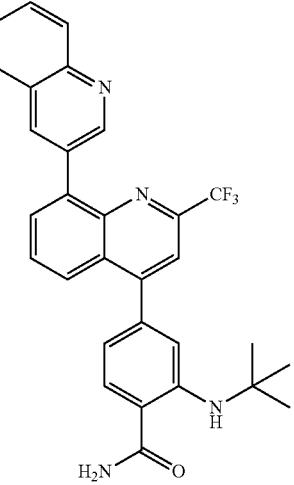 | $^1$H-NMR (DMSO-$d_6$): δ 9.28 (1H, s), 8.66 (1H, s), 8.58 (1H, s), 8.20 (1H, d, J = 7.1 Hz), 7.76-8.15 (8H, m), 7.68 (1H, t, J = 7.4 Hz), 7.31 (1H, brs), 7.01 (1H, s), 6.75 (1H, d, J = 7.8 Hz), 1.35 (9H, s); LRMS (ESI) m/z 515 [M + H]$^+$. |
TABLE 2
| 6 | 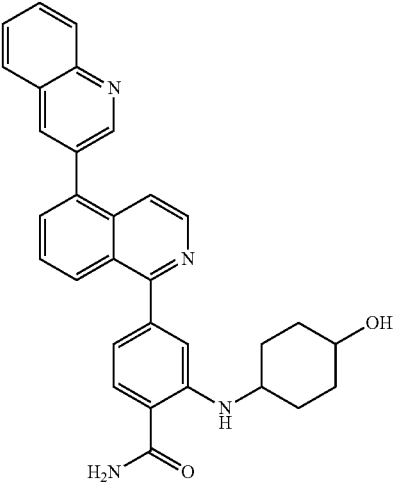 | $^1$H-NMR (DMSO-$d_6$): δ 9.07 (1H, d, J = 2.2 Hz), 8.58-8.62 (2H, m), 7.70-8.40 (11H, m), 7.25 (1H, brs), 6.94 (1H, s), 6.77 (1H, d, J = 8.5 Hz), 4.51 (1H, d, J = 4.2 Hz), 3.30-3.60 (2H, m), 1.75-2.05 (4H, m), 1.20-1.35 (4H, m); LRMS (ESI) m/z 489 [M + H]$^+$. |

TABLE 2-continued
7 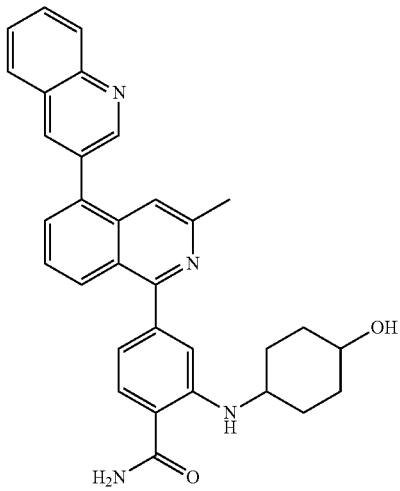 [SMILES: Cc1cc2c(-c3cnc4ccccc4c3)cccc2c(-c2ccc(C(N)=O)c(NC3CCC(O)CC3)c2)n1]
¹H-NMR (DMSO-d₆): δ 9.05 (1H, d, J = 2.2 Hz), 8.56 (1H, d, J = 2.2 Hz), 7.64-8.35 (10H, m), 7.52 (1H, s), 7.25 (1H, brs), 6.90 (1H, s), 6.74 (1H, d, J = 7.8 Hz), 4.52 (1H, d, J = 4.4 Hz), 3.30-3.60 (2H, m), 2.59 (3H, s), 1.75-2.05 (4H, m), 1.20-1.35 (4H, m); LRMS (ESI) m/z 503 [M + H]⁺.
8 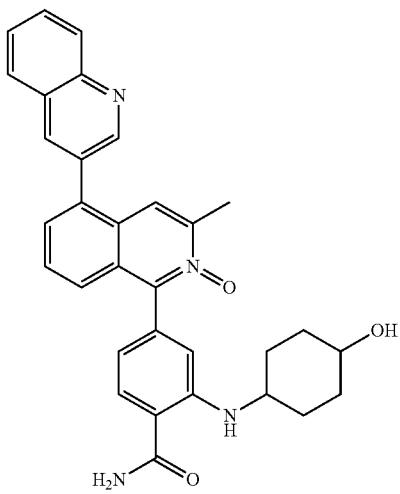 [SMILES: Cc1cc2c(-c3cnc4ccccc4c3)cccc2c(-c2ccc(C(N)=O)c(NC3CCC(O)CC3)c2)[n+]1[O-]]
¹H-NMR (DMSO-d₆): δ 9.04 (1H, d, J = 2.2 Hz), 8.55 (1H, s), 8.28 (1H, d, J = 7.8 Hz), 8.15 (1H, t, J = 8.6 Hz), 7.60-8.05 (7H, m), 7.39 (1H, d, J = 7.1 Hz), 7.25 (1H, brs), 6.77 (1H, s), 6.53 (1H, d, J = 8.3 Hz), 4.51 (1H, d, J = 4.4 Hz), 3.30-3.60 (2H, m), 2.50 (3H, s), 1.75-2.05 (4H, m), 1.20-1.35 (4H, m); LRMS (ESI) m/z 519 [M+H]⁺.
9 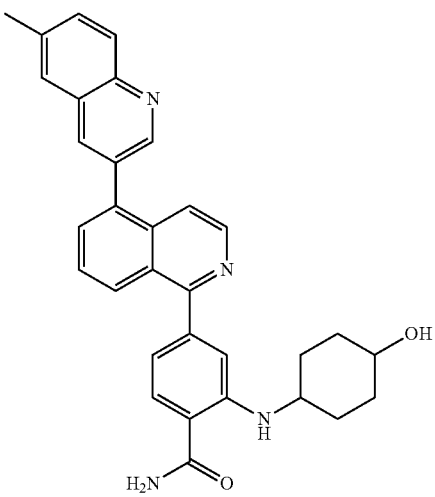 [SMILES: Cc1ccc2ncc(-c3cccc4c(-c5ccc(C(N)=O)c(NC6CCC(O)CC6)c5)nccc34)cc2c1]
¹H-NMR (DMSO-d₆): δ 8.98 (1H, d, J = 2.2 Hz), 8.58 (1H, d, J = 5.8 Hz), 8.46 (1H, d, J = 1.9 Hz), 8.32 (1H, d, J = 7.6 Hz), 8.14 (1H, d, J = 8.5 Hz), 8.05 (1H, d, J = 8.5 Hz), 7.86-7.99 (3H, m), 7.69-7.81 (4H, m), 7.24 (1H, brs), 6.93 (1H, s), 6.76 (1H, d, J = 8.1 Hz), 4.51 (1H, d, J = 4.2 Hz), 3.30-3.60 (2H, m), 2.57 (3H, s), 1.75-2.05 (4H, m), 1.20-1.35 (4H, m); LRMS (ESI) m/z 503 [M + H]⁺.

TABLE 2-continued
| 10 | 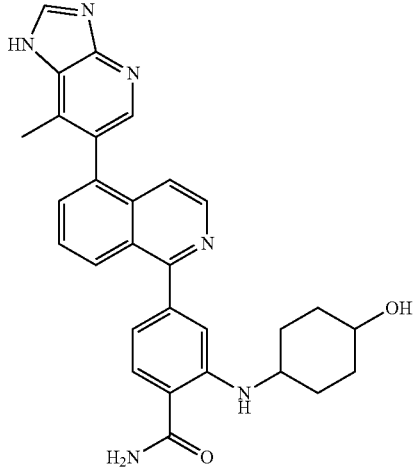 [SMILES: Cc1c(-c2cccc3c(-c4ccc(C(N)=O)c(NC5CCC(O)CC5)c4)nccc23)cnc2nc[nH]c12] | ¹H-NMR (DMSO-d₆): δ 8.45-8.60 (2H, m), 8.10-8.35 (3H, m), 7.98 (1H, brs), 7.70-7.83 (3H, m), 7.18-7.30 (2H, m), 6.95 (1H, s), 6.76 (1H, d, J = 8.3 Hz), 4.51 (1H, d, J = 3.7 Hz), 3.30-3.60 (2H, m), 2.30 (3H, s), 1.75-2.05 (4H, m), 1.20-1.35 (4H, m); LRMS (ESI) m/z 493 [M + H]⁺. |
TABLE 3
| 11 | 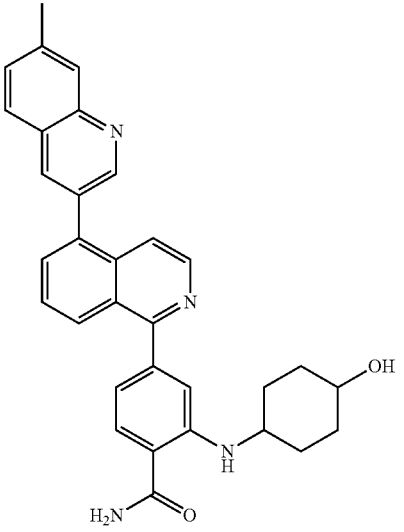 [SMILES: Cc1ccc2cc(-c3cccc4c(-c5ccc(C(N)=O)c(NC6CCC(O)CC6)c5)nccc34)cnc2c1] | ¹H-NMR (DMSO-d₆): δ 9.01 (1H, d, J = 2.2 Hz), 8.59 (1H, d, J = 5.9 Hz), 8.52 (1H, s), 8.32 (1H, d, J = 8.0 Hz), 8.13 (1H, d, J = 8.3 Hz), 8.02 (1H, d, J = 8.3 Hz), 7.90-7.99 (3H, m), 7.75-7.82 (2H, m), 7.70 (1H, d, J = 6.3 Hz), 7.57 (1H, d, J = 9.0 Hz), 7.23 (1H, brs), 6.93 (1H, s), 6.76 (1H, d, J = 8.1 Hz), 4.51 (1H, d, J = 4.2 Hz), 3.30-3.60 (2H, m), 2.60 (3H, s), 1.75-2.05 (4H, m), 1.20-1.35 (4H, m); LRMS (ESI) m/z 503 [M + H]⁺. |
| 12 | 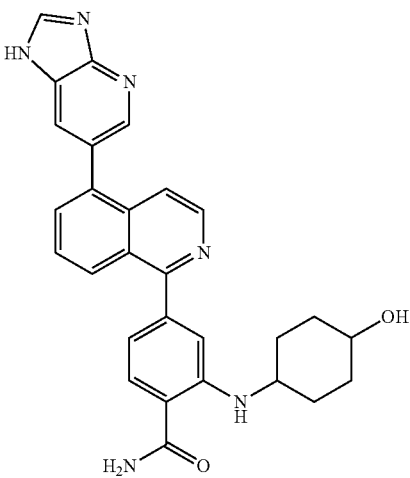 [SMILES: NC(=O)c1ccc(-c2nccc3c(-c4cnc5nc[nH]c5c4)cccc23)cc1NC1CCC(O)CC1] | ¹H-NMR (DMSO-d₆): δ 8.41-8.61 (3H, m), 8.10-8.35 (3H, m), 7.98 (1H, brs), 7.70-7.85 (4H, m), 7.32 (1H, brs), 6.92 (1H, s), 6.75 (1H, d, J = 8.2 Hz), 4.51 (1H, d, J = 4.1 Hz), 3.30-3.60 (2H, m), 1.75-2.05 (4H, m), 1.20-1.35 (4H, m); LRMS (ESI) m/z 479 [M + H]⁺. |

TABLE 3-continued

| | | |
|---|---|---|
| 13 | (structure) | ¹H-NMR (DMSO-d₆): δ 9.36 (1H, d, J = 2.4 Hz), 9.25 (1H, s), 9.19 (1H, s), 8.76 (1H, d, J = 2.4 Hz), 8.61 (1H, d, J = 5.9 Hz), 8.30-8.35 (1H, m), 8.19 (1H, d, J = 8.8 Hz), 8.02 (1H, d, J = 7.1 Hz), 7.95 (1H, brs), 7.72-7.85 (3H, m), 7.23 (1H, brs), 6.93 (1H, s), 6.77 (1H, d, J = 7.8 Hz), 4.51 (1H, d, J = 4.2 Hz), 3.30-3.60 (2H, m), 1.75-2.05 (4H, m), 1.20-1.35 (4H, m); LRMS (ESI) m/z 491 [M + H]⁺. |
| 14 | (structure) | ¹H-NMR (DMSO-d₆): δ 11.87 (1H, s), 8.56 (1H, d, J = 6.1 Hz), 8.34 (1H, d, J = 1.9 Hz), 8.32 (1H, d, J = 7.8 Hz), 8.12 (1H, d, J = 1.9 Hz), 8.07 (1H, d, J = 7.8 Hz), 7.94 (1H, brs), 7.68-7.85 (4H, m), 7.61 (1H, t, J = 2.9 Hz), 7.23 (1H, brs), 6.93 (1H, s), 6.76 (1H, d, J = 8.0 Hz), 6.55-6.60 (1H, m), 4.51 (1H, d, J = 4.4 Hz), 3.30-3.60 (2H, m), 1.75-2.05 (4H, m), 1.20-1.35 (4H, m); LRMS (ESI) m/z 478 [M + H]⁺. |
| 15 | (structure) | ¹H-NMR (DMSO-d₆): δ 8.70-8.80 (2H, m), 8.58 (1H, dd, J = 5.9, 1.7 Hz), 8.29-8.33 (1H, m), 8.11 (1H, d, J = 8.3 Hz), 7.85-8.03 (2H, m), 7.70-7.83 (3H, m), 7.59-7.65 (2H, m), 7.23 (1H, brs), 6.91 (1H, s), 6.74 (1H, d, J = 8.0 Hz), 4.51 (1H, d, J = 3.9 Hz), 3.30-3.60 (2H, m), 1.75-2.05 (4H, m), 1.10-1.35 (4H, m); LRMS (ESI) m/z 439 [M + H]⁺. |

TABLE 4
| 16 | 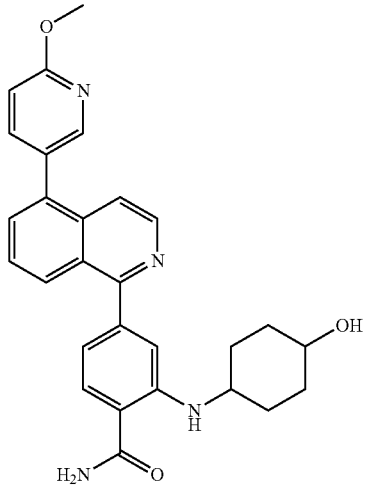 [SMILES: COc1ccc(-c2cccc3c(-c4ccc(C(N)=O)c(NC5CCC(O)CC5)c4)nccc23)cn1] | $^1$H-NMR (DMSO-d$_6$): δ 8.52 (1H, d, J = 5.8 Hz), 8.36 (1H, d, J = 3.6 Hz), 8.31 (1H, d, J = 7.3 Hz), 8.07 (1H, t, J = 4.2 Hz), 7.93 (1H, brs), 7.65-7.80 (4H, m), 7.18-7.35 (3H, m), 6.91 (1H, s), 6.74 (1H, d, J = 8.0 Hz), 4.51 (1H, d, J = 3.9 Hz), 3.48 (3H, s), 3.30-3.60 (2H, m), 1.75-2.05 (4H, m), 1.10-1.35 (4H, m); LRMS (ESI) m/z 469 [M + H]$^+$. |
| --- | --- | --- |
| 17 | 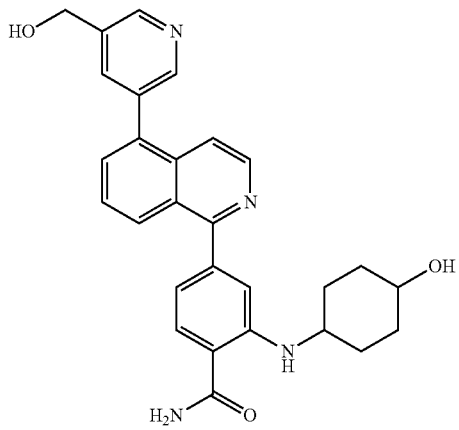 [SMILES: NC(=O)c1ccc(-c2nccc3c(-c4cncc(CO)c4)cccc23)cc1NC1CCC(O)CC1] | $^1$H-NMR (DMSO-d$_6$): δ 8.67 (1H, s), 8.61 (1H, s), 8.59 (1H, d, J = 6.1 Hz), 8.28-8.35 (1H, m), 8.10 (1H, d, J = 8.6 Hz), 7.89-8.00 (2H, m), 7.70-7.80 (3H, m), 7.63 (1H, d, J = 5.9 Hz), 7.22 (1H, brs), 6.91 (1H, s), 6.74 (1H, d, J = 8.1 Hz), 5.45 (1H, t, J = 5.9 Hz), 4.68 (1H, d, J = 5.8 Hz), 4.51 (1H, d, J = 4.2 Hz), 3.30-3.60 (2H, m), 1.75-2.05 (4H, m), 1.10-1.35 (4H, m); LRMS (ESI) m/z 469 [M + H]$^+$. |
| 18 | 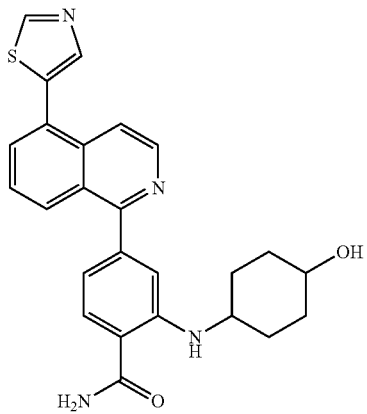 [SMILES: NC(=O)c1ccc(-c2nccc3c(-c4cncs4)cccc23)cc1NC1CCC(O)CC1] | $^1$H-NMR (DMSO-d$_6$): δ 9.34 (1H, s), 8.64 (1H, d, J = 5.8 Hz), 8.31 (1H, d, J = 7.6 Hz), 8.19 (1H, s), 8.10 (1H, d, J = 8.8 Hz), 7.87-7.98 (3H, m), 7.68-7.80 (2H, m), 7.23 (1H, brs), 6.90 (1H, s), 6.72 (1H, d, J = 7.8 Hz), 4.51 (1H, d, J = 3.9 Hz), 3.30-3.60 (2H, m), 1.75-2.05 (4H, m), 1.10-1.35 (4H, m); LRMS (ESI) m/z 445 [M + H]$^+$. |

TABLE 4-continued
| 19 | 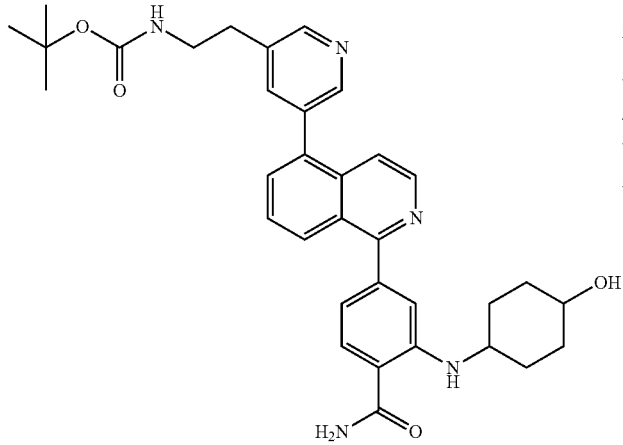 [SMILES: CC(C)(C)OC(=O)NCCc1cncc(-c2cccc3c(-c4ccc(C(N)=O)c(NC5CCC(O)CC5)c4)nccc23)c1] | ¹H-NMR (DMSO-d₆): δ 8.52-8.61 (3H, m), 8.29-8.36 (1H, m), 8.10 (1H, d, J = 8.6 Hz), 7.93 (1H, brs), 7.63-7.85 (5H, m), 7.23 (1H, brs), 6.97 (1H, brs), 6.91 (1H, s), 6.74 (1H, d, J = 8.1 Hz), 4.51 (1H, d, J = 4.2 Hz), 3.30-3.60 (4H, m), 2.85 (1H, t, J = 6.6 Hz), 1.75-2.05 (4H, m), 1.32 (9H, s), 1.10-1.35 (4H, m); LRMS (ESI) m/z 582 [M + H]⁺. |
|---|---|---|
| 20 | 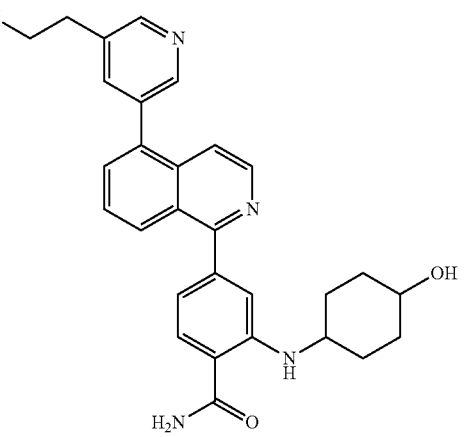 | ¹H-NMR (DMSO-d₆): δ 8.50-8.60 (3H, m), 8.31 (1H, d, J = 7.3 Hz), 8.09 (1H, d, J = 7.8 Hz), 7.92 (1H, brs), 7.61-7.83 (5H, m), 7.22 (1H, brs), 6.91 (1H, s), 6.74 (1H, d, J = 8.1 Hz), 4.51 (1H, d, J = 4.2 Hz), 3.30-3.60 (2H, m), 2.75-2.95 (4H, m), 1.75-2.05 (4H, m), 1.10-1.35 (4H, m); LRMS (ESI) m/z 482 [M + H]⁺. |
TABLE 5
| 21 | 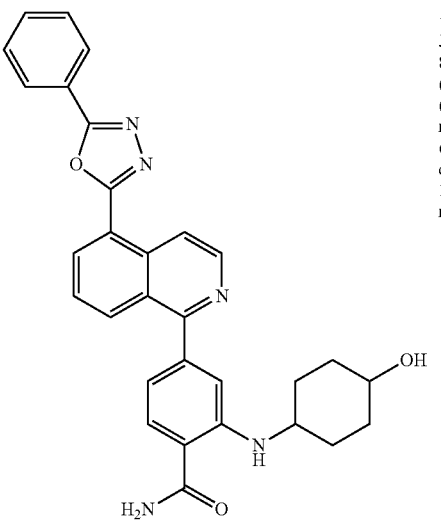 | ¹H-NMR (DMSO-d₆): δ 9.0 7 (1H, d, J = 6.1 Hz), 8.81 (1H, d, J = 5.9 Hz), 8.68 (1H, d, J = 7.3 Hz), 8.20-8.38 (4H, m), 7.85-8.00 (2H, m), 7.79 (1H, d, J = 8.0 Hz), 7.15-7.23 (3H, m), 7.25 (1H, brs), 6.93 (1H, s), 6.74 (1H, d, J = 9.3 Hz), 4.50 (1H, d, J = 4.4 Hz), 3.30-3.60 (2H, m), 1.75-2.05 (4H, m), 1.10-1.35 (4H, m); LRMS (ESI) m/z 506 [M+H]⁺. |
|---|---|---|

TABLE 5-continued
| | | |
|---|---|---|
| 22 | 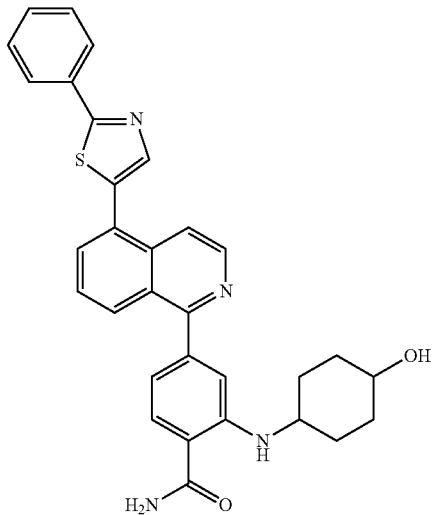 | $^1$H-NMR (DMSO-d$_6$): δ 8.66 (1H, d, J = 6.1 Hz), 8.30-8.50 (1H, m), 8.19 (1H, s), 7.98-8.15 (5H, m), 7.96 (1H, brs), 7.61-7.70 (2H, m), 7.52-7.61 (3H, m), 7.23 (1H, brs), 6.91 (1H, s), 6.73 (1H, d, J = 7.8 Hz), 4.51 (1H, d, J = 4.2 Hz), 3.30-3.60 (2H, m), 1.75-2.05 (4H, m), 1.10-1.35 (4H, m); LRMS (ESI) m/z 521 [M + H]$^+$. |
| 23 | 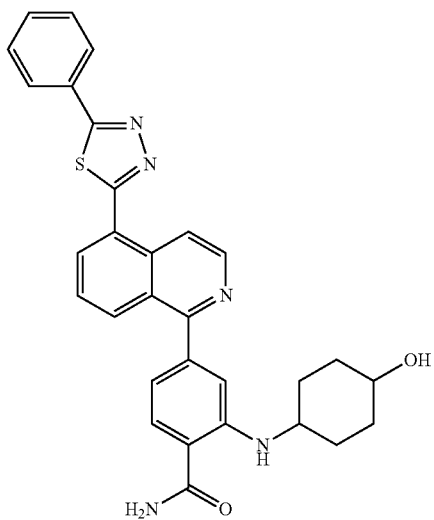 [SMILES: NC(=O)c1ccc(-c2nccc3c(-c4nnc(-c5ccccc5)o4)cccc23)cc1NC1CCC(O)CC1] | $^1$H-NMR (DMSO-d$_6$): δ 8.74 (1H, d, J = 5.18 Hz), 8.63 (1H, d, J = 5.9 Hz), 8.22-8.36 (3H, m), 8.08-8.15 (2H, m), 7.94 (1H, brs), 7.77-7.85 (2H, m), 7.60-7.68 (3H, m), 7.24 (1H, brs), 6.93 (1H, s), 6.75 (1H, d, J = 7.8 Hz), 4.51 (1H, d, J = 4.2 Hz), 3.30-3.60 (2H, m), 1.75-2.05 (4H, m), 1.10-1.35 (4H, m); LRMS (ESI) m/z 522 [M + H]$^+$. |
| 24 | 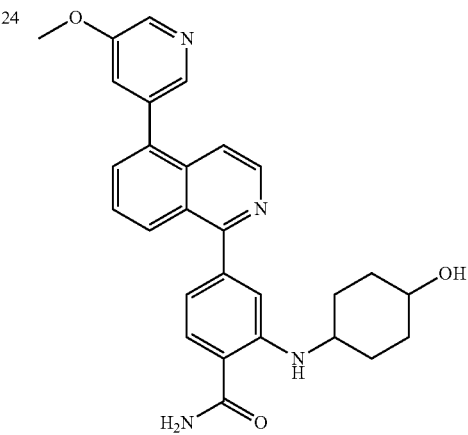 | $^1$H-NMR (DMSO-d$_6$): δ 8.58 (1H, d, J = 5.8 Hz), 8.45 (1H, d, J = 2.7 Hz), 8.29-8.35 (2H, m), 8.10 (1H, d, J = 8.6 Hz), 7.95 (1H, brs), 7.55-7.85 (5H, m), 7.24 (1H, brs), 6.90 (1H, s), 6.74 (1H, d, J = 9.3 Hz), 4.51 (1H, d, J = 4.2 Hz), 3.92 (3H, s), 3.30-3.60 (2H, m), 1.75-2.05 (4H, m), 1.10-1.35 (4H, m); LRMS (ESI) m/z 469 [M + H]$^+$. |

TABLE 5-continued
| 25 | 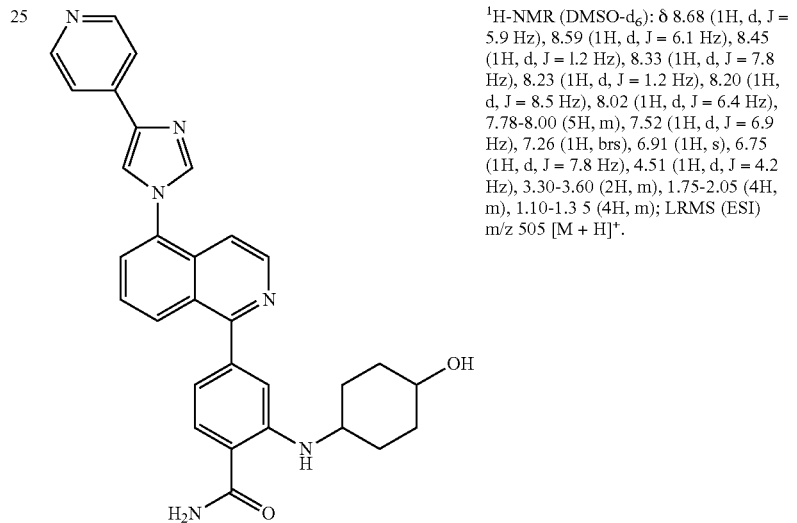 | ¹H-NMR (DMSO-d₆): δ 8.68 (1H, d, J = 5.9 Hz), 8.59 (1H, d, J = 6.1 Hz), 8.45 (1H, d, J = 1.2 Hz), 8.33 (1H, d, J = 7.8 Hz), 8.23 (1H, d, J = 1.2 Hz), 8.20 (1H, d, J = 8.5 Hz), 8.02 (1H, d, J = 6.4 Hz), 7.78-8.00 (5H, m), 7.52 (1H, d, J = 6.9 Hz), 7.26 (1H, brs), 6.91 (1H, s), 6.75 (1H, d, J = 7.8 Hz), 4.51 (1H, d, J = 4.2 Hz), 3.30-3.60 (2H, m), 1.75-2.05 (4H, m), 1.10-1.35 (4H, m); LRMS (ESI) m/z 505 [M + H]⁺. |
TABLE 6
| 26 | 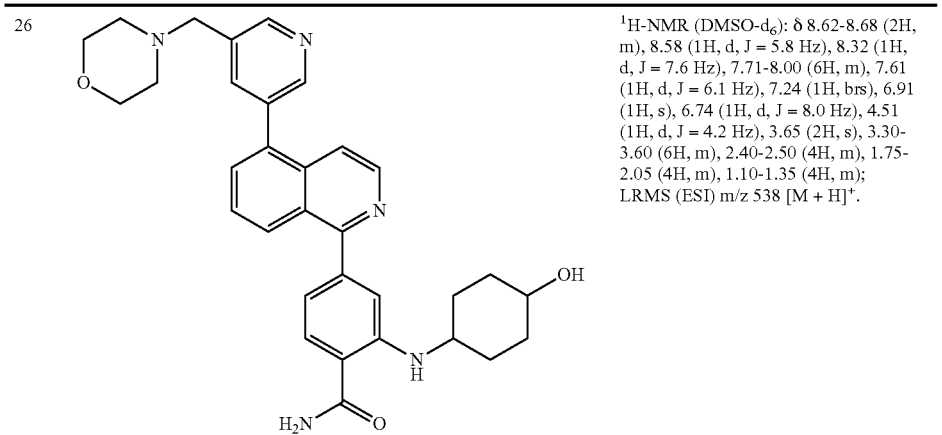 | ¹H-NMR (DMSO-d₆): δ 8.62-8.68 (2H, m), 8.58 (1H, d, J = 5.8 Hz), 8.32 (1H, d, J = 7.6 Hz), 7.71-8.00 (6H, m), 7.61 (1H, d, J = 6.1 Hz), 7.24 (1H, brs), 6.91 (1H, s), 6.74 (1H, d, J = 8.0 Hz), 4.51 (1H, d, J = 4.2 Hz), 3.65 (2H, s), 3.30-3.60 (6H, m), 2.40-2.50 (4H, m), 1.75-2.05 (4H, m), 1.10-1.35 (4H, m); LRMS (ESI) m/z 538 [M + H]⁺. |
| 27 | 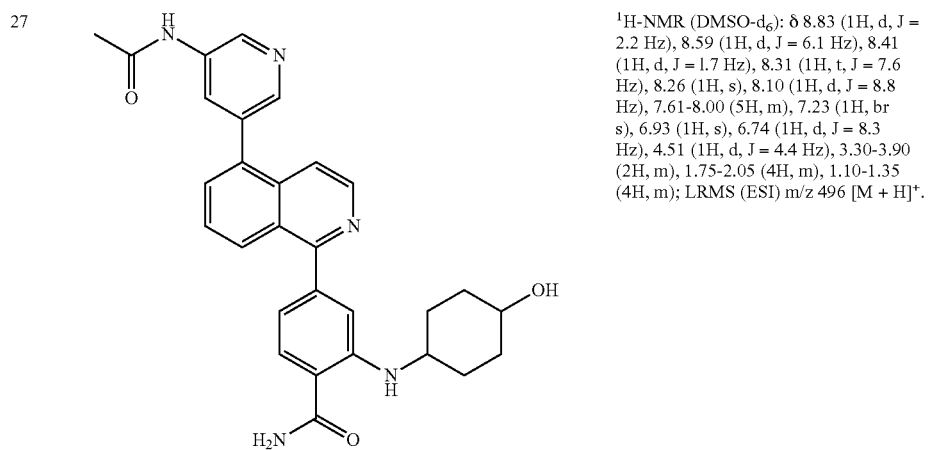 | ¹H-NMR (DMSO-d₆): δ 8.83 (1H, d, J = 2.2 Hz), 8.59 (1H, d, J = 6.1 Hz), 8.41 (1H, d, J = 1.7 Hz), 8.31 (1H, t, J = 7.6 Hz), 8.26 (1H, s), 8.10 (1H, d, J = 8.8 Hz), 7.61-8.00 (5H, m), 7.23 (1H, br s), 6.93 (1H, s), 6.74 (1H, d, J = 8.3 Hz), 4.51 (1H, d, J = 4.4 Hz), 3.30-3.90 (2H, m), 1.75-2.05 (4H, m), 1.10-1.35 (4H, m); LRMS (ESI) m/z 496 [M + H]⁺. |

TABLE 6-continued
| | | |
|---|---|---|
| 28 | 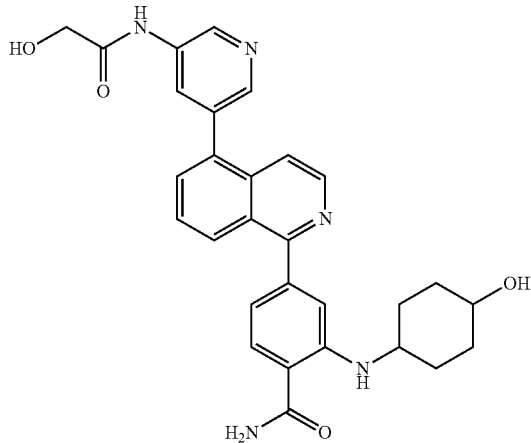 [SMILES: NC(=O)c1ccc(-c2nccc3c(-c4cncc(NC(=O)CO)c4)cccc23)cc1NC1CCC(O)CC1] | ¹H-NMR (DMSO-d₆): δ 9.03 (1H,d, J = 2.4 Hz), 8.59 (1H, d, J = 6.1 Hz), 8.45 (1H, d, J = 1.9 Hz), 8.36 (1H, t, J = 2.2 Hz), 8.31 (1H, d, J = 7.6 Hz), 7.66-8.00 (5H, m), 7.23 (1H, brs), 6.92 (1H, s), 6.74 (1H, d, J = 7.8 Hz), 5.82 (1H, t, J = 5.9 Hz), 4.51 (1H, d, J = 4.4 Hz), 4.07 (1H, d, J = 5.6 Hz), 3.30-3.90 (2H, m), 1.75-2.05 (4H, m), 1.10-1.35 (4H, m); LRMS (ESI) m/z 512 [M + H]⁺. |
| 29 | 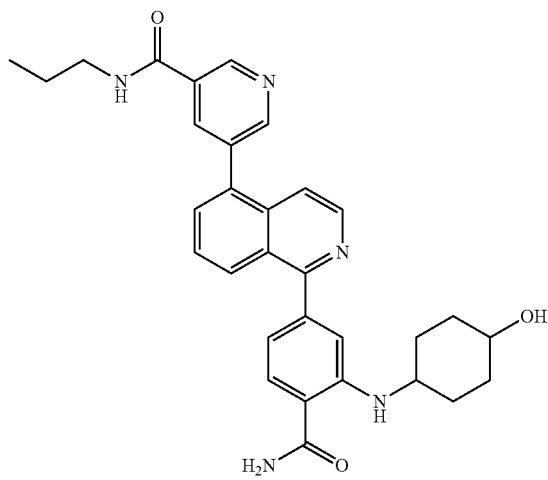 [SMILES: CCCNC(=O)c1cncc(-c2cccc3c(-c4ccc(C(N)=O)c(NC5CCC(O)CC5)c4)nccc23)c1] | ¹H-NMR (DMSO-d₆): δ 9.14 (1H, s), 8.87 (1H, s), 8.75 (1H, brs), 8.60 (1H, d, J = 5.8 Hz), 8.29-8.39 (2H, m), 8.13 (1H, d, J = 2.2 Hz), 7.73-8.00 (5H, m), 7.62 (1H, d, J = 6.1 Hz), 7.23 (1H, brs), 6.91 (1H, s), 6.74 (1H, d, J = 8.0 Hz), 4.51 (1H, d, J = 4.2 Hz), 3.30-3.90 (4H, m), 1.75-2.05 (4H, m), 1.57 (2H, q, J = 7.1 Hz), 1.10-1.35 (4H, m), 0.92 (3H, t, J = 7.1 Hz); LRMS (ESI) m/z 524 [M + H] ⁺. |
| 30 | 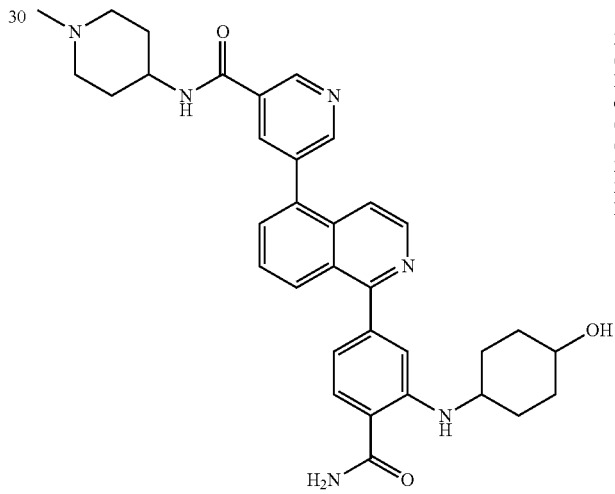 | ¹H-NMR (DMSO-d₆): δ 9.14 (1H, d, J = 2.2 Hz), 8.87 (1H, d, J = 2.2 Hz), 8.60 (1H, d, J = 6.1 Hz), 8.53 (1H, d, J = 7.6 Hz), 8.36 (1H,t = 2.2 Hz), 8.32 (1H, d, J = 6.1 Hz), 7.23 (1H, brs), 6.91 (1H, s), 6.74 (1H, d, J = 9.2 Hz), 4.51 (1H, d, J = 4.1 Hz), 3.30-3.90 (3H, m), 2.70-2.80 (2H, m), 2.17 (3H, s), 1.75-2.05 (10H, m), 1.10-1.35 (4H, m); LRMS (ESI) m/z 579 [M + H]⁺. |

TABLE 7
| 31 | 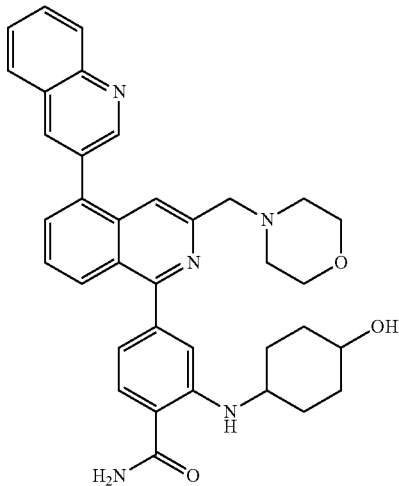 [SMILES: NC(=O)c1ccc(-c2nc(CN3CCOCC3)cc3c(-c4cnc5ccccc5c4)cccc23)cc1NC1CCC(O)CC1] | ¹H-NMR (DMSO-d₆): δ 9.08 (1H, d, J = 2.2 Hz), 8.59 (1H, d, J = 2.2 Hz), 8.32 (1H, d, J = 7.3 Hz), 7.70-8.20 (10H, m), 7.25 (1H, brs), 6.91 (1H, s), 6.76 (1H, d, J = 8.1 Hz), 4.52 (1H, d, J = 4.2 Hz), 3.74 (2H, s), 3.30-3.60 (6H, m), 1.75-2.05 (4H, m), 1.10-1.35 (4H, m); LRMS (ESI) m/z 5 8 [M + H]⁺. |
|---|---|---|
| 32 | 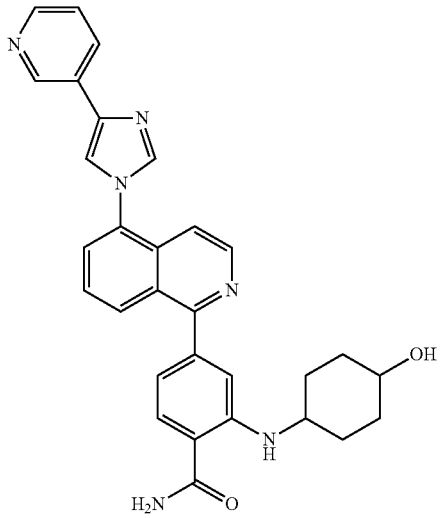 [SMILES: NC(=O)c1ccc(-c2nccc3c(-n4cnc(-c5cccnc5)c4)cccc23)cc1NC1CCC(O)CC1] | ¹H-NMR (DMSO-d₆): δ 9.13 (1H, s), 8.68 (1H, d, J = 6.1 Hz), 8.48 (1H, d, J = 4.6 Hz), 8.16-8.35 (5H, m), 8.01 (1H, d, J = 7.3 Hz), 7.95 (1H, brs), 7.76-7.83 (2H, m), 7.25 (1H, brs), 6.92 (1H, s), 6.75 (1H, d, J = 9.3 Hz), 4.51 (1H, d, J = 4.2 Hz), 3.30-3.60 (2H, m), 1.75-2.05 (4H, m), 1.10-1.35 (4H, m); LRMS (ESI) m/z 505 [M + H]⁺. |
| 33 | 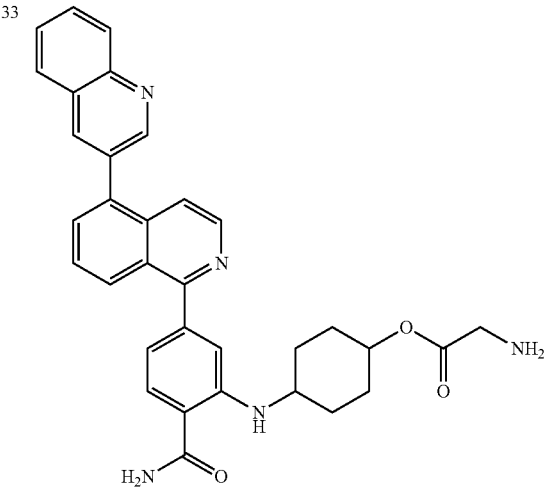 | ¹H-NMR (DMSO-d₆): δ 9.07 (1H, d, J = 2.2 Hz), 8.55-8.62 (2H, m), 8.38 (1H, d, J = 7.8 Hz), 7.70-8.40 (10H, m), 7.27 (1H, brs), 6.97 (1H, s), 6.78 (1H, d, J = 8.1 Hz), 4.60-4.75 (1H, m), 3.45-3.60 (1H, m), 3.21 (2H, s), 1.75-2.15 (4H, m), 1.30-1.65 (6H, m); LRMS (ESI) m/z 54 6[M + H]⁺. |

TABLE 7-continued
| 34 | 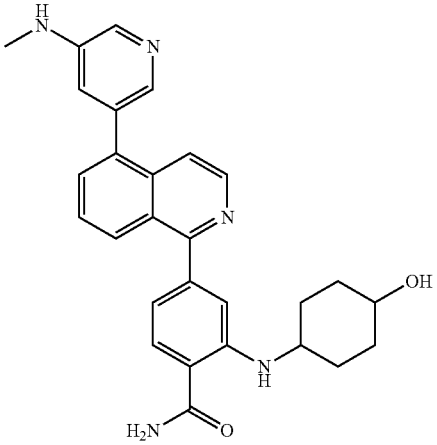 [SMILES: CNc1cncc(-c2cccc3c(-c4ccc(C(N)=O)c(NC5CCC(O)CC5)c4)nccc23)c1] | ¹H-NMR (DMSO-d₆): δ 8.57 (1H, d, J = 5.6 Hz), 8.31 (1H, d, J = 7.3 Hz), 7.65-8.10 (8H, m), 7.23 (1H, brs), 6.98 (1H, s), 6.90 (1H, s), 6.73 (1H, d, J = 8.1 Hz), 6.14 (1H, brs), 4.51 (1H, d, J = 3.9 Hz), 3.30-3.90 (2H, m), 2.77 (1H, d, J = 4.9 Hz), 1.75-2.05 (4H, m), 1.10-1.35 (4H, m); LRMS (ESI) m/z 468 [M + H]⁺. |
|---|---|---|
| 35 | 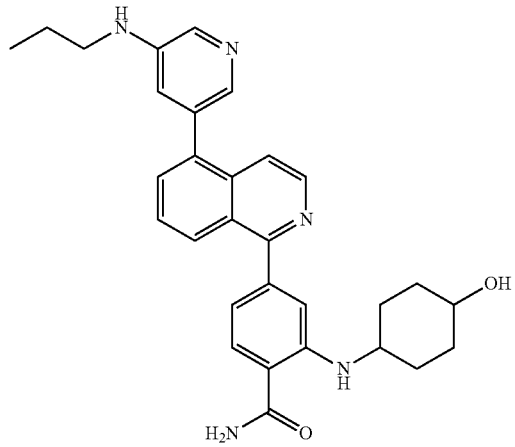 [SMILES: CCCNc1cncc(-c2cccc3c(-c4ccc(C(N)=O)c(NC5CCC(O)CC5)c4)nccc23)c1] | ¹H-NMR (DMSO-d₆): δ 8.57 (1H, d, J = 6.1 Hz), 8.30 (1H, d, J = 8.0 Hz), 7.65-8.10 (8H, m), 7.23 (1H, brs), 7.00 (1H, s), 6.90 (1H, s), 6.73 (1H, d, J = 7.6 Hz), 6.11 (1H, brs), 4.51 (1H, d, J = 3.9 Hz), 3.30-3.90 (2H, m), 3.00-3.05 (2H, m), 1.75-2.05 (4H, m), 1.50-1.60 (2H, m), 1.10-1.35 (4H, m), 0.96 (3H, t, J = 5.1 Hz); LRMS (ESI) m/z 496 [M + H]⁺. |
TABLE 8
| 36 | 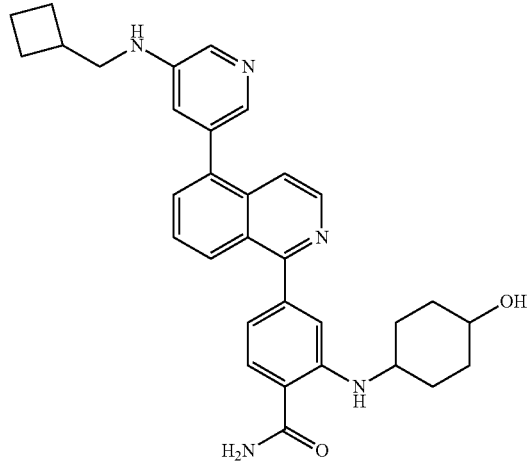 [SMILES: NC(=O)c1ccc(-c2nccc3c(-c4cncc(NCC5CCC5)c4)cccc23)cc1NC1CCC(O)CC1] | ¹H-NMR (DMSO-d₆): δ 8.57 (1H, d, J = 6.1 Hz), 8.31 (1H, d, J = 7.6 Hz), 7.65-8.10 (8H, m), 7.22 (1H, brs), 7.00 (1H, s), 6.90 (1H, s), 6.73 (1H, d, J = 8.3 Hz), 6.06 (1H, brs), 4.51 (1H, d, J = 3.9 Hz), 3.30-3.90 (2H, m), 3.05-3.15 (2H, m), 2.50-2.60 (1H, m), 1.75-2.10 (10H, m), 1.10-1.35 (4H, m); LRMS (ESI) m/z 521 [M + H]⁺. |
|---|---|---|

TABLE 8-continued
| 37 | 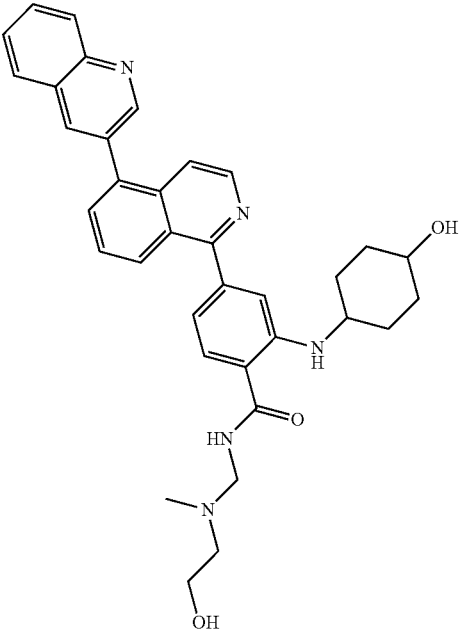 [SMILES: CN(CCO)CNC(=O)c1ccc(-c2nccc3c(-c4cnc5ccccc5c4)cccc23)cc1NC1CCC(O)CC1] | ¹H-NMR (DMSO-d₆): δ 9.07 (1H, d, J = 2.2 Hz), 8.67 (1H, t, J = 6.1 Hz), 8.62-8.57 (2H, m), 8.19-8.09 (3H, m), 7.97-7.68 (7H, m), 6.95 (1H, s), 6.82 (1H, d, J = 8.1 Hz), 4.53 (1H, d, J = 4.1 Hz), 4.46 (1H, t, J = 5.4 Hz), 4.19 (2H, d, J = 5.9 Hz), 3.58-3.37 (4H, m), 2.58 (2H, t, J = 6.3 Hz), 2.29 (3H, s), 2.05-1.74 (4H, m), 1.32-1.15 (4H, m). |
| 38 | | ¹H-NMR (DMSO-d₆): δ 9.07 (1H, d, J = 2.2 Hz), 8.70 (1H, t, J = 6.1 Hz), 8.62-8.57 (2H, m), 8.20-8.10 (3H, m), 7.98-7.68 (7H, m), 6.95 (1H, s), 6.82 (1H, d, J = 7.8 Hz), 4.52 (1H, d, J = 4.1 Hz), 4.08 (2H, d, J = 5.9 Hz), 3.52-3.38 (2H, m), 2.23 (6H, s), 2.05-1.77 (4H, m), 1.30-1.19 (4H, m). |
| 39 | 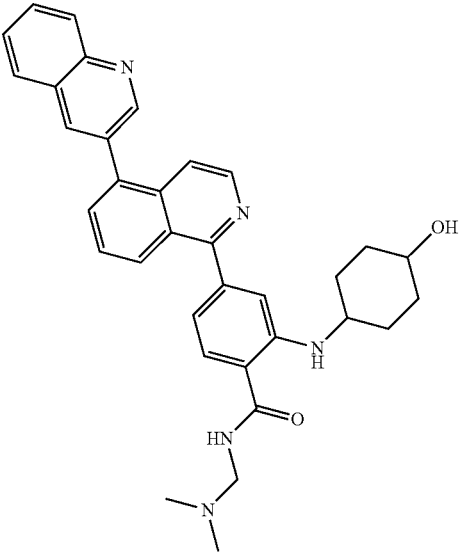 | ¹H-NMR (DMSO-d₆): δ 11.49 (1H, s), 8.56 (1H, d, J = 6.1 Hz), 8.46 (1H, s), 8.32 (1H, d, J = 7.6 Hz), 8.08 (1H, d, J = 8.6 Hz), 7.70-8.00 (7H, m), 7.24 (1H, brs), 6.93 (1H, s), 6.76 (1H, d, J = 8.0 Hz), 6.67-6.71 (1H, m), 4.52 (1H, d, J = 4.2 Hz), 3.30-3.65 (2H, m), 1.75-2.05 (4H, m), 1.10-1.35 (4H, m); LRMS (ESI) m/z 478 [M + H]⁺. |

TABLE 8-continued
| 40 | 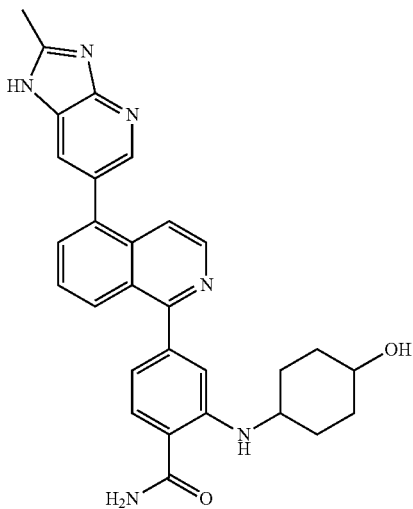 [SMILES: Cc1nc2ncc(-c3cccc4c(-c5ccc(C(N)=O)c(NC6CCC(O)CC6)c5)nccc34)cc2[nH]1] | ¹H-NMR (DMSO-d₆): δ 8.56 (1H, d, J = 5.19 Hz), 8.29-8.44 (5H, m), 7.64-8.10 (7H, m), 7.24 (1H, brs), 6.91 (1H, s), 6.75 (1H, d, J = 7.8 Hz), 4.52 (1H, d, J = 4.1 Hz), 3.30-3.65 (2H, m), 2.59 (3H, s), 1.75-2.05 (4H, m), 1.10-1.35 (4H, m); LRMS (ESI) m/z 493 [M + H]⁺. |
TABLE 9
| 41 | 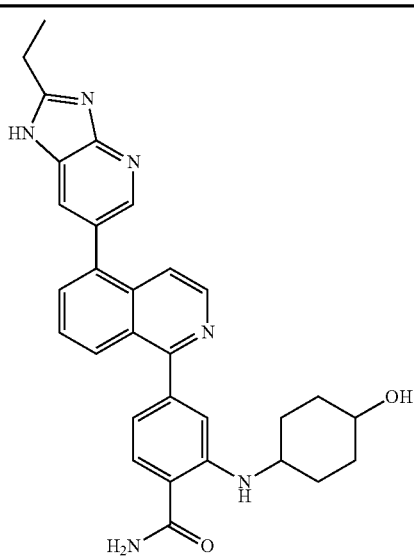 | ¹H-NMR (DMSO-d₆): δ 8.56 (1H, d, J = 5.9 Hz), 8.38 (1H, brs), 8.31 (1H, d, J = 7.6 Hz), 7.65-8.10 (7H, m), 7.24 (1H, brs), 6.92 (1H, s), 6.75 (1H, d, J = 8.1 Hz), 4.51 (1H, d, J = 4.2 Hz), 3.30-3.65 (2H, m), 2.93 (2H, q, J = 7.6 Hz), 1.75-2.05 (4H, m), 1.38 (3H, t, J = 7.6 Hz), 1.10-1.35 (4H, m); LRMS (ESI) m/z 507 [M + H]⁺. |
| 42 | 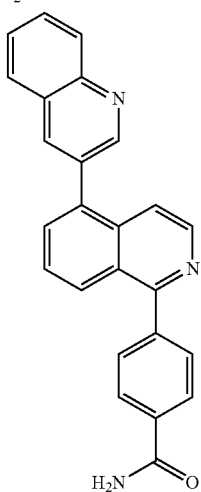 | ¹H-NMR (DMSO-d₆): δ 9.0 7 (1H, d, J = 2.2 Hz), 8.58-8.62 (2H, m), 8.07-8.17 (6H, m), 7.69-7.96 (7H, m), 7.51 (1H, brs); LRMS (ESI) m/z 376 [M + H]⁺. |

TABLE 9-continued

| 43 | (structure: 5-(pyrimidin-5-yl)isoquinoline linked to benzamide with NH-cyclohexanol substituent) | ¹H-NMR (DMSO-d₆): δ 9.36 (1H, s), 9.04 (2H, s), 8.61 (1H, d, J = 6.1 Hz), 8.32 (1H, d, J = 7.6 Hz), 8.15 (1H, d, J = 8.6 Hz), 7.75-8.00 (4H, m), 7.64 (1H, d, J = 6.1 Hz), 7.24 (1H, brs), 6.91 (1H, s), 6.74 (1H, d, J = 8.0 Hz), 4.51 (1H, d, J = 4.2 Hz), 3.30-3.60 (2H, m), 1.75-2.05 (4H, m), 1.10-1.35 (4H, m); LRMS (ESI) m/z 440 [M + H]⁺. |
|---|---|---|
| 44 | (structure: 5-(quinolin-3-yl)isoquinoline linked to 2,5-dimethylbenzamide) | ¹H-NMR (DMSO-d₆): δ 9.09 (1H, d, J = 2.4 Hz), 8.62 (1H, d, J = 2.4 Hz), 8.61 (1H, d, J = 5.8 Hz), 7.44 (2H, s), 7.20 (1H, s), 2.42 (3H, s), 2.01 (3H, s); LRMS (ESI) m/z 404 [M + H]⁺. |
| 45 | (structure: 7-formylquinolin-3-yl linked to isoquinoline, benzamide with NH-cyclohexanol) | ¹H-NMR (DMSO-d₆): δ 10.33 (1H, s), 7.68-8.80 (12H, m), 7.75-7.82 (2H, m) 7.25 (1H, brs), 6.93 (1H, s), 6.76 (1H, d, J = 7.8 Hz), 4.52 (1H, d, J = 4.1 Hz), 3.30-3.60 (2H, m), 1.75-2.05 (4H, m), 1.20-1.35 (4H, m); LRMS (ESI) m/z 517 [M + H]⁺. |

TABLE 10
| | | |
|---|---|---|
| 46 | 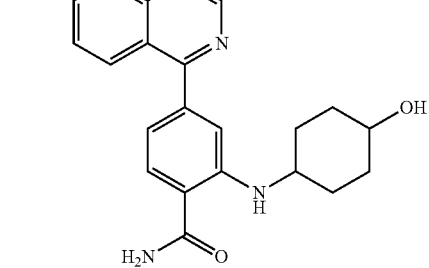 | ¹H-NMR (DMSO-d₆): δ 8.57 (1H, d, J = 5.4 Hz), 8.30 (1H, d, J = 7.6 Hz), 7.67-8.11 (8H, m), 7.18-7.35 (2H, m), 6.90 (1H, s), 6.73 (1H, d, J = 8.0 Hz), 4.51 (1H, d, J = 4.2 Hz), 3.30-3.60 (4H, m), 1.75-2.05 (4H, m), 1.10-1.35 (7H, m); LRMS (ESI) m/z 483 [M + H]⁺. |
| 47 | 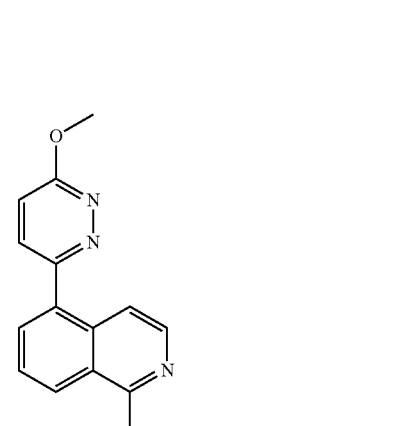 | ¹H-NMR (DMSO-d₆): δ 8.60 (1H, d, J = 5.8 Hz), 8.31 (1H, d, J = 7.6 Hz), 8.15 (1H, d, J = 8.5 Hz), 7.75-8.02 (6H, m), 7.45 (1H, d, J = 9.3 Hz), 7.24 (1H, brs), 6.92 (1H, s), 6.75 (1H, d, J = 8.1 Hz), 4.51 (1H, d, J = 4.4 Hz), 4.16 (3H, s), 3.30-3.60 (2H, m), 1.75-2.05 (4H, m), 1.10-1.35 (4H, m); LRMS (ESI) m/z 470 [M + H]⁺. |
| 48 | 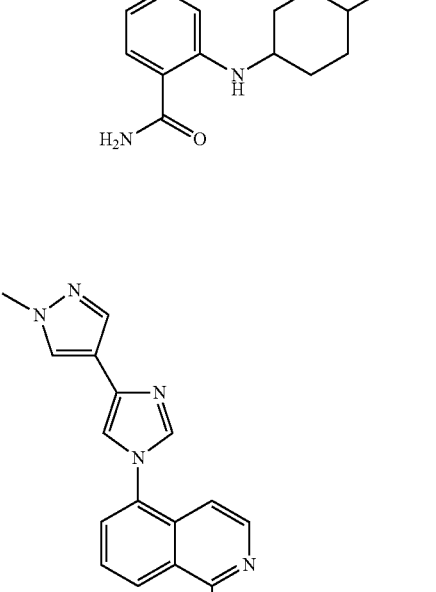 | ¹H-NMR (DMSO-d₆): δ 8.66 (1H, d, J = 5.9 Hz), 8.32 (1H, d, J = 7.3 Hz), 8.15 (1H, d, J = 8.3 Hz), 8.03 (1H, s), 8.00-7.91 (3H, m), 7.82-7.72 (4H, m), 7.53 (1H, d, J = 5.9 Hz), 7.26 (1H, brs), 6.91 (1H, s), 6.74 (1H, d, J = 8.1 Hz), 4.52 (1H, d, J = 4.1 Hz), 3.88 (3H, s), 3.53-3.31 (2H, m), 2.05-1.73 (4H, m), 1.33-1.15 (4H, m). |

TABLE 10-continued
| 49 | 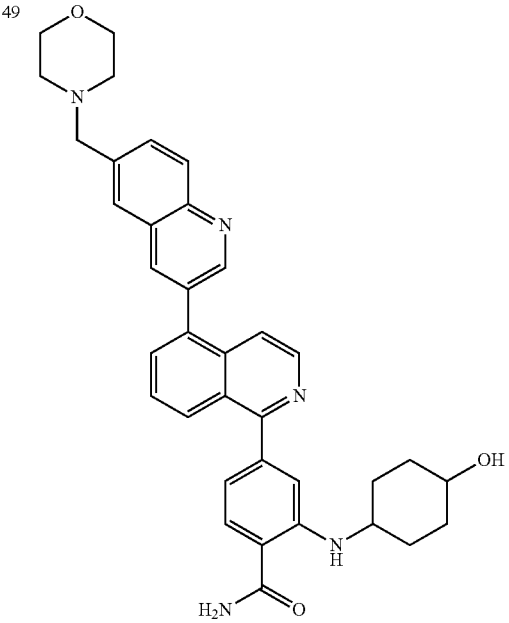 | ¹H-NMR (DMSO-d₆): δ 9.01 (1H, d, J = 1.7 Hz), 8.58 (1H, d, J = 5.85 Hz), 8.54 (1H, d, J = 2.2 Hz), 8.32 (1H, d, J = 7.8 Hz), 7.63-8.08 (8H, m), 7.69 (1H, d, J = 5.9 Hz), 7.24 (1H, brs), 6.92 (1H, s), 6.75 (1H, d, J = 8.1 Hz), 4.51 (1H, d, J = 3.9 Hz), 3.69 (2H, s), 3.58-3.64 (4H, m), 3.30-3.60 (2H, m), 2.40-2.48 (4H, m), 1.75-2.05 (4H, m), 1.20-1.35 (4H, m); LRMS (ESI) m/z 588 [M + H]⁺. |
| --- | --- | --- |
| 50 | 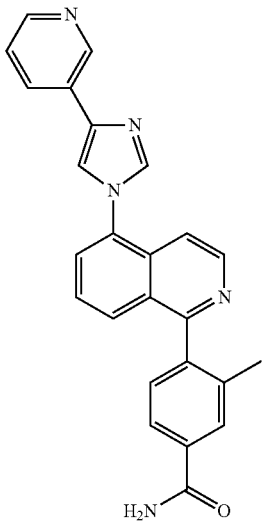 [SMILES: Cc1cc(C(N)=O)ccc1-c1nccc2c(-n3cnc(-c4cccnc4)c3)cccc12] | ¹H-NMR (DMSO-d₆): δ 9.13 (1H, s), 8.70 (1H, d, J = 5.9 Hz), 8.47 (1H, d, J = 3.7 Hz), 8.35 (1H, s), 8.25 (1H, brs), 8.23 (1H, s), 8.08 (1H, brs), 8.01 (1H, d, J = 6.8 Hz), 7.95 (1H, s), 7.87 (1H, d, J = 8.1 Hz), 7.67 (1H, t, J = 7.8 Hz), 7.67 (1H, d, J = 8.5 Hz), 7.60 (1H, d, J = 6.1 Hz), 7.37-7.50 (3H, m), 2.06 (3H, s); LRMS (ESI) m/z 406 [M + H]⁺. |

TABLE 11

| | | |
|---|---|---|
| 51 | (structure) | ¹H-NMR (DMSO-d₆): δ 8.70 (1H, d, J = 5.19 Hz), 8.58 (2H, d, J = 6.1 Hz), 8.50 (1H, d, J = 1.0 Hz), 8.25 (1H, d, J = 1 Hz), 8.08 (1H, brs), 8.02 (1H, d, J = 7.1 Hz), 7.95 (1H, s), 7.83-7.90 (3H, m), 7.76 (1H, t, J = 7.9 Hz), 7.68 (1H, d, J = 8.5 Hz), 7.58 (1H, d, J = 6.1 Hz), 7.46 (1H, s), 7.39 (1H, d, J = 7.8 Hz), 2.05 (3H, s); LRMS (ESI) m/z 406 [M + H]⁺. |
| 52 | (structure) | ¹H-NMR (DMSO-d₆): δ 8.66 (1H, d, J = 5.9 Hz), 8.32 (1H, d, J = 6.4 Hz), 8.15 (1H, d, J = 8.6 Hz), 8.03 (1H, s), 8.00 (1H, s), 7.94 (1H, d, J = 7.3 Hz), 7.75-7.82 (4H, m), 7.54 (1H, d, J = 5.8 Hz), 7.25 (1H, brs), 6.91 (1H, s), 6.74 (1H, d, J = 8.0 Hz), 4.51 (1H, d, J = 4.4 Hz), 3.95 (1H, d, J = 7.3 Hz), 3.30-3.60 (2H, m), 1.75-2.25 (5H, m), 1.10-1.35 (4H, m), 0.88 (6H, d, J = 6.8 Hz); LRMS (ESI) m/z 549 [M + H]⁺. |
| 53 | (structure) | ¹H-NMR (DMSO-d₆): δ 8.60-8.70 (1H, m), 7.48-8.40 (11H, m), 7.15-7.35 (1H, m), 6.70-6.98 (2H, m), 4.45-4.60 (2H, m), 3.30-3.60 (2H, m), 1.75-2.25 (4H, m), 1.10-1.60 (10H, m); LRMS (ESI) m/z 536 [M + H]⁺. |

TABLE 11-continued
| 54 | 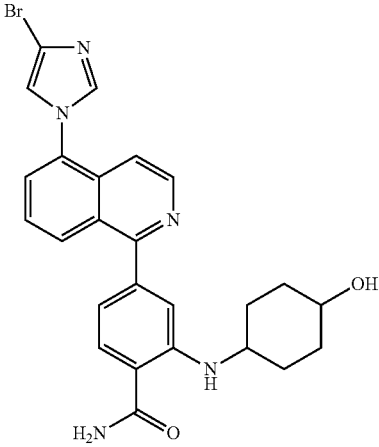 [SMILES: NC(=O)c1ccc(-c2nccc3c(-n4cnc(Br)c4)cccc23)cc1NC1CCC(O)CC1] | ¹H-NMR (DMSO-d₆): δ 8.67 (1H, d, J = 5.9 Hz), 8.28-8.37 (1H, m), 8.18 (1H, d J = 8.6 Hz), 8.09 (1H, s), 7.75-8.00 (5H, m), 7.43 (1H, d, J = 5.8 Hz), 7.25 (1H, brs), 6.89 (1H, s), 6.73 (1H, d, J = 8.3 Hz), 4.20 (1H, brs), 3.30-3.60 2H, m), 1.75-2.05 (4H, m), 1.10-1.35 (4H, m); LRMS (ESI) m/z 507 [M + H]⁺. |
|---|---|---|
| 55 | 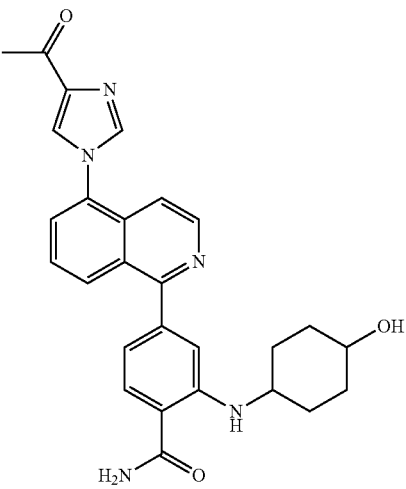 [SMILES: CC(=O)c1cn(-c2cccc3c(-c4ccc(C(N)=O)c(NC5CCC(O)CC5)c4)nccc23)cn1] | ¹H-NMR (DMSO-d₆): δ 8.57 (1H, d, J = 5.8 Hz), 8.28 (1H, d, J = 7.6 Hz), 8.08-7.98 (2H, m), 7.91 (1H, brs), 7.88-7.70 (3H, m), 7..63 (3H, t, J = 7.7 Hz), 7.21 (1H, brs), 6.88 (1H, s), 6.71 (1H, d, J = 8.1 Hz), 4.50 (1H, d, J = 4.1 Hz), 3.54-3.22 (2H, m), 2.50 (3H, s), 2.08-1.70 (4H, m), 1.35-1.10 (4H, m). |
TABLE 12
| 56 | 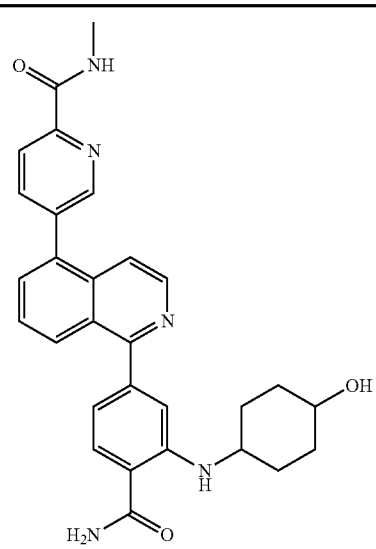 | ¹H-NMR (DMSO-d₆): δ 8.91 (1H, d, J = 4.9 Hz), 8.78 (1H, d, 1 = 1.0 Hz), 8.58 (1H, d, J = 5.9 Hz), 8.31 (1H, d, J = 7.6 Hz), 8.10-8.23 (3H, m), 7.94 (1H, brs), 7.86 (1H, d, J = 6.8 Hz), 7.71-7.79 (2H, m), 7.62 (1H, d, J = 6.1 Hz), 7.24 (1H, brs), 6.90 (1H, s), 6.73 (1H, d, J = 8.1 Hz), 4.51 (1H, d, J = 4.2 Hz), 3.30-3.60 (2H, m), 3.46 (3H, d, J = 4.6 Hz), 1.75-2.05 (4H, m), 1.10-1.35 (4H, m); LRMS (ESI) m/z 496 [M + H]⁺. |
|---|---|---|

TABLE 12-continued
| | | |
|---|---|---|
| 57 | 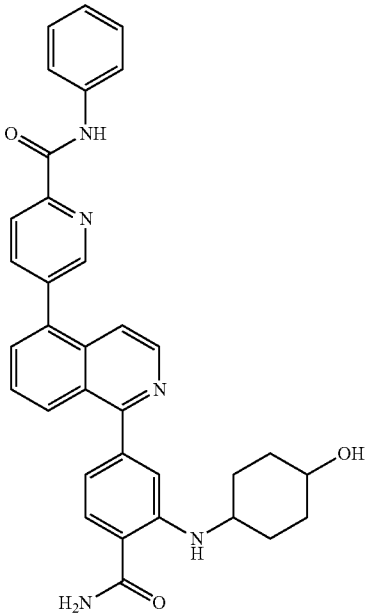 [SMILES: NC(=O)c1ccc(-c2nccc3c(-c4ccc(C(=O)Nc5ccccc5)nc4)cccc23)cc1NC1CCC(O)CC1] | $^1$H-NMR (DMSO-$d_6$): δ 10.77 (1H, s), 8.89 (1H, s), 8.60 (1H, d, J = 6.1 Hz), 8.25-8.40 (3H, m), 8.15 (1H, d, J = 8.5 Hz), 7.75-8.05 (6H, m), 7.66 (1H, d, J = 5.9 Hz), 7.39 (2H, t, J = 7.8 Hz), 7.25 (1H, brs), 7.14 (1H, t, J = 7.3 Hz), 6.91 (1H, s), 6.74 (1H, d, J = 8.1 Hz), 4.51 (1H, d, J = 4.2 Hz), 3.30-3.60 (2H, m), 1.75-2.05 (4H, m), 1.10-1.35 (4H, m); LRMS (ESI) m/z 558 [M + H]$^+$. |
| 58 | 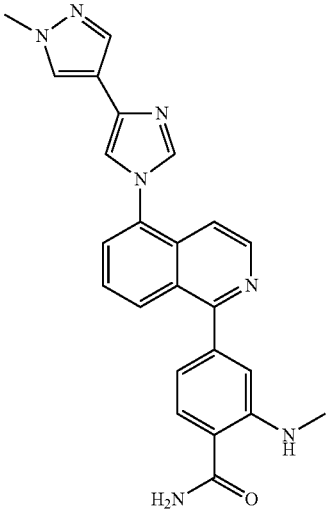 | $^1$H-NMR (DMSO-$d_6$): δ 8.65 (1H, d, J = 5.9 Hz), 8.15-8.25 (2H, m), 7.74-8.05 (8H, m), 7.52 (1H, d, J = 5.9 Hz), 7.29 (1H, brs), 6.86 (1H, s), 6.79 (1H, d, J = 7.6 Hz), 3.87 (3H, s), 2.81 (3H, d, J = 4.9 Hz); LRMS (ESI) m/z 424 [M + H]$^+$. |
| 59 | 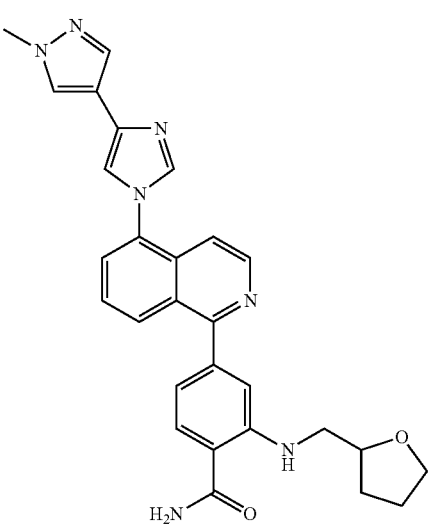 [SMILES: Cn1cc(-c2cn(-c3cccc4c(-c5ccc(C(N)=O)c(NCC6CCCO6)c5)nccc34)cn2)cn1] | $^1$H-NMR (DMSO-$d_6$): δ 8.65 (1H, d, J = 6.1 Hz), 8.42 (1H, t, J = 5.2 Hz), 8.18 (1H, d, J = 8.8 Hz), 8.04-7.91 (4H, m), 7.82-7.73 (4H, m), 7.52 (1H, d, J = 5.9 Hz), 7.27 (1H, brs), 6.94 (1H, d, J = 1.2 Hz), 6.80 (1H, d, J = 8.1 Hz), 4.08-3.99 (1H, m), 3.88 (3H, s), 3.83-3.75 (1H, m), 3.70-3.62 (1H, m), 3.31-3.23 (1H, m), 3.18-3.08 (1H, m), 2.01-1.75 (3H, m), 1.65-1.52 (1H, m). |

TABLE 12-continued

| 60 | [structure] | $^1$H-NMR (DMSO-$d_6$): δ 8.66 (1H, d, J = 5.9 Hz), 8.54-8.35 (3H, m), 8.18 (1H, d, J = 8.5 Hz), 8.05-7.91 (4H, m), 7.84-7.66 (5H, m), 7.53 (1H, d, J = 5.9 Hz), 7.36-7.24 (2H, m), 6.98 (1H, s), 6.81 (1H, d, J = 8.1 Hz), 3.88 (3H, s), 3.43 (2H, q, J = 6.6 Hz), 2.93 (2H, t, J = 6.6 Hz). |
|---|---|---|

TABLE 13

| 61 | [structure] | $^1$H-NMR (DMSO-$d_6$): δ 8.66 (1H, d, J = 5.9 Hz), 8.24 (1H, d, J = 7.3 Hz), 8.17 (1H, d, J = 8.3 Hz), 7.90-8.05 (4H, m), 7.73-7.80 (5H, m), 7.52 (1H, d, J = 5.9 Hz), 7.25 (1H, brs), 6.89 (1H, s), 6.76 (1H, d, J = 7.6 Hz), 3.88 (3H, s), 3.60-3.70 (1H, m), 1.18 (6H, d, J = 6.1 Hz); LRMS (ESI) m/z 452 [M + H]$^+$. |
|---|---|---|
| 62 | [structure] | $^1$H-NMR (CDCl$_3$) 8.66 (1H, d, J = 5.9 Hz), 8.27 (1H, d, J = 8.5 Hz), 8.12 (1H, brs), 7.55-7.82 (6H, m), 7.34 (1H, d, J = 1.2 Hz), 7.01 (1H, d, J = 1.5 Hz), 6.89 (1H, dd, J = 8.1, 1.5 Hz), 3.98 (3H, s), 3.65 (2H, t, J = 5.6 Hz), 3.39-3.45 (5H, m); LRMS (ESI) m/z 468 [M + H]$^+$. |

TABLE 13-continued
| 63 | 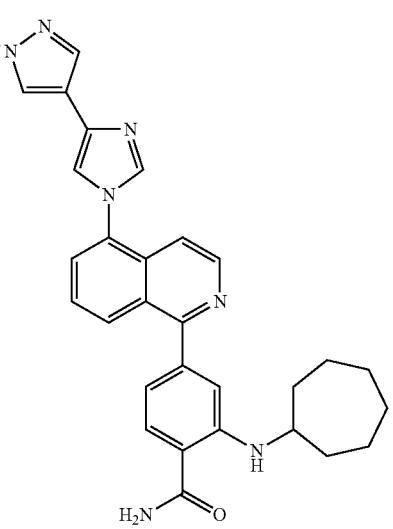 | ¹H-NMR (DMSO-d₆): δ 8.66 (1H, d, J = 6.1 Hz), 8.42 (1H, d, J = 7.1 Hz), 8.19 (1H, d, J = 8.5 Hz), 7.90-8.05 (4H, m), 7.72-7.81 (4H, m), 7.52 (1H, d, J = 5.9 Hz), 7.25 (1H, brs), 6.83 (1H, s), 6.77 (1H, d, J = 7.8 Hz), 3.88 (3H, s), 3.00-3.20 (1H, m), 1.35-2.00 (12H, m); LRMS (ESI) m/z 505 [M + H]⁺. |
|---|---|---|
| 64 | 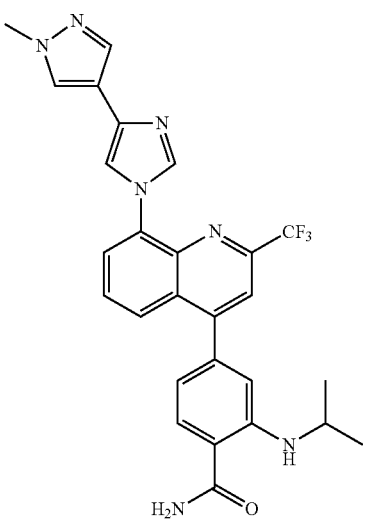 [SMILES: CC(C)Nc1cc(-c2cc(C(F)(F)F)nc3c(-n4cnc(-c5cnn(C)c5)c4)cccc23)ccc1C(N)=O] | ¹H-NMR (DMSO-d₆): δ 8.26-8.33 (2H, m), 7.87-8.13 (9H, m), 7.81 (1H, d, J = 8.3 Hz), 7.73 (1H, s), 7.29 (1H, brs), 6.86 (1H, s), 6.71 (1H, dd, J = 7.9, 1.59 Hz), 3.88 (3H, s), 3.65-3.75 (1H, m), 1.17 (6H, d, J = 6.1 Hz); LRMS (ESI) m/z 520 [M + H]⁺. |
| 65 | 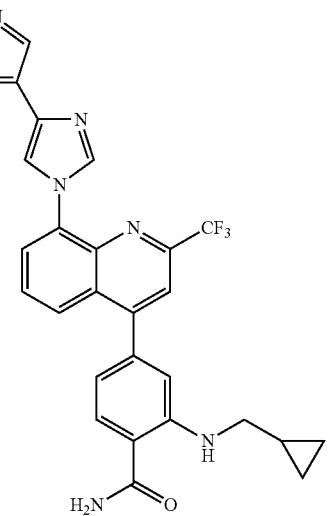 | ¹H-NMR (DMSO-d₆): δ 8.41 (1H, t, J = 4.6 Hz), 8.28 (1H, s), 8.11 (1H, d, J = 7.6 Hz), 7.80-8.05 (8H, m), 7.73 (1H, s), 7.30 (1H, brs), 6.84 (1H, s), 6.74 (1H, d, J = 8.1 Hz), 3.88 (3H, s), 3.02 (2H, t, J = 6.0 Hz), 1.00-1.20 (1H, m), 0.47-0.55 (2H, m), 0.20-26 (2H, m); LRMS (ESI) m/z 531 [M + H]⁺. |

TABLE 14

| | | |
|---|---|---|
| 66 | (structure) | ¹H-NMR (DMSO-d₆): δ 8.16-8.26 (1H, m), 8.10 (1H, d, J = 8.5 Hz), 7.64-8.03 (8H, m), 7.33 (1H, s), 7.26 (1H, br s), 6.84 (1H, s), 6.76 (1H, d, J = 8.1Hz), 3.88 (3H, s), 3.05-3.25 (2H, m), 2.62 (3H, s), 1.20 (3H, t, J = 7.1 Hz); LRMS (ESI) m/z 452 [M + H]⁺. |
| 67 | (structure) | ¹H-NMR (DMSO-d₆): δ 8.25 (1H, d, J = 7.1 Hz), 8.10 (1H, d, J = 8.5 Hz), 7.64-8.03 (8H, m), 7.33 (1H, s), 7.24 (1H, br s), 6.85 (1H, s), 6.74 (1H, d, J = 8.1 Hz), 3.88 (3H, s), 3.55-3.70 (1H, m), 2.62 (3H, s), 1.17 (3H, t, J = 6.1 Hz); LRMS (ESI) m/z 466 [M + H]⁺. |
| 68 | (structure) | ¹H-NMR (DMSO-d₆): δ 8.32-8.40 (1H, m), 8.09 (1H, d, J = 8.8 Hz), 7.64-8.05 (8H, m), 7.33 (1H, s), 7.26 (1H, br s), 6.84 (1H, s), 6.75 (1H, d, J = 8 Hz), 3.88 (3H, s), 1.00-1.25 (1H, m), 0.48-0.55 (2H, m), 0.22-0.30 (2H, m); LRMS (ESI) m/z 478 [M + H]⁺. |

TABLE 14-continued
| | | |
|---|---|---|
| 69 | 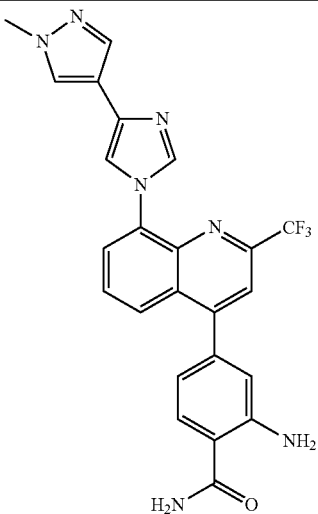 | ¹H-NMR (DMSO-d₆): δ 8.29 (1H, s), 8.11 (1H, d, J = 7.3 Hz), 8.04 (1H, d, J = 8.5 Hz), 7.8 0-8.00 (5H, m), 7.77 (1H, d, J = 8.1 Hz), 7.72 (1H, s), 7.25 (1H, br s), 6.93 (1H, s), 6.85 (2H, s), 6.72 (1H, d, J = 7.6 Hz), 3.88 (3H, s); LRMS (ESI) m/z 478 [M + H]⁺. |
| 70 | 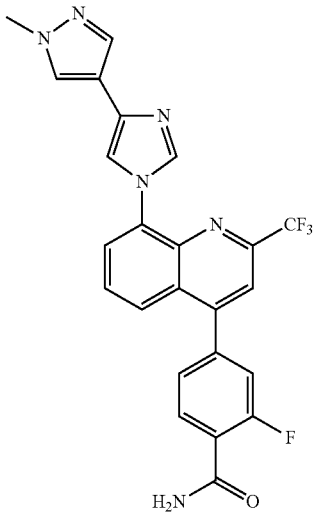 [SMILES: Cn1cc(-c2cn(-c3cccc4c(-c5ccc(C(N)=O)c(F)c5)cc(C(F)(F)F)nc34)cn2)cn1] | ¹H-NMR (DMSO-d₆): δ 8.25-8.35 (1H, m), 8.05-8.20 (2H, m), 7.63-8.00 (9H, m), 7.50-7.60 (1H, m), 3.88 (3H, s); LRMS (ESI) m/z 481 [M + H]⁺. |
TABLE 15
| | | |
|---|---|---|
| 71 | 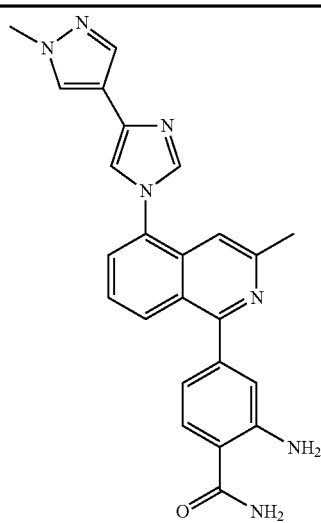 | ¹H-NMR (DMSO-d₆): δ 8.11 (1H, d, J = 8.8 Hz), 8.00 (1H, d, J = 1.5 Hz), 7.97 (1H, s), 7.86 (2H, d, J = 6.8 Hz), 7.65-7.75 (4H, m), 7.32 (1H, s), 7.19 (1H, br s), 6.98 (1H, d, J = 1.7 Hz), 6.78 (2H, br s), 6.73 (1H, dd, J = 8.2, 1.6 Hz), 3.88 (3H, s), 2.62 (3H, s); LRMS (ESI) m/z 424 [M + H]⁺. |

TABLE 15-continued
| | | |
|---|---|---|
| 72 | 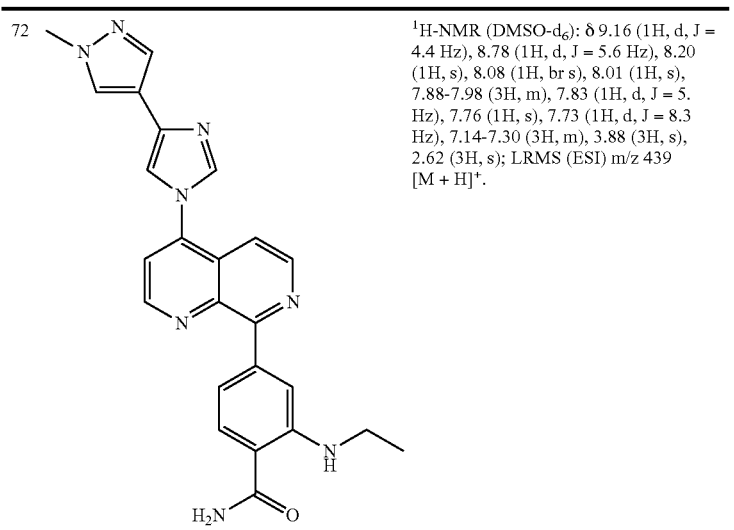 | $^1$H-NMR (DMSO-$d_6$): δ 9.16 (1H, d, J = 4.4 Hz), 8.78 (1H, d, J = 5.6 Hz), 8.20 (1H, s), 8.08 (1H, br s), 8.01 (1H, s), 7.88-7.98 (3H, m), 7.83 (1H, d, J = 5. Hz), 7.76 (1H, s), 7.73 (1H, d, J = 8.3 Hz), 7.14-7.30 (3H, m), 3.88 (3H, s), 2.62 (3H, s); LRMS (ESI) m/z 439 [M + H]$^+$. |
| 73 | 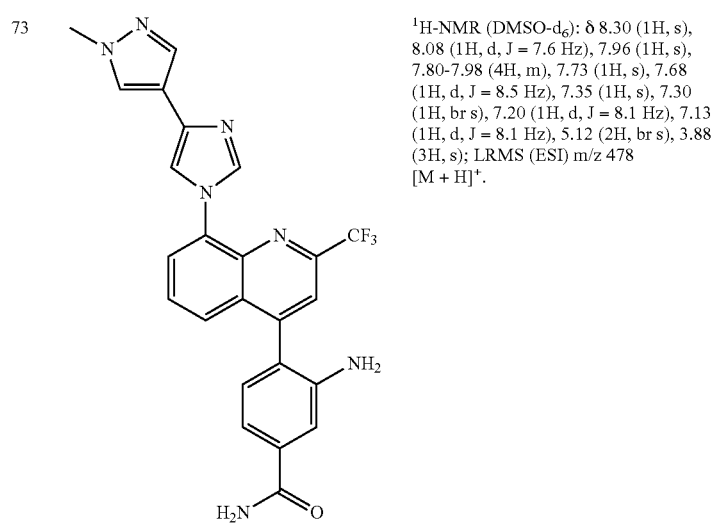 | $^1$H-NMR (DMSO-$d_6$): δ 8.30 (1H, s), 8.08 (1H, d, J = 7.6 Hz), 7.96 (1H, s), 7.80-7.98 (4H, m), 7.73 (1H, s), 7.68 (1H, d, J = 8.5 Hz), 7.35 (1H, s), 7.30 (1H, br s), 7.20 (1H, d, J = 8.1 Hz), 7.13 (1H, d, J = 8.1 Hz), 5.12 (2H, br s), 3.88 (3H, s); LRMS (ESI) m/z 478 [M + H]$^+$. |
| 74 | 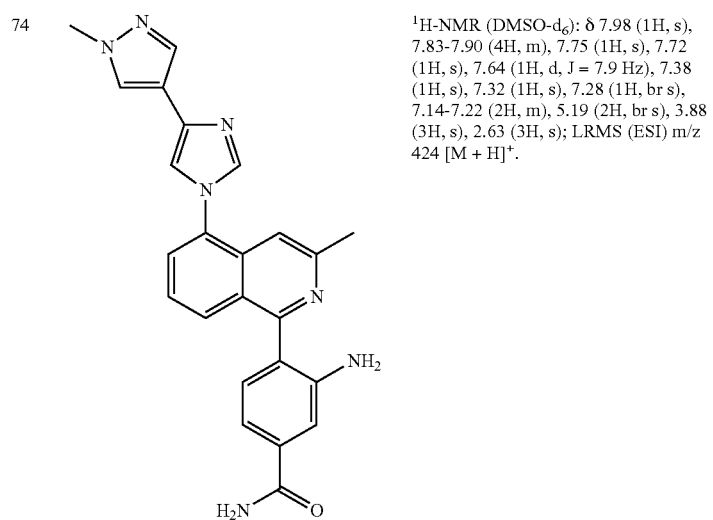 | $^1$H-NMR (DMSO-$d_6$): δ 7.98 (1H, s), 7.83-7.90 (4H, m), 7.75 (1H, s), 7.72 (1H, s), 7.64 (1H, d, J = 7.9 Hz), 7.38 (1H, s), 7.32 (1H, s), 7.28 (1H, br s), 7.14-7.22 (2H, m), 5.19 (2H, br s), 3.88 (3H, s), 2.63 (3H, s); LRMS (ESI) m/z 424 [M + H]$^+$. |

TABLE 15-continued
| | | |
|---|---|---|
| 75 | 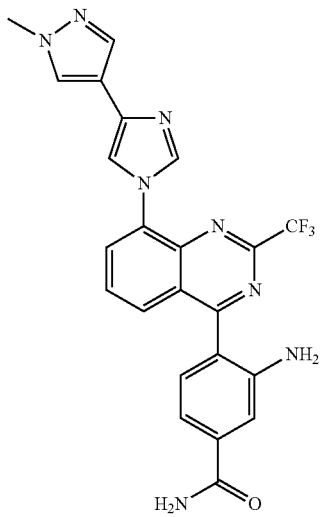 [SMILES: Cn1cc(-c2cn(-c3cccc4c(-c5ccc(C(N)=O)cc5N)nc(C(F)(F)F)nc34)cn2)cn1] | ¹H-NMR (DMSO-d₆): δ 8.25-8.40 (2H, m), 7.80-8.10 (5H, m), 7.74 (1H, br s), 7.15-7.45 (4H, m), 5.53 (2H, br s); LRMS (ESI) m/z 479 [M + H]⁺. |
TABLE 16
| | | |
|---|---|---|
| 76 | 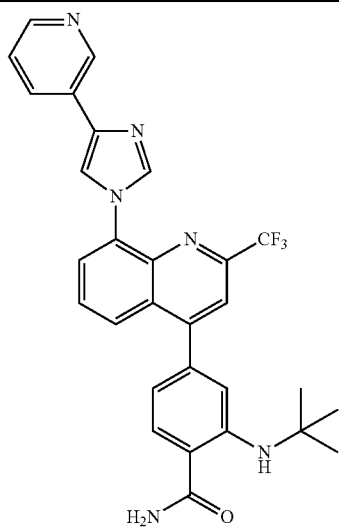 | ¹H-NMR (DMSO-d₆): δ 9.11 (1H, d, J = 2.0 Hz), 8.58 (1H, s), 8.47 (1H, dd, J = 4.88, 1.5 Hz), 8.41 (2H, s), 8.15-8.23 (2H, m), 8.07 (1H, d, J = 8.8 Hz), 7.90-8.02 (3H, m), 7.82 (1H, d, J = 8.3 Hz), 7.45 (1H, dd, J = 7.9, 5.0 Hz), 7.32 (1H, br s), 6.99 (1H, s), 6.74 (1H, d, J = 8.1 Hz), 1.35 (9H, s); LRMS (ESI) m/z 531 [M + H]⁺. |
| 77 | 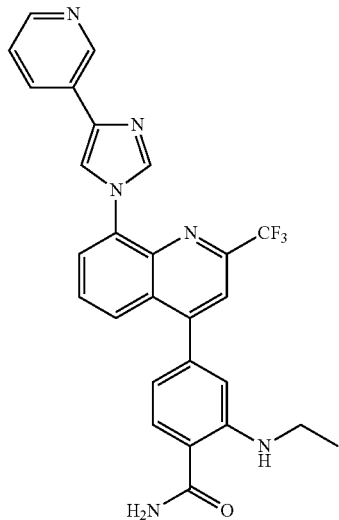 [SMILES: CCNc1cc(-c2cc(C(F)(F)F)nc3c(-n4cnc(-c5cccnc5)c4)cccc23)ccc1C(N)=O] | ¹H-NMR (DMSO-d₆): δ 9.11 (1H, s), 8.51-8.44 (1H, m), 8.42 (1H, s), 8.41 (1H, s), 8.32-8.16 (3H, m), 8.13-7.80 (5H, m), 7.50-7.42 (1H, m), 7.33 (1H, br s), 6.86 (1H, s), 6.75 (1H, d, J = 7.8 Hz), 3.23-3.14 (2H, m), 1.21 (3H, t, J = 7.1 Hz) |

TABLE 16-continued
| 78 | 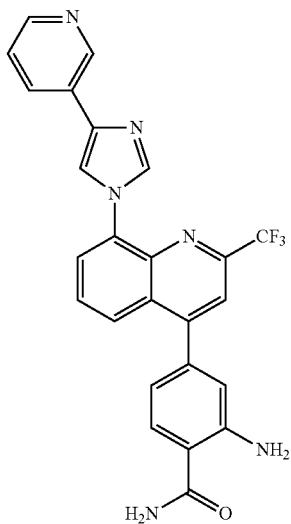 [SMILES: NC(=O)c1ccc(-c2cc(C(F)(F)F)nc3c(-n4cnc(-c5cccnc5)c4)cccc23)cc1N] | ¹H-NMR (DMSO-d₆): δ 9.11 (1H, s), 8.47 (1H, d, J = 4.6 Hz), 8.42 (2H, s), 8.26-8.16 (2H, m), 8.09 (1H, d, J = 7.8 Hz), 8.03-7.90 (3H, m), 7.78 (1H, d, J = 8.1 Hz), 7.46 (1H, dd, J = 7.4, 4.8 Hz), 7.27 (1H, br s), 6.94 (1H, s), 6.86 (2H, br s), 6.74 (1H, d, J = 8.5 Hz) |
| --- | --- | --- |
| 79 | 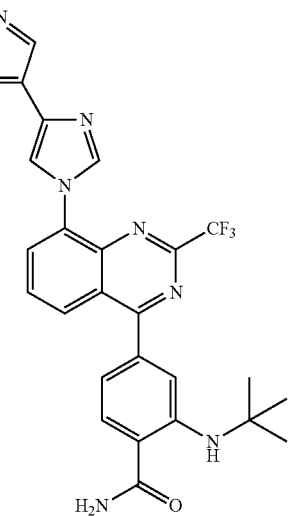 | ¹H-NMR (DMSO-d₆): δ 8.51 (1H, s), 8.35 (1H, d, J = 7.8 Hz), 8.32 (1H, s), 8.24 (1H, d, J = 8.5 Hz), 8.00-8.07 (2H, m), 7.97 (1H, s), 7.93 (1H, s), 7.83 (1H, d, J = 7.8 Hz), 7.73 (1H, s), 7.37 (1H, br s), 7.25 (1H, s), 6.93 (1H, d, J = 7.8 Hz), 3.88 (3H, s), 1.36 (9H, s); LRMS (ESI) m/z 535 [M + H]⁺. |
| 80 | 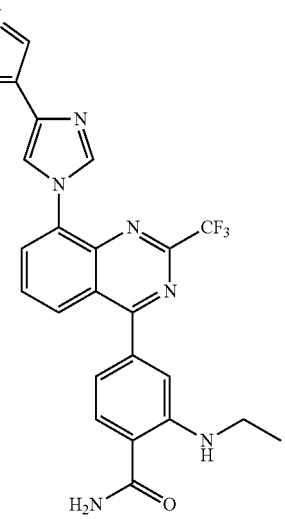 | ¹H-NMR (DMSO-d₆): δ 8.36 (1H, d, J = 7.6 Hz), 8.33 (1H, s), 8.29-8.20 (2H, m), 8.09-8.00 (2H, m), 7.98 (1H, s), 7.93 (1H, s), 7.87 (1H, d, J = 8.1 Hz), 7.74 (1H, s), 7.40 (1H, br s), 7.03 (1H, s), 6.94 (1H, d, J = 7.6 Hz), 3.89 (3H, s), 3.23-3.14 (2H, m), 1.22 (3H, t, J = 7.1 Hz) |

TABLE 17

| 81 | (structure) | ¹H-NMR (DMSO-d₆): δ 8.28 (1H, d, J = 1.5 Hz), 8.14 (1H, dd, J = 7.1, 1.7 Hz), 8.07 (1H, s), 8.02 (1H, br s), 7.98-7.87 (4H, m), 7.83 (1H, d, J = 1.7 Hz), 7.75 (1H, s), 7.73-7.63 (3H, m), 3.87 (3H, s) |
| --- | --- | --- |
| 82 | (structure) | ¹H-NMR (DMSO-d₆): δ 8.06-7.95 (4H, m), 7.89 (1H, d, J = 7.3 Hz), 7.78-7.62 (7H, m), 7.38 (1H, s), 3.87 (3H, s), 2.63 (3H, s) |
| 83 | (structure) | ¹H-NMR (DMSO-d₆): δ 8.90 (1H, s), 8.25-8.35 (4H, m), 8.21 (1H, s), 8.15 (1H, t, J = 4.4 Hz), 7.88-7.98 (4H, m), 7.82 (1H, br s), 7.73 (1H, s), 3.88 (3H, s); LRMS (ESI) m/z 464 [M + H]⁺. |

TABLE 17-continued

| | | |
|---|---|---|
| 84 | (structure) | ¹H-NMR (DMSO-d₆): δ 8.31 (1H, s), 8.13-8.07 (2H, m), 8.02 (1H, s), 7.99-7.94 (2H, m), 7.92-7.82 (3H, m), 7.72 (1H, s), 7.53-7.45 (2H, m), 7.42 (1H, d, J = 7.8 Hz), 3.88 (3H, s), 2.06 (3H, s) |
| 85 | (structure) | ¹H-NMR (DMSO-d₆): δ 8.40-8.35 (2H, m), 8.14 (1H, br s), 8.03-7.91 (5H, m), 7.81-7.72 (2H, m), 7.60-7.50 (2H, m), 3.89 (3H, s), 2.18 (3H, s) |

TABLE 18

| | | |
|---|---|---|
| 86 | (structure) | ¹H-NMR (DMSO-d₆): δ 8.58 (1H, s), 8.28 (1H, d, J = 1.5 Hz), 8.11 (1H, d, J = 6.1 Hz), 7.87-8.05 (6H, m), 7.81 (1H, d, J = 8.1 Hz), 7.72 (1H, s), 7.31 (1H, br s), 6.98 (1H, d, J = 1.5 Hz), 6.73 (1H, dd, J = 7.8, 1.5 Hz), 3.88 (3H, s), 1.34 (9H, s); LRMS (ESI) m/z 534 [M + H]⁺. |

TABLE 18-continued

| 87 | (structure) | ¹H-NMR (DMSO-d₆): δ 8.30 (1H, s), 8.07 (1H, d, J = 7.3 Hz), 8.00 (1H, br s), 7.96 (1H, s), 7.91 (1H, s), 7.89 (1H, s), 7.82 (1H, t, J = 8.2 Hz), 7.73 (1H, s), 7.63 (1H, d, J = 8.8 Hz), 7.36 (1H, br s), 7.22-7.30 (2H, m), 7.14 (1H, d, J = 7.8 Hz), 4.94 (1H, br s), 3.88 (3H, s), 2.90-3.10 (2H, m), 1.40-1.50 (2H, m), 0.77 (3H, t, J = 7.3 Hz); LRMS (ESI) m/z 520 [M + H]⁺. |
| 88 | (structure) | ¹H-NMR (DMSO-d₆): δ 9.11 (1H, s), 8.90 (1H, s), 8.40-8.50 (3H, m), 8.19-8.35 (7H, m), 7.93-8.02 (2H, m), 7.82 (1H, br s), 7.44-7.49 (1H, m); LRMS (ESI) m/z 461 [M + H]⁺. |
| 89 | (structure) | ¹H-NMR (DMSO-d₆): δ 8.24-8.30 (2H, m), 8.11 (1H, d, J = 7.3 Hz), 7.95-8.06 (4H, m), 7.86-7.93 (2H, m), 7.82 (1H, d, J = 8.1 Hz), 7.74 (1H, s) 7.32 (1H, br s), 6.84 (1H, s) 6.74 (1H, dd, J = 7.9, 1.6 Hz), 4.17 (2H, q, J = 7.2 Hz), 3.10-3.25 (2H, m), 1.41 (3H, t, J = 7.2 Hz), 1.20 (3H, t, J = 7.1 Hz); LRMS (ESI) m/z 520 [M + H]⁺. |

TABLE 18-continued
| 90 | 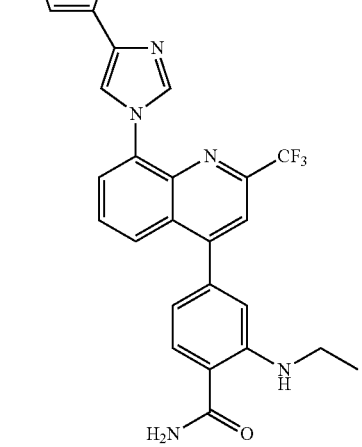 | $^1$H-NMR (DMSO-$d_6$): δ 8.58 (1H, s), 8.28 (1H, s), 8.10 (1H, d, J = 7.3 Hz), 7.70-8.15 (7H, m), 7.31 (1H, br s), 6.98 (1H, s), 6.73 (1H, d, J = 8.1 Hz), 4.17 (2H, q, J = 7.2 Hz), 1.40 (3H, t, J = 7.2 Hz), 1.34 (9H, s); LRMS (ESI) m/z 548 [M + H]$^+$. |
TABLE 19
| 91 | | $^1$H-NMR (DMSO-$d_6$): δ 8.47 (1H, s), 8.33 (1H, s), 8.26 (1H, t, J = 5.2 Hz), 7.80-8.16 (9H, m), 7.31(1H, br s), 6.85 (1H, s) 6.74 (1H, d, J = 9.0 Hz), 3.10-3.25 (2H, m), 1.20 (3H, t, J = 7.1 Hz); LRMS (ESI) m/z 520 [M + H]$^+$. |
| 92 | 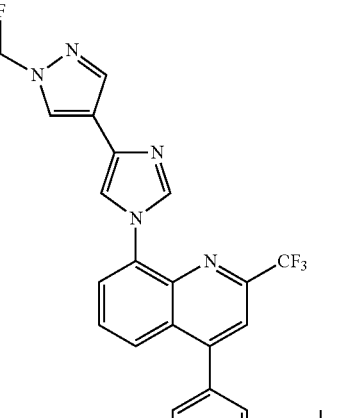 | $^1$H-NMR (DMSO-$d_6$): δ 8.58 (1H, s), 8.47 (1H, s), 8.33 (1H, d, J = 1.2 Hz), 7.79-8.15 (9H, m), 7.31 (1H, br s), 6.99 (1H, d, J = 1.2 Hz), 6.74 (1H, dd, J = 8.1, 1.5 Hz), 1.35 (9H, s); LRMS (ESI) m/z 570 [M + H]$^+$. |

TABLE 19-continued
| | | |
|---|---|---|
| 93 | 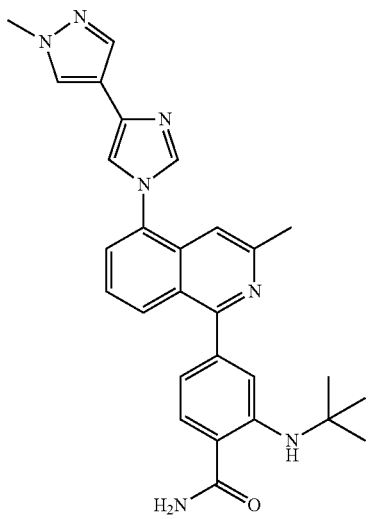 [SMILES: Cc1cc2c(-n3cnc(-c4cnn(C)c4)c3)cccc2c(-c2ccc(C(N)=O)c(NC(C)(C)C)c2)n1] | $^1$H-NMR (DMSO-d$_6$): δ 8.49 (1H, s), 8.12 (1H, d, J = 8.5 Hz), 8.01 (1H, s), 7.97 (1H, s), 7.96 (1H, br s), 7.85 (1H, d, J = 7.3 Hz), 7.75 (1H, d, J = 8.1 Hz), 7.74 (2H, s), 7.67 (1H, t, J = 7.8 Hz), 7.33 (1H, s), 7.26 (1H, br s), 7.06 (1H, s), 6.77 (1H, d, J = 8.1 Hz), 3.87 (3H, s), 2.62 (3H, s), 1.33 (9H, s); LRMS (ESI) m/z 480 [M + H]$^+$. |
| 94 | 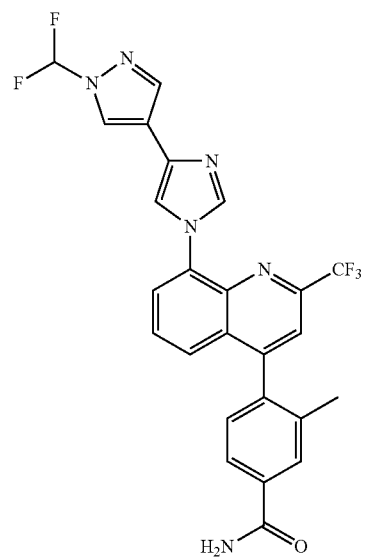 [SMILES: Cc1cc(C(N)=O)ccc1-c1cc(C(F)(F)F)nc2c(-n3cnc(-c4cnn(C(F)F)c4)c3)cccc12] | $^1$H-NMR (DMSO-d$_6$): δ 8.47 (1H, s), 8.36 (1H, s), 7.85-8.15 (9H, m), 7.53 (1H, d, J = 8.3 Hz), 7.49 (1H, br s), 7.43 (1H, d, J = 7.8 Hz), 2.06 (3H, s); LRMS (ESI) m/z 513 [M + H]$^+$. |
| 95 | 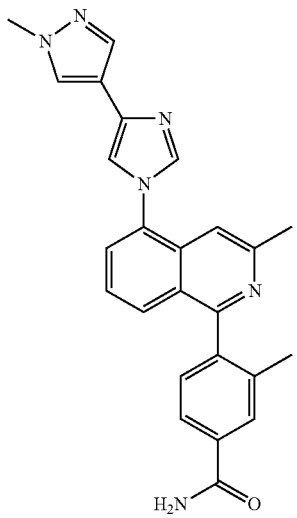 | $^1$H-NMR (DMSO-d$_6$): δ 8.07 (1H, br s), 8.03 (1H, d, J = 1.2 Hz), 7.97 (1H, s), 7.94 (1H, s), 7.87 (1H, s), 7.85 (1H, s), 7.77 (1H, d, J = 1.2 Hz), 7.74 (1H, s), 7.56-7.66 (2H, m), 7.45 (1H, br s), 7.36-7.40 (2H, m), 3.88 (3H, s), 2.63 (3H, s), 2.05 (3H, s); LRMS (ESI) m/z 423 [M + H]$^+$. |

TABLE 20
| | | |
|---|---|---|
| 96 | 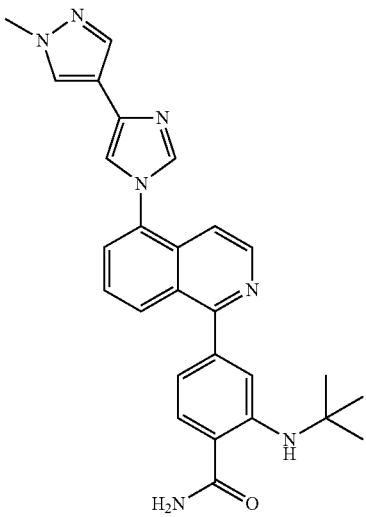 [SMILES: Cn1cc(-c2cn(-c3cccc4c(-c5ccc(C(N)=O)c(NC(C)(C)C)c5)nccc34)cn2)cn1] | ¹H-NMR (DMSO-d₆): δ 8.66 (1H, d, J = 5.9 Hz), 8.49 (1H, s), 8.19 (1H, d, J = 8.3 Hz), 7.90-8.05 (4H, m), 7.71-7.81 (4H, m), 7.52 (1H, d, J = 5.9 Hz), 7.26 (1H, br s), 7.09 (1H, s), 3.87 (3H, s), 1.35 (9H, s) ; LRMS (ESI) m/z 466 [M + H]⁺. |
| 97 | 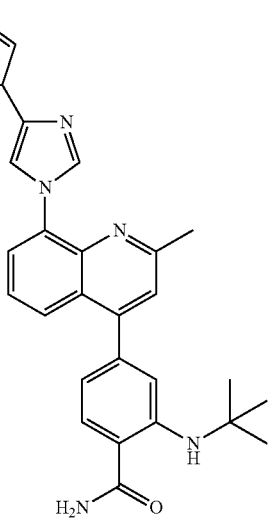 | ¹H-NMR (DMSO-d₆): δ 8.53 (1H, s), 8.24 (1H, d, J = 1.2 Hz), 7.85-8.00 (4H, m), 7.82 (1H, d, J = 1.2 Hz), 7.77 (1H, d, J = 8.1 Hz), 7.72 (1H, s), 7.63 (1H, t, J = 7.9 Hz), 7.49 (1H, s), 7.26 (1H, br s), 6.91 (1H, d, J = 1.2 Hz), 6.65 (1H, d, J = 8.1 Hz), 3.87 (3H, s), 2.70 (3H, s), 1.34 (9H, s); LRMS (ESI) m/z 480 [M + H]⁺. |
| 98 | 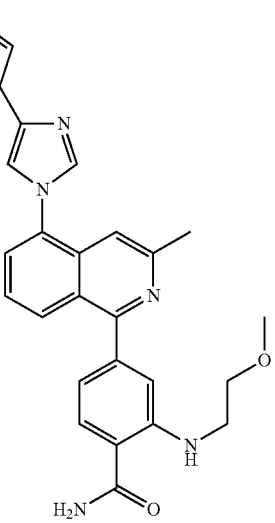 | ¹H-NMR (DMSO-d₆): δ 8.36 (1H, br s), 8.10 (1H, d, J = 8.8 Hz), 7.63-8.02 (8H, m), 7.33 (1H, s), 7.24 (1H, br s), 6.89 (1H, s), 6.77 (1H, d, J = 8.1 Hz), 3.87 (3H, s), 3.48-3.58 (2H, m), 2.62 (3H, s); LRMS (ESI) m/z 482 [M + H]⁻. |

TABLE 20-continued
| 99 | 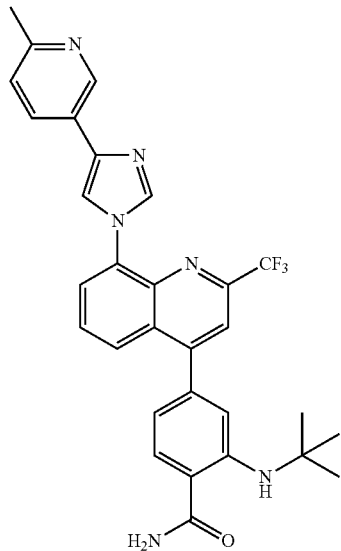 [SMILES: Cc1ccc(-c2cn(-c3cccc4c(-c5ccc(C(N)=O)c(NC(C)(C)C)c5)cc(C(F)(F)F)nc34)cn2)cn1] | ¹H-NMR (DMSO-d₆): δ 8.97 (1H, d, J = 2.0 Hz), 8.58 (1H, s), 8.39 (1H, d, J = 1.2 Hz), 8.34 (1H, d, J = 1.2 Hz), 8.17 (1H, d, J = 7.3 Hz), 7.90-8.20 (7H, m), 7.81 (1H, d, J = 8.1 Hz), 7.31 (1H, d, J = 8.1 Hz), 7.31 (1H, br s), 6.99 (1H, d, J = 1.5 Hz), 6.74 (1H, dd, J = 7.9, 1.6 Hz), 2.06 (3H, s), 1.35 (9H, s); LRMS (ESI) m/z 545 [M + H]⁺. |
|---|---|---|
| 100 | 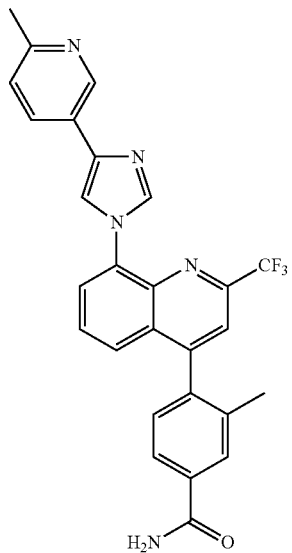 [SMILES: Cc1ccc(-c2cn(-c3cccc4c(-c5ccc(C(N)=O)cc5C)cc(C(F)(F)F)nc34)cn2)cn1] | ¹H-NMR (DMSO-d₆): δ 8.97 (1H, s), 8.42 (1H, s), 8.36 (1H, s), 7.85-8.23 (7H, m), 7.54 (1H, d, J = 8.5 Hz), 7.49 (1H, br s), 7.43 (1H, d, J = 7.8 Hz), 7.31 (1H, d, J = 8.1 Hz), 2.06 (3H, s); LRMS (ESI) m/z 488 [M + H]⁺. |

TABLE 21
| | | |
|---|---|---|
| 101 | 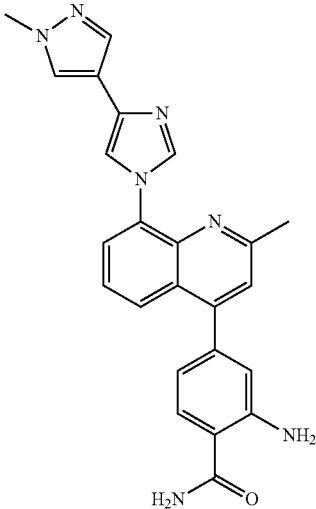 | ¹H-NMR (DMSO-d₆): δ 8.24 (1H, s), 7.60-7.96 (8H, m), 7.46 (1H, s), 7.20 (1H, br s), 6.85 (1H, s), 6.80 (2H, br s), 6.63 (1H, d, J = 8.1 Hz), 3.87 (3H, s), 2.69 (3H, s); LRMS (ESI) m/z 424 [M + H]⁺. |
| 102 | 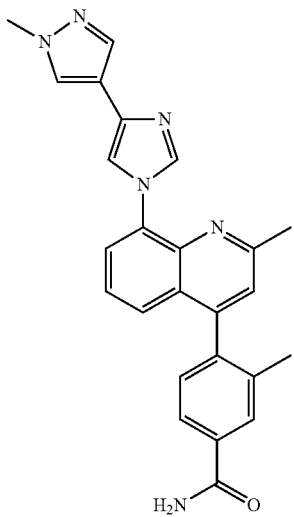 | ¹H-NMR (DMSO-d₆): δ 8.27 (1H, d, J = 1.2 Hz), 8.06 (1H, br s), 7.95 (2H, s), 7.83-7.89 (3H, m), 7.73 (1H, s), 7.58 (1H, t, J = 7.9 Hz), 7.44 (2H, s), 7.34 (1H, d, J = 7.6 Hz), 3.87 (3H, s), 2.70 (3H, s), 2.05 (3H, s); LRMS (ESI) m/z 423 [M + H]⁺. |
| 103 | 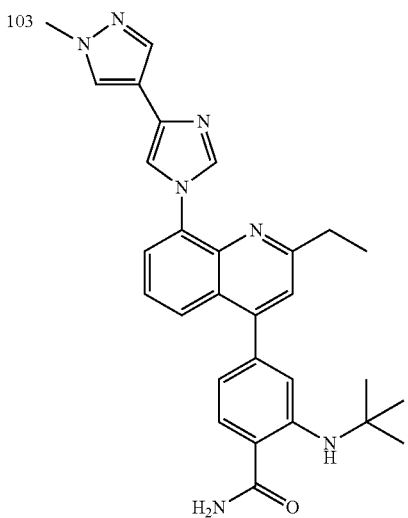 | ¹H-NMR (DMSO-d₆): δ 8.53 (1H, s), 8.30 (1H, s), 7.59-8.00 (5H, m), 7.77 (1H, d, J = 8.1 Hz), 7.72 (1H, s), 7.64 (1H, t, J = 7.9 Hz), 7.49 (1H, s), 7.26 (1H, br s), 6.92 (1H, s), 6.66 (1H, d, J = 7.8 Hz), 3.87 (3H, s), 3.01 (2H, q, J = 7.5 Hz), 1.30-1.40 (12H, m); LRMS (ESI) m/z 494 [M + H]⁺. |

TABLE 21-continued
| | | |
|---|---|---|
| 104 | 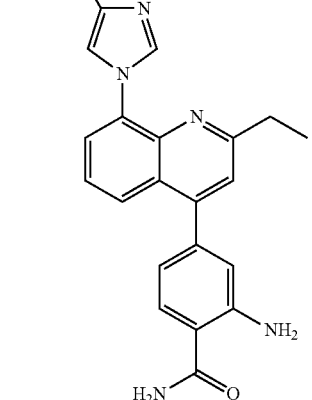 | ¹H-NMR (DMSO-d₆): δ 8.30 (1H, d, J = 1.0 Hz), 7.94 (1H, s), 7.84-7.93 (4H, m), 7.70-7.75 (2H, m), 7.64 (1H, t, J = 7.9 Hz), 7.46 (1H, s), 7.20 (1H, br s), 6.85 (1H, d, J = 1.2 Hz), 6.80 (2H, br s), 6.64 (1H, dd, J = 8.2, 1.6 Hz), 3.87 (3H, s), 2.99 (2H, q, J = 7.5 Hz), 1.33 (1H, t, J = 7.4 Hz); LRMS (ESI) m/z 438 [M + H]⁺. |
| 105 | | ¹H-NMR (DMSO-d₆): δ 8.53 (1H, s), 8.23 (1H, s), 7.70-7.79 (7H, m), 7.53-7.62 (2H, m), 7.26 (1H, br s), 6.91 (1H, s), 6.66 (1H, d, J = 7.6 Hz), 3.88 (3H, s), 2.35-2.45 (1H, m), 1.34 (9H, s); LRMS (ESI) m/z 506 [M + H]⁺. |
TABLE 22
| | | |
|---|---|---|
| 106 | 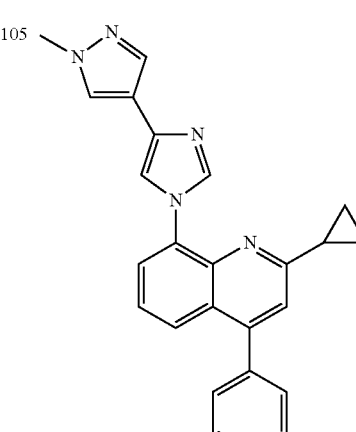 | ¹H-NMR (DMSO-d₆): δ 8.20 (1H, s), 7.94 (1H, s), 7.79-7.88 (4H, m), 7.69-7.75 (2H, m), 7.58 (1H, t, J = 7.9 Hz), 7.52 (1H, s), 7.20 (1H, br s), 6.85 (1H, s), 6.79 (2H, br s), 6.64 (1H, d, J = 7.8 Hz), 3.87 (3H, s), 2.35-2.45 (1H, m), 1.02-1.12 (4H, m); LRMS (ESI) m/z 450 [M + H]⁺. |

| | | |
|---|---|---|
| 107 | 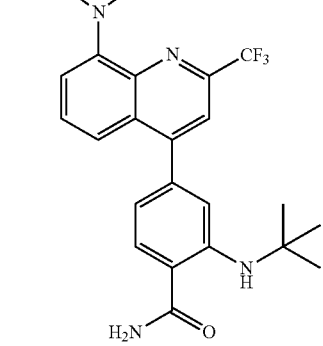 | ¹H-NMR (DMSO-d₆): δ 8.58 (1H, s), 8.36 (1H, s), 8.27 (1H, s), 8.17 (1H, d, J = 7.1 Hz), 7.60-8.19 (6H, m), 7.81 (1H, d, J = 8.1 Hz), 7.42 (2H, t, J = 7.6 Hz), 7.31 (1H, br s), 7.26 (1H, t, J = 7.3 Hz), 6.99 (1H, s), 6.74 (1H, d, J = 8.1 Hz), 1.35 (9H, s); LRMS (ESI) m/z 474 [M + H]⁺. |
| 108 | 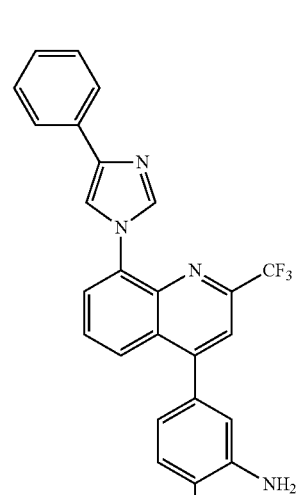 | ¹H-NMR (DMSO-d₆): δ 8.36 (1H, s), 8.28 (1H, s), 8.18 (1H, d, J = 7.3 Hz), 8.06 (1H, d, J = 8.8 Hz), 7.85-7.99 (5H, m), 7.77 (1H, d, J = 8.1 Hz), 7.42 (2H, t, J = 7.6 Hz), 7.26 (1H, t, J = 7.3 Hz), 6.93 (1H, s), 6.86 (2H, br s), 6.72 (1H, d, J = 8.1 Hz); LRMS (ESI) m/z 474 [M + H]⁺. |
| 109 | 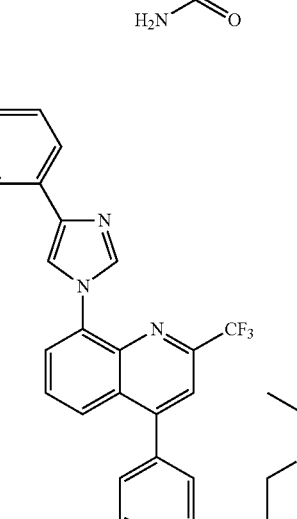 | ¹H-NMR (DMSO-d₆): δ 8.48 (1H, s), 8.36 (1H, s), 8.27 (1H, s), 8.18 (1H, d, J = 7.6 Hz), 7.79-8.10 (7H, m), 7.22-7.46 (4H, m), 6.90 (1H, s), 6.75 (1H, d, J = 7.8 Hz), 3.50-3.68 (3H, m), 3.26-3.48 (5H, m), 1.10 (1H, d, J = 6.1 Hz); LRMS (ESI) m/z 560 [M + H]⁺. |

TABLE 22-continued
| 110 | 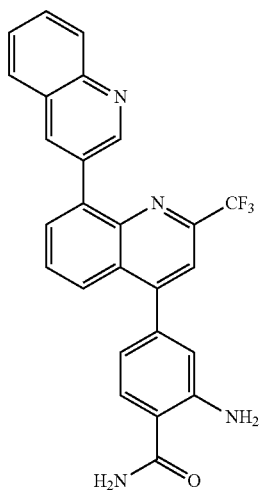 [SMILES: NC(=O)c1ccc(-c2cc(C(F)(F)F)nc3c(-c4cnc5ccccc5c4)cccc23)cc1N] | ¹H-NMR (DMSO-d₆): δ 9.28 (1H, d, J = 2.2 Hz), 8.67 (1H, d, J = 2.0 Hz), 8.21 (1H, d, J = 6.8 Hz), 8.06-8.15 (3H, m), 7.88-7.99 (3H, m), 7.84 (1H, t, J = 7.2 Hz), 7.78 (1H, d, J = 8.1 Hz), 7.69 (1H, t, J = 7.6 Hz), 7.25 (1H, br s), 6.95 (1H, d, J = 1.5 Hz), 6.85 (2H, br s), 6.74 (1H, dd, J = 8.2, 1.9 Hz); LRMS (ESI) m/z 459 [M + H]⁺. |
TABLE 23
| 111 | 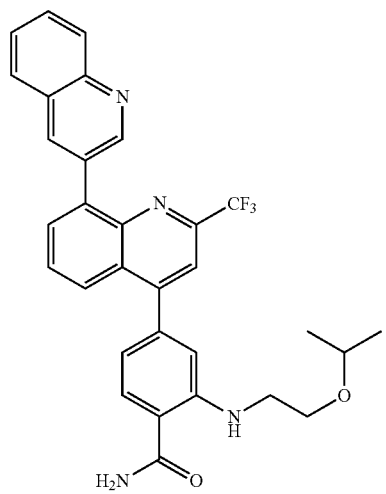 [SMILES: CC(C)OCCNc1cc(-c2cc(C(F)(F)F)nc3c(-c4cnc5ccccc5c4)cccc23)ccc1C(N)=O] | ¹H-NMR (DMSO-d₆): δ 9.27 (1H, s), 8.67 (1H, s), 8.48 (1H, br s), 8.21 (1H, d, J = 6.3 Hz), 7.65-8.16 (9H, m), 7.31 (1H, br s), 6.91 (1H, s), 6.77 (1H, d, J = 7.3 Hz), 3.50-3.60 (3H, m), 3.24-3.42 (5H, m), 1.02-1.04 (6H, d, J = 6.6 Hz); LRMS (ESI) m/z 545 [M + H]⁺. |
| 112 | 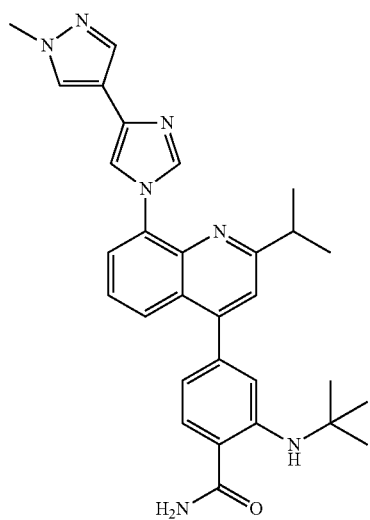 [SMILES: CC(C)c1cc(-c2ccc(C(N)=O)c(NC(C)(C)C)c2)c2cccc(-n3cnc(-c4cnn(C)c4)c3)c2n1] | ¹H-NMR (DMSO-d₆): δ 8.54 (1H, s), 8.34 (1H, s), 7.85-8.00 (5H, m), 7.77 (1H, d, J = 8.3 Hz), 7.72 (1H, s), 7.65 (1H, t, J = 7.9 Hz), 7.52 (1H, s), 7.27 (1H, br s), 6.92 (1H, s), 6.67 (1H, d, J = 7.3 Hz), 3.87 (3H, s), 1.25-1.43 (15H, m); LRMS (ESI) m/z 508 [M + H]⁺. |

TABLE 23-continued
| 113 | 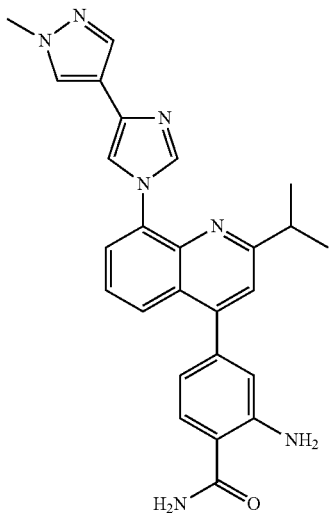 [SMILES: CC(C)c1cc(-c2ccc(C(N)=O)c(N)c2)c2cccc(-n3cnc(-c4cnn(C)c4)c3)c2n1] | $^1$H-NMR (DMSO-d$_6$): δ 8.34 (1H, s), 7.83-7.96 (5H, m), 7.70-7.75 (2H, m), 7.64 (1H, t, J = 8.1 Hz), 7.50 (1H, s), 7.21 (1H, br s), 6.86 (1H, s), 6.80 (2H, br s), 6.64 (1H, d, J = 9.3 Hz), 3.87 (3H, s), 3.20-3.35 (1H, m), 1.33 (6H, d, J = 6.8 Hz); LRMS (ESI) m/z 452 [M + H]$^+$. |
|---|---|---|
| 114 | 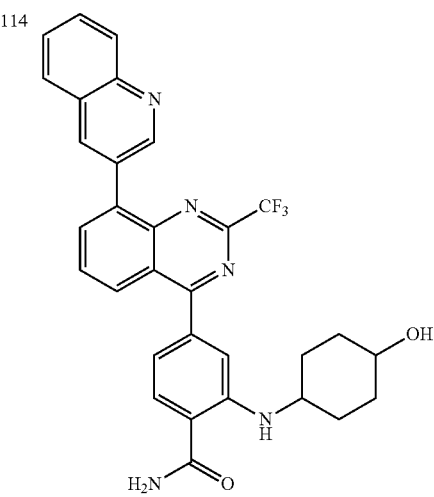 | $^1$H-NMR (DMSO-d$_6$): δ 9.31 (1H, d, J = 2.2 Hz), 8.73 (1H, d, J = 2.0 Hz), 8.48 (1H, d, J = 7.1 Hz), 8.34 (1H, d, J = 7.6 Hz), 8.29 (1H, d, J = 8.5 Hz), 8.16-7.98 (4H, m), 7.89-7.82 (2H, m), 7.71 (1H, t, J = 7.6 Hz), 7.36 (1H, br s), 7.10 (1H, s), 6.90 (1H, d, J = 8.1 Hz), 4.52 (1H, d, J = 4.4 Hz), 3.52-3.44 (1H, m), 3.39-3.32 (1H, m), 2.07-1.95 (2H, m), 1.89-1.71 (2H, m), 1.32-1.20 (4H, m); LRMS (ESI) m/z 558 [M + H]$^+$. |
| 115 | 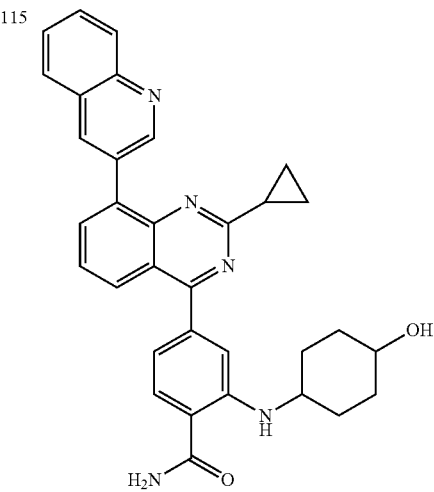 | $^1$H-NMR (DMSO-d$_6$): δ 9.30 (1H, d, J = 1.7 Hz), 8.67 (1H, s), 8.29 (1H, d, J = 7.6 Hz), 8.21 (1H, d, J = 7.1 Hz), 8.14-8.04 (3H, m), 7.99 (1H, br s), 7.85-7.67 (4H, m), 7.30 (1H, br s), 7.02 (1H, s), 6.83 (1H, d, J = 8.1 Hz), 4.52 (1H, d, J = 4.1 Hz), 3.52-3.44 (1H, m), 3.39-3.32 (1H, m), 2.36-2.28 (1H, m), 2.07-1.95 (2H, m), 1.89-1.71 (2H, m), 1.32-1.20 (4H, m), 1.13-1.04 (4H, m); LRMS (ESI) m/z 530 [M + H]$^+$. |

TABLE 24

| | | |
|---|---|---|
| 116 | *(structure)* | ¹H-NMR (DMSO-d₆): δ 9.35 (1H, d, J = 2.2 Hz), 8.71 (1H, s), 8.32 (1H, d, J = 5.9 Hz), 8.26 (1H, d, J = 7.3 Hz), 8.14-8.08 (3H, m), 7.99 (1H, br s), 7.86-7.79 (3H, m), 7.69 (1H, t, J = 7.7 Hz), 7.30 (1H, br s), 7.03 (1H, s), 6.84 (1H, d, J = 7.8 Hz), 4.52 (1H, d, J = 4.4 Hz), 3.52-3.44 (1H, m), 3.39-3.32 (1H, m), 3.07 (2H, q, J = 7.5 Hz), 2.07-1.95 (2H, m), 1.89-1.71 (2H, m), 1.34 (3H, t, J = 7.6 Hz), 1.32-1.20 (4H, m); LRMS (ESI) m/z 518 [M + H]⁺. |
| 117 | *(structure)* | ¹H-NMR (DMSO-d₆): δ 9.22 (1H, d, J = 2.0 Hz), 8.96 (1H, d, J = 4.4 Hz), 8.59 (1H, s), 8.34 (1H, d, J = 7.9 Hz), 7.70-8.14 (8H, m), 7.67 (1H, t, J = 7.4 Hz), 7.55 (1H, d, J = 4.4 Hz), 7.25 (1H, br s), 6.83 (1H, s), 6.66 (1H, d, J = 8.1 Hz), 451 (1H, d, J = 4.2 Hz), 3.30-3.60 (2H, m), 1.75-2.05 (4H, m), 1.20-1.35 (4H, m); LRMS (ESI) m/z 489 [M + H]⁺. |
| 118 | *(structure)* | ¹H-NMR (DMSO-d₆): δ 8.96 (1H, d, J = 1.7 Hz), 8.39 (1H, d, J = 1.2 Hz), 8.34 (1H, d, J = 1.0 Hz), 8.18 (1H, d, J = 7.6 Hz), 7.85-8.13 (5H, m), 7.77 (1H, d, J = 8.1 Hz), 7.30 (1H, d, J = 8.1 Hz), 7.25 (1H, br s), 6.93 (1H, d, J = 1.5 Hz), 6.85 (2H, br s), 6.72 (1H, dd, J = 8.2, 1.6 Hz), 2.49 (3H, s); LRMS (ESI) m/z 489 [M + H]⁺. |

TABLE 24-continued
| 119 | 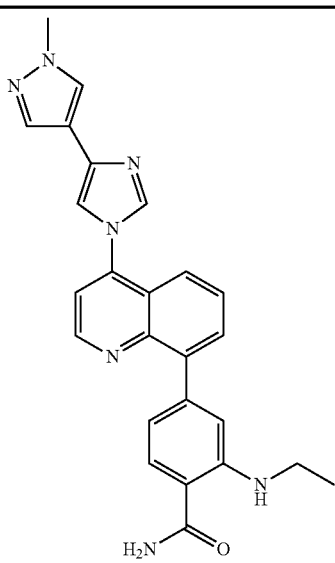 | $^1$H-NMR (DMSO-$d_6$): δ 9.01 (1H, d, J = 4.6 Hz), 8.17-8.08 (2H, m), 8.00 (1H, s), 7.93-7.66 (8H, m), 7.17 (1H, br s), 6.88 (1H, s), 6.79 (1H, d, J = 8.3 Hz), 3.88 (3H, s), 3.21-3.10 (2H, m), 1.21 (3H, t, J = 7.1 Hz). |
|---|---|---|
| 120 | 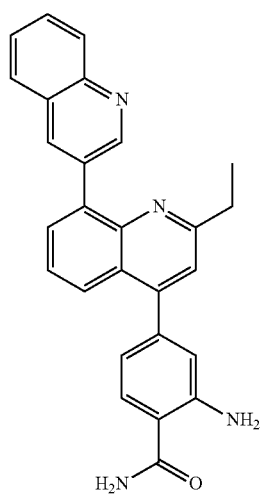 [SMILES: CCc1cc(-c2ccc(C(N)=O)c(N)c2)c2cccc(-c3cnc4ccccc4c3)c2n1] | $^1$H-NMR (DMSO-$d_6$): δ 9.32 (1H, s), 8.63 (1H, s), 7.60-8.20 (9H, m), 7.41 (1H, s), 7.20 (1H, br s), 6.87 (1H, s), 6.80 (2H, br s), 6.66 (1H, d, J = 7.8 Hz), 2.92 (2H, q, J = 7.6 Hz), 1.28 (3H, t, J = 7.3 Hz); LRMS (ESI) m/z 419 [M + H]$^+$. |
TABLE 25
| 121 | 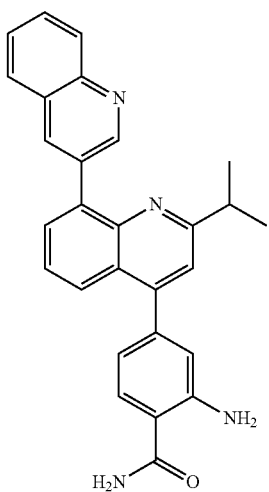 [SMILES: CC(C)c1cc(-c2ccc(C(N)=O)c(N)c2)c2cccc(-c3cnc4ccccc4c3)c2n1] | $^1$H-NMR (DMSO-$d_6$): δ 9.35 (1H, d, J = 2.2 Hz), 8.67 (1H, d, J = 2.0 Hz), 7.62-8.12 (9H, m), 7.44 (1H, s), 7.20 (1H, br s), 6.88 (1H, d, J = 1.5 Hz), 6.82 (1H, br s), 6.67 (1H, dd, J = 8.1, 1.7 Hz), 3.20-3.30 (1H, m), 1.27 (6H, d, J = 6.8 Hz); LRMS (ESI) m/z 433 [M + H]$^+$. |
|---|---|---|

TABLE 25-continued
| 122 | 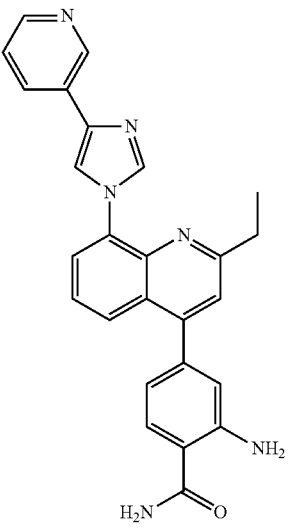 [SMILES: CCc1cc(-c2ccc(C(N)=O)c(N)c2)c2cccc(-n3cnc(-c4cccnc4)c3)c2n1] | $^1$H-NMR (DMSO-d$_6$): δ 9.11 (1H, d, J = 2.2 Hz), 8.38-8.50 (3H, m), 8.22 (1H, d, J = 7.8 Hz), 7.81-8.02 (3H, m), 7.73 (1H, d, J = 8.1 Hz), 7.67 (1H, t, J = 8.1 Hz), 7.49 (1H, s), 7.44 (1H, dd, J = 7.8, 4.9 Hz), 7.21 (1H, br s), 6.86 (1H, d, J = 1.2 Hz), 6.81 (2H, br s), 6.65 (1H, d, J = 8.1 Hz), 3.00 (2H, q, J = 7.4 Hz), 1.34 (3H, t, J = 7.6 Hz); LRMS (ESI) m/z 435 [M + H]$^+$. |
|---|---|---|
| 123 | 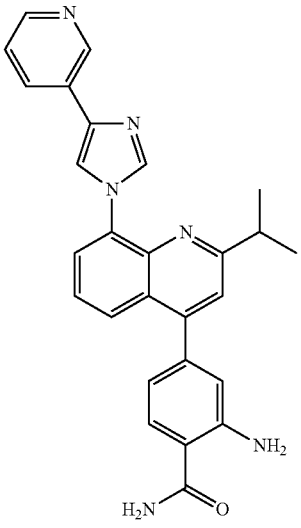 [SMILES: CC(C)c1cc(-c2ccc(C(N)=O)c(N)c2)c2cccc(-n3cnc(-c4cccnc4)c3)c2n1] | $^1$H-NMR (DMSO-d$_6$): δ 9.14 (1H, s), 8.35-8.60 (3H, m), 8.26 (1H, d, J = 7.6 Hz), 7.80-8.04 (3H, m), 7.63-7.78 (2H, m), 7.4-7.58 (2H, m), 7.21 (1H, br s), 6.82-6.93 (3H, m), 6.65 (1H, d, J = 8.3 Hz), 3.20-3.48 (1H, m), 1.33 (6H, d, J = 6.8 Hz); LRMS (ESI) m/z 449 [M + H]$^+$. |
| 124 | 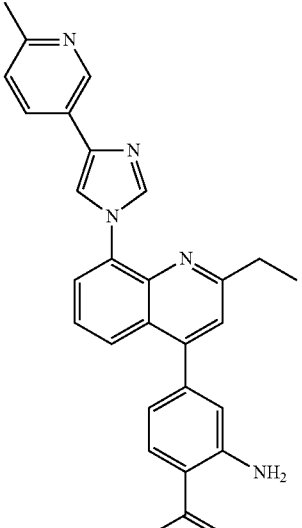 | $^1$H-NMR (DMSO-d$_6$): δ 8.97 (1H, s), 8.41 (1H, s), 8.33 (1H, s), 8.10 (1H, dd, J = 7.8, 2.0 Hz), 7.82-7.99 (3H, m), 7.73 (1H, d, J = 8.1 Hz), 7.67 (1H, t, J = 7.8 Hz), 7.48 (1H, s), 7.29 (1H, d, J = 8.1 Hz), 7.21 (1H, br s), 6.86 (1H, s), 6.81 (2H, br s), 6.64 (1H, d, J = 8.1 Hz), 2.99 (2H, q, J = 7.6 Hz), 2.49 (3H, s), 1.34 (3H, t, J = 7.6 Hz); LRMS (ESI) m/z 449 [M + H]$^+$. |

TABLE 25-continued

| 125 | 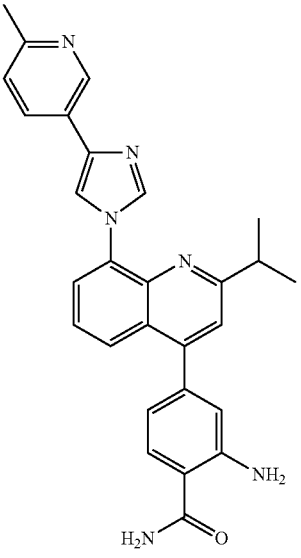 [SMILES: Cc1ccc(-c2cn(-c3cccc4c(-c5ccc(C(N)=O)c(N)c5)cc(C(C)C)nc34)cn2)cn1] | ¹H-NMR (DMSO-d₆): δ 8.97 (1H, d, J = 2.0 Hz), 8.44 (1H, s), 8.35 (1H, s), 8.10 (1H, dd, J = 8.1, 1.7 Hz), 7.97 (1H, d, J = 7.6 Hz), 7.83-7.95 (2H, m), 7.73 (1H, d, J = 8.1 Hz), 7.67 (1H, t, J = 8.1 Hz), 7.51 (1H, s), 7.31 (1H, d, J = 8.3 Hz), 7.21 (1H, br s), 6.87 (1H, s), 6.81 (2H, br s), 6.65 (1H, d, J = 8.1 Hz), 3.20-3.48 (1H, m), 2.49 (3H, s), 1.33 (6H, d, J = 7.1 Hz); LRMS (ESI) m/z 463 [M + H]⁺. |

TABLE 26

| 126 | 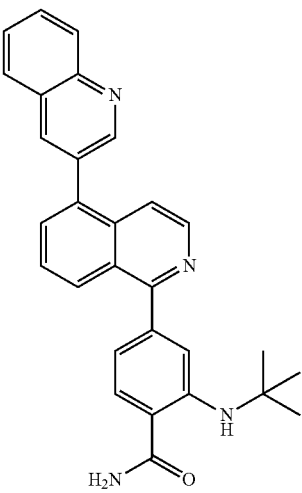 [SMILES: CC(C)(C)Nc1cc(-c2nccc3c(-c4cnc5ccccc5c4)cccc23)ccc1C(N)=O] | ¹H-NMR (DMSO-d₆): δ 9.07 (1H, d, J = 2.2 Hz), 8.58-8.61 (2H, m), 8.49 (1H, s), 8.09-8.21 (3H, m), 7.69-7.99 (7H, m), 7.25 (1H, br s), 7.11 (1H, d, J = 1.5 Hz), 6.81 (1H, dd, J = 7.9, 1.3 Hz), 1.36 (9H, s); LRMS (ESI) m/z 447 [M + H]⁺. |
| 127 | 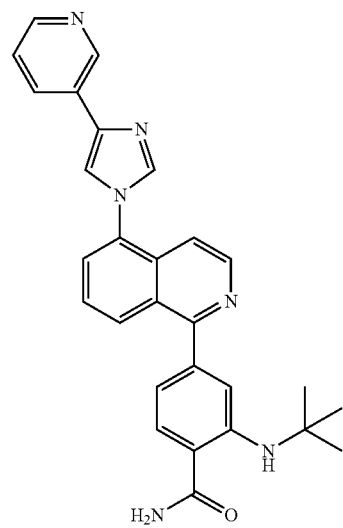 [SMILES: CC(C)(C)Nc1cc(-c2nccc3c(-n4cnc(-c5cccnc5)c4)cccc23)ccc1C(N)=O] | ¹H-NMR (DMSO-d₆): δ 9.12 (1H, d, J = 2.2 Hz), 8.68 (1H, d, J = 6.1 Hz), 8.50 (1H, s), 8.47 (1H, dd, J = 4.8, 1.3 Hz), 8.31 (13-(tert-butylamino)-4-cyanophenylboronic acid pinacol ester H, s), 8.19-8.16 (3H, m), 8.00 (1H, d, J = 7.3 Hz), 7.96 (1H, br s), 7.75-7.83 (2H, m), 7.54 (1H, d, J = 5.9 Hz), 7.45 (1H, dd, J = 7.9, 4.8 Hz), 7.27 (1H, br s), 7.09 (1H, s), 6.79 (1H, d, J = 8.1 Hz), 1.35 (9H, s); LRMS (ESI) m/z 463 [M + H]⁺. |

TABLE 26-continued
| | | |
|---|---|---|
| 128 | 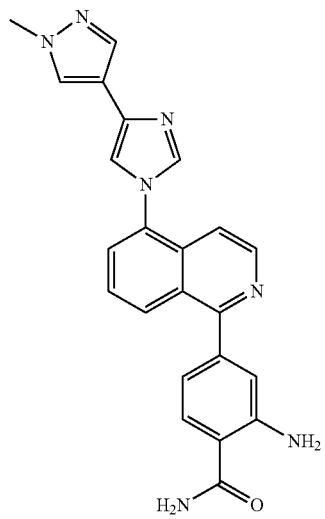 [SMILES: Cn1cc(-c2cn(-c3cccc4c(-c5ccc(C(N)=O)c(N)c5)nccc34)cn2)cn1] | ¹H-NMR (DMSO-d₆): δ 8.64 (1H, d, J = 5.9 Hz), 8.17 (1H, d, J = 8.5 Hz), 8.02 (1H, s), 7.97 (1H, s), 7.93 (1H, d, J = 7.1 Hz), 7.88 (1H, br s), 7.70-7.80 (4H, m), 7.51 (1H, d, J = 6.1 Hz), 7.20 (1H, br s), 7.00 (1H, d, J = 1.5 Hz), 6.73-6.82 (3H, m), 3.87 (3H, s); LRMS (ESI) m/z 410 [M + H]⁺. |
| 129 | 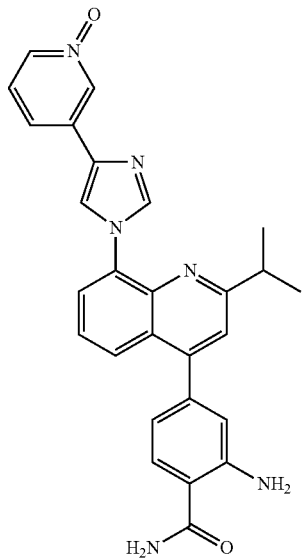 [SMILES: CC(C)c1cc(-c2ccc(C(N)=O)c(N)c2)c2cccc(-n3cnc(-c4ccc[n+]([O-])c4)c3)c2n1] | ¹H-NMR (DMSO-d₆): δ 8.71 (1H, s), 8.51 (1H, s), 8.46 (1H, s), 8.11 (1H, d, J = 6.3 Hz), 8.02-7.85 (3H, m), 7.81 (1H, d, J = 8.1 Hz), 7.74 (1H, d, J = 8.1 Hz), 7.69 (1H, t, J = 7.9 Hz), 7.52 (1H, s), 7.47 (1H, t, J = 7.2 Hz), 7.22 (1H, br s), 6.87 (1H, s), 6.82 (2H, s), 6.66 (1H, d, J = 8.1 Hz), 3.30-3.22 (1H, m), 1.33 (6H, d, J = 6.8 Hz); LRMS (ESI) m/z 465 [M + H]⁺. |
| 130 | 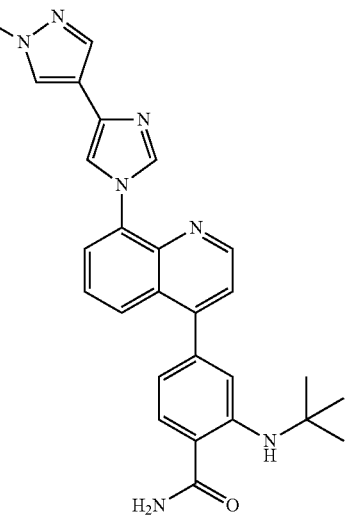 | ¹H-NMR (DMSO-d₆): δ 9.02 (1H, d, J = 3.9 Hz), 8.54 (1H, s), 8.18 (1H, s), 8.02-7.92 (4H, m), 7.83-7.70 (4H, m), 7.61 (1H, d, J = 4.1 Hz), 7.27 (1H, br s), 6.94 (1H, s), 6.68 (1H, d, J = 8.1 Hz), 3.88 (3H, s), 1.35 (9H, s); LRMS (ESI) m/z 466 [M + H]⁺. |

TABLE 27
| | | |
|---|---|---|
| 131 | 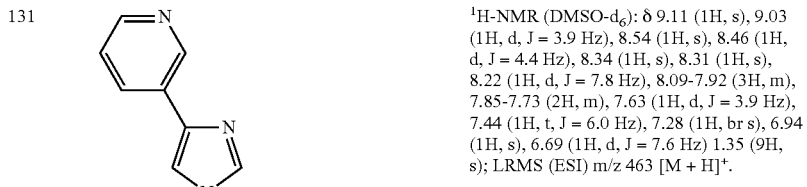 | ¹H-NMR (DMSO-d₆): δ 9.11 (1H, s), 9.03 (1H, d, J = 3.9 Hz), 8.54 (1H, s), 8.46 (1H, d, J = 4.4 Hz), 8.34 (1H, s), 8.31 (1H, s), 8.22 (1H, d, J = 7.8 Hz), 8.09-7.92 (3H, m), 7.85-7.73 (2H, m), 7.63 (1H, d, J = 3.9 Hz), 7.44 (1H, t, J = 6.0 Hz), 7.28 (1H, br s), 6.94 (1H, s), 6.69 (1H, d, J = 7.6 Hz) 1.35 (9H, s); LRMS (ESI) m/z 463 [M + H]⁺. |
| 132 | 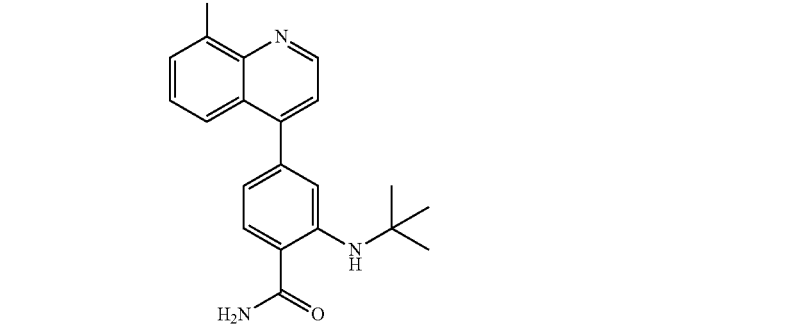 | ¹H-NMR (DMSO-d₆): δ 9.01 (1H, d, J = 4.1 Hz), 8.17 (1H, s), 8.00-7.80 (5H, m), 7.77-7.69 (3H, m), 7.56 (1H, d, J = 4.4 Hz), 7.21 (1H, br s), 6.89-6.78 (3H, m) 6.65 (1H, d, J = 9.0 Hz), 3.88 (3H, s); LRMS (ESI) m/z 410 [M + H]⁺. |
| 133 | 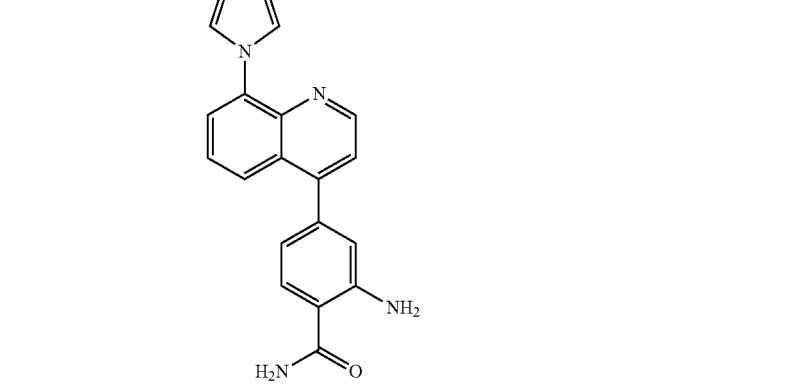 | ¹H-NMR (DMSO-d₆): δ 9.02 (1H, d, J = 4.4 Hz), 8.36-8.20 (4H, m), 8.04-7.97 (2H, m), 7.88 (1H, br s), 7.81-7.72 (2H, m), 7.63-7.32 (3H, m), 7.22 (1H, br s), 6.88 (1H, s), 6.83 (2H, s), 6.66 (1H, d, J = 8.3 Hz); LRMS (ESI) m/z 407 [M + H]⁺. |

TABLE 27-continued
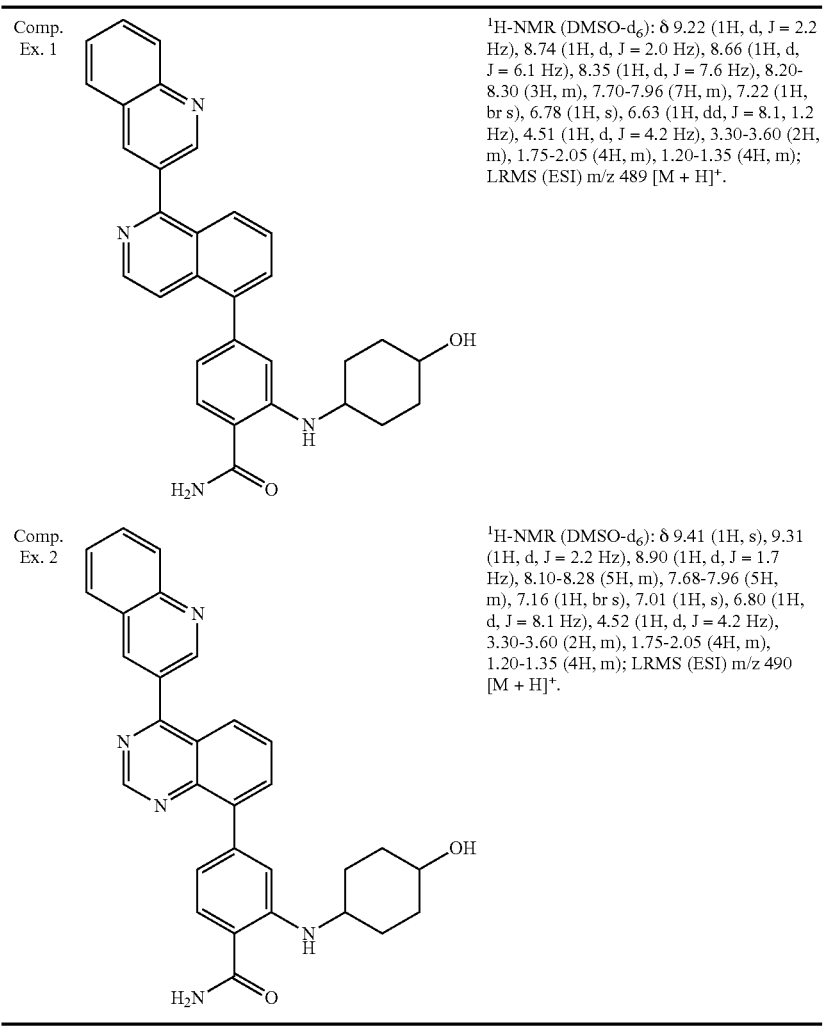
| Comp. Ex. 1 | ¹H-NMR (DMSO-d₆): δ 9.22 (1H, d, J = 2.2 Hz), 8.74 (1H, d, J = 2.0 Hz), 8.66 (1H, d, J = 6.1 Hz), 8.35 (1H, d, J = 7.6 Hz), 8.20-8.30 (3H, m), 7.70-7.96 (7H, m), 7.22 (1H, br s), 6.78 (1H, s), 6.63 (1H, dd, J = 8.1, 1.2 Hz), 4.51 (1H, d, J = 4.2 Hz), 3.30-3.60 (2H, m), 1.75-2.05 (4H, m), 1.20-1.35 (4H, m); LRMS (ESI) m/z 489 [M + H]⁺. |
|---|---|
| Comp. Ex. 2 | ¹H-NMR (DMSO-d₆): δ 9.41 (1H, s), 9.31 (1H, d, J = 2.2 Hz), 8.90 (1H, d, J = 1.7 Hz), 8.10-8.28 (5H, m), 7.68-7.96 (5H, m), 7.16 (1H, br s), 7.01 (1H, s), 6.80 (1H, d, J = 8.1 Hz), 4.52 (1H, d, J = 4.2 Hz), 3.30-3.60 (2H, m), 1.75-2.05 (4H, m), 1.20-1.35 (4H, m); LRMS (ESI) m/z 490 [M + H]⁺. |
TABLE 28
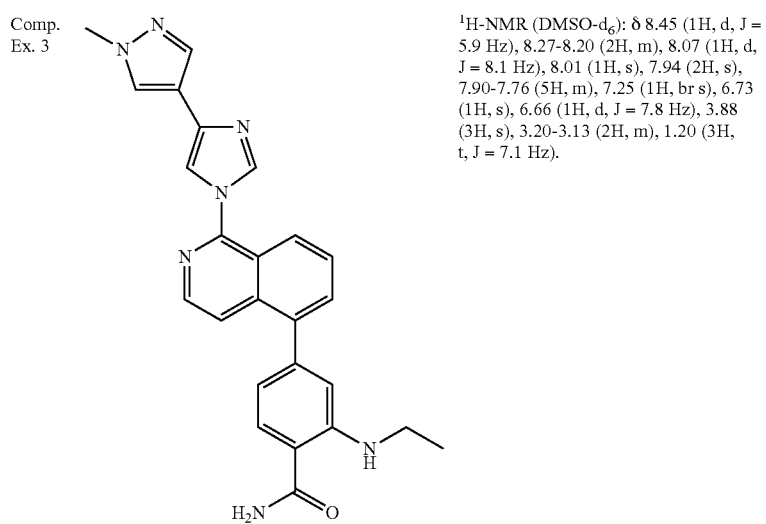
| Comp. Ex. 3 | ¹H-NMR (DMSO-d₆): δ 8.45 (1H, d, J = 5.9 Hz), 8.27-8.20 (2H, m), 8.07 (1H, d, J = 8.1 Hz), 8.01 (1H, s), 7.94 (2H, s), 7.90-7.76 (5H, m), 7.25 (1H, br s), 6.73 (1H, s), 6.66 (1H, d, J = 7.8 Hz), 3.88 (3H, s), 3.20-3.13 (2H, m), 1.20 (3H, t, J = 7.1 Hz). |
|---|---|

Test Example 1

Determination of HSP90-Binding Activity

First, a purified HSP90 solution was prepared as follows: a human HSP90 alpha gene (NCBI Reference Sequence accession no. NM_005348) region corresponding to amino acids 2 to 236 of human HSP90 alpha protein (NCBI Reference Sequence accession no. NP_005339; full length: 732 amino acids) was inserted to pET-19b (Novagen; Merck KGaA) to construct a plasmid pET-HSP90N for expression of the HSP90 N-terminal protein having a His-tag at the N-terminus. *E. coli* (BL21(DE3), Stratagene Corp.) was transformed with pET-HSP90N and then cultured at 37° C. for 4 hours in the presence of 0.5 mM isopropyl-beta-D-thiogalactopyranoside (Sigma-Aldrich Corp.). The collected *E. coli* was suspended in a lysis buffer (50 mM Tris-HCl (pH 7.5), 200 mM NaCl) and sonicated. The sonicated cell solution was centrifuged (40,000×g, 20 minutes), and the supernatant was used as a crude extract. This crude extract was fractionated using Ni Sepharose High Performance (GE Healthcare Japan Corp.) chromatography and HiLoad 26/60 Superdex 75 pg (GE Healthcare Japan Corp.). Then, a fraction of HSP90 protein concentrates was prepared in a solution containing 50 mM Tris-HCl (pH 7.5) and 20% glycerol as a purified HSP90 solution. The purified HSP90 solution was divided and stored at −80° C. until use.

HSP90-binding activity was determined by an AlphaScreen competitive assay system. The purified HSP90 solution was diluted with a binding buffer (50 mM Tris-HCl (pH 7.5), 150 mM NaCl, 0.1% Triton-X 100, 1 mM DTT, 0.1% BSA) and added to a 384-well plate (#3673, Corning Inc.) containing test substances. After reaction at room temperature for 2 hours, biotinylated geldanamycin was added thereto at a concentration of 40 nM/well and further reacted for 1 hour. Detection mix (20 mM HEPES-KOH (pH 7.5), 0.5% BSA, 0.04 mg/mL Nickel Chelate Acceptor beads, 0.04 mg/mL Streptavidin-coated Donor beads) (#6760619C, PerkinElmer, Inc.) was added to each well in an amount equal to the amount of the reaction solution and reacted at room temperature for 1 hour in the dark. Then, fluorescence intensity was measured using Multilabel Plate Reader EnVision (PerkinElmer, Inc.). Percent inhibition (%) of the binding of biotinylated geldanamycin by each compound of the present invention was determined according to the formula shown below with the fluorescence signal of no test substance addition group as a control. A concentration at which the addition of each compound inhibited the binding of biotinylated geldanamycin to 50% compared with the control was determined ($IC_{50}$ (MM)) and used as a relative index for HSP90 binding.

Percent inhibition (%)=$(C-T)/C \times 100$, wherein
T: Signal of well with test substance addition
C: Signal of well without test substance addition.

As a result, the compounds of the present invention exhibited excellent HSP90-binding activity, whereas none of the comparative compounds exhibited HSP90-binding activity (Table 29).

Test Example 2

Determination of Cell Growth Inhibition

Cell growth was assayed by a crystal violet staining method. SK-BR-3 cells (HTB-30) purchased from American Type Culture Collection were inoculated at a concentration of 5,000 cells/well to a 96-well plate (#353075, BD Biosciences). After culture at 37° C. for 24 hours in a 5% $CO_2$ incubator, each test substance was added thereto, and the cells were further cultured for 72 hours. A 25% glutaraldehyde solution (#17025-25, Nacalai Tesque, Inc.) was added thereto at a concentration of 20 μL/well per 200 μL of the medium, and the plate was incubated at room temperature for 20 minutes to fix the cells. The plate was washed with water and dried. Then, a solution containing 0.05% crystal violet (#038-17792, Wako Pure Chemical Industries, Ltd.) and 20% methanol was added thereto at a concentration of 100 μL/well, and the plate was incubated at room temperature for 20 minutes to stain the cells. The plate was washed with water and dried. A mixed solution of 0.05 M $NaH_2PO_4$ and ethanol (mixed in equal amounts) was added thereto at a concentration of 100 μL/well. Absorbance was measured at 540 nm using a microplate reader (MTP-450, Corona Electric Co., Ltd.) and used as an index for the number of cells per well. Percent inhibition (%) of cell growth by each compound of the present invention was determined according to the formula shown below with the absorbance of no drug addition group as a control. A concentration at which the addition of each compound inhibited the number of cells to 50% compared with the control was determined ($IC_{50}$ (μM)).

Percent inhibition (%)=$(C-T)/C \times 100$, wherein
T: Absorbance of well with test substance addition
C: Absorbance of well without test substance addition.

As a result, the compounds of the present invention inhibited the growth of the breast cancer cells SK-BR-3, whereas none of the comparative compounds inhibited the growth of SK-BR-3 (Table 29).

TABLE 29

| Example | HSP-binding activity IC50 (μM) | Cell growth inhibition IC50 (μM) |
|---|---|---|
| 1 | 0.19 | 0.12 |
| 2 | 0.06 | 0.15 |
| 3 | 0.19 | 0.01 |
| 4 | 0.34 | 0.28 |
| 5 | 1.44 | 0.09 |
| 6 | 0.17 | 0.03 |
| 7 | 0.15 | 0.01 |
| 8 | 0.10 | 0.02 |
| 9 | 0.27 | 0.05 |
| 11 | 0.48 | 0.11 |
| 12 | 0.07 | 0.17 |
| 13 | 0.45 | 0.58 |
| 14 | 1.50 | 0.34 |
| 15 | 0.14 | 0.21 |
| 17 | 0.10 | 0.28 |
| 19 | 2.69 | 0.88 |
| 24 | 0.65 | 0.69 |
| 25 | 0.13 | 0.11 |
| 27 | 0.15 | 0.54 |
| 28 | 0.23 | 0.50 |
| 31 | 0.80 | 0.58 |
| 32 | 0.08 | 0.02 |
| 33 | 0.45 | 0.08 |
| 34 | 0.14 | 0.05 |
| 35 | 1.49 | 0.46 |
| 37 | 0.37 | 0.06 |
| 38 | 0.98 | 0.04 |
| 39 | 0.13 | 0.01 |
| 40 | 0.15 | 0.54 |
| 41 | 0.39 | 1.27 |
| 43 | 0.69 | 1.10 |
| 45 | 0.22 | 0.03 |

TABLE 29-continued

| Example | HSP-binding activity IC50 (μM) | Cell growth inhibition IC50 (μM) |
| --- | --- | --- |
| 48 | 0.07 | 0.02 |
| 49 | 1.56 | 0.40 |
| 52 | 0.28 | 0.11 |
| 53 | 0.12 | 0.04 |
| 54 | 0.47 | 0.48 |
| 56 | 0.37 | 0.47 |
| 58 | 0.25 | 1.44 |
| 59 | 0.10 | 0.09 |
| 60 | 0.17 | 0.15 |
| 61 | 0.19 | 0.07 |
| 62 | 0.21 | 0.26 |
| 63 | 0.27 | 0.03 |
| 64 | 0.17 | 0.01 |
| 65 | 0.22 | 0.01 |
| 66 | 0.15 | 0.02 |
| 67 | 0.21 | 0.02 |
| 68 | 0.19 | 0.01 |
| 69 | 0.15 | 0.02 |
| 70 | 0.21 | 0.06 |
| 71 | 0.17 | 0.21 |
| 72 | 0.74 | 1.74 |
| 73 | 0.19 | 0.07 |
| 74 | 0.44 | 1.12 |
| 75 | 0.21 | 0.33 |
| 76 | 0.20 | 0.04 |
| 77 | 0.17 | 0.01 |
| 78 | 0.18 | 0.03 |
| 79 | 0.32 | 0.02 |
| 80 | 0.14 | 0.02 |
| 81 | 0.87 | 0.76 |
| 83 | 0.21 | 0.10 |
| 84 | 0.22 | 0.11 |
| 85 | 0.31 | 0.42 |
| 86 | 0.10 | 0.01 |
| 87 | 0.28 | 0.08 |
| 88 | 0.35 | 0.07 |
| 89 | 0.22 | 0.01 |
| 90 | 0.58 | 0.03 |
| 91 | 0.23 | 0.01 |
| 92 | 0.79 | 0.02 |
| 93 | 0.10 | 0.02 |
| 94 | 0.50 | 0.11 |
| 95 | 0.40 | 1.02 |
| 96 | 0.14 | 0.06 |
| 97 | 0.16 | 0.02 |
| 98 | 0.08 | 0.02 |
| 99 | 0.27 | 0.04 |
| 100 | 0.34 | 0.26 |
| 101 | 0.12 | 0.12 |
| 102 | 0.25 | 0.63 |
| 103 | 0.12 | 0.01 |
| 104 | 0.06 | 0.01 |
| 105 | 0.40 | 0.02 |
| 106 | 0.10 | 0.00 |
| 107 | 3.39 | 0.24 |
| 108 | 3.75 | 0.34 |
| 109 | 4.36 | 0.21 |
| 110 | 0.38 | 0.10 |
| 111 | 0.84 | 0.06 |
| 112 | 0.50 | 0.02 |
| 113 | 0.08 | 0.01 |
| 114 | 0.07 | 0.01 |
| 115 | 0.14 | 0.01 |
| 117 | 0.29 | 0.05 |
| 118 | 0.25 | 0.06 |
| 119 | 0.83 | 0.84 |
| 120 | 0.19 | 0.03 |
| 121 | 0.18 | 0.02 |
| 122 | 0.09 | 0.01 |
| 123 | 0.16 | 0.01 |
| 124 | 0.13 | 0.02 |
| 125 | 0.16 | 0.01 |
| 126 | 1.53 | 0.35 |
| 127 | 0.21 | 0.05 |
| 128 | 0.31 | 1.06 |
| 129 | 0.09 | 0.01 |
| 130 | 0.11 | 0.06 |
| 131 | 0.26 | 0.14 |
| 132 | 0.32 | 0.96 |
| 133 | 0.84 | 1.32 |
| Comp. Ex. 1 | >100 | 8.42 |
| Comp. Ex. 2 | >100 | >10 |
| Comp. Ex. 3 | >100 | 7.63 |

The invention claimed is:

1. A compound represented by formula (I) or a salt thereof:

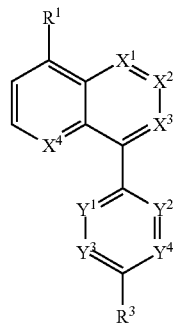

(I)

wherein at least one of $X^1$, $X^2$, $X^3$, and $X^4$ represents N or N-oxide and the rest thereof are the same or different and each represent C—$R^2$;

any one or two of $Y^1$, $Y^2$, $Y^3$, and $Y^4$ represent C—$R^4$ and the rest thereof are the same or different and each represent CH or N;

$R^1$ represents an optionally substituted monocyclic or bicyclic unsaturated heterocyclic group having 1 to 4 heteroatoms selected from the group consisting of N, S, and O;

$R^2$ represents a hydrogen atom, an optionally substituted alkyl group having 1 to 6 carbon atoms, an optionally substituted cycloalkyl group having 3 to 7 carbon atoms, or an optionally substituted alkenyl group having 2 to 6 carbon atoms;

$R^3$ represents a cyano group, or —CO—$R^5$;

$R^4$ represents a hydrogen atom, a halogen atom, an alkyl group having 1 to 6 carbon atoms, an alkoxy group having 1 to 6 carbon atoms, —CO—$R^6$, —N($R^7$)($R^8$), or —S—$R^9$;

$R^5$ represents a hydroxyl group, an amino group, or an optionally substituted alkylamino group having 1 to 6 carbon atoms;

$R^6$ represents a hydroxyl group, an amino group optionally having a hydroxyl group, or an optionally substituted alkylamino group having 1 to 6 carbon atoms;

$R^7$ and $R^8$ are the same or different and each represent a hydrogen atom, an optionally substituted alkyl group having 1 to 6 carbon atoms, an optionally substituted cycloalkyl group having 3 to 7 carbon atoms, an optionally substituted aromatic hydrocarbon group, an optionally substituted saturated heterocyclic group, or an optionally substituted unsaturated heterocyclic group, or $R^7$ and $R^8$ together form a saturated heterocyclic group together with the nitrogen atom bonded thereto; and R$^9$ represents an optionally substituted cycloalkyl group having 3 to 7 carbon atoms, or an optionally substituted aromatic hydrocarbon group.

2. The compound according to claim 1 or a salt thereof, wherein R$^1$ is an optionally substituted monocyclic or bicyclic 5- to 10-membered unsaturated heterocyclic group having 1 to 3 heteroatoms selected from the group consisting of N, S, and O.

3. The compound according to claim 1 or a salt thereof, wherein X$^2$ is C—R$^2$, at least one of X$^1$, X$^3$ and X$^4$ is N or N-oxide and each of the rest of X$^1$, X$^3$ and X$^4$ is CH.

4. The compound according to claim 1 or a salt thereof, wherein R$^2$ is a hydrogen atom; an alkyl group having 1 to 6 carbon atoms and optionally having a substituent selected from the group consisting of a halogen atom and a saturated heterocyclic group; or an optionally substituted cycloalkyl group having 3 to 7 carbon atoms.

5. The compound according to claim 1 or a salt thereof, wherein R$^3$ is a cyano group or —CO—R$^5$ wherein R$^5$ is an amino group or an alkylamino group having 1 to 6 carbon atoms and optionally having an alkylamino group having 1 to 6 carbon atoms, wherein an alkyl moiety is optionally substituted by a hydroxyl group.

6. The compound according to claim 1 or a salt thereof, wherein R$^4$ is a hydrogen atom, a halogen atom, an alkyl group having 1 to 6 carbon atoms, an alkoxy group having 1 to 6 carbon atoms, or —N(R$^7$)(R$^8$)
wherein
R$^7$ is a hydrogen atom, and
R$^8$ is a hydrogen atom; an alkyl group having 1 to 6 carbon atoms and optionally having a substituent selected from the group consisting of an alkoxy group having 1 to 6 carbon atoms, a cycloalkyl group having 3 to 7 carbon atoms, a saturated heterocyclic group, and an unsaturated heterocyclic group; a cycloalkyl group having 3 to 7 carbon atoms and optionally having a substituent selected from a hydroxyl group, an amino group, an aminoacyloxy group, and a saturated heterocyclic acyloxy group; or a monocyclic or bicyclic saturated heterocyclic group having 1 to 4 heteroatoms selected from the group consisting of N, S, and O and optionally having an alkyl group having 1 to 6 carbon atoms.

7. The compound according to claim 1 or a salt thereof, wherein:
Y$^4$ is C—R$^4$ or N and each of Y$^1$ to Y$^3$ is CH, or
each of Y$^2$ to Y$^4$ is CH and Y$^1$ is C—R$^4$.

8. The compound according to claim 1 or a salt thereof, wherein:
X$^2$ is C—R$^2$, X$^4$ is CH, at least one of X$^1$ and X$^3$ is N or N-oxide and the other of X$^1$ and X$^3$ is CH,
Y$^4$ is C—R$^4$ or N and each of Y$^1$ to Y$^3$ is CH, or each of Y$^2$ to Y$^4$ is CH and Y$^1$ is C—R$^4$,
R$^1$ is an optionally substituted monocyclic or bicyclic unsaturated heterocyclic group having 1 to 4 heteroatoms selected from the group consisting of N, S, and O,
R$^2$ is a hydrogen atom; an alkyl group having 1 to 6 carbon atoms and optionally having a halogen atom; or a cycloalkyl group having 3 to 7 carbon atoms,
R$^3$ is —CO—R$^5$ wherein R$^5$ is an amino group, and
R$^4$ is a halogen atom, an alkyl group having 1 to 6 carbon atoms, or —N(R$^7$)(R$^8$)
wherein
R$^7$ is a hydrogen atom, and
R$^8$ is a hydrogen atom; an alkyl group having 1 to 6 carbon atoms and optionally having a substituent selected from the group consisting of an alkoxy group having 1 to 6 carbon atoms, a cycloalkyl group having 3 to 7 carbon atoms, a saturated heterocyclic group, and an unsaturated heterocyclic group; a cycloalkyl group having 3 to 7 carbon atoms and optionally having a substituent selected from a hydroxyl group, an amino group, an aminoacyloxy group, and a saturated heterocyclic acyloxy group; or a monocyclic or bicyclic saturated heterocyclic group having 1 to 4 heteroatoms selected from N, S, and O and optionally having an alkyl group having 1 to 6 carbon atoms.

9. The compound according to claim 1 or a salt thereof, wherein
X$^2$ is C—R$^2$, X$^4$ is CH, at least one of X$^1$ and X$^3$ is N or N-oxide and the other of X$^1$ and X$^3$ is CH,
Y$^4$ is C—R$^4$ or N and each of Y$^1$ to Y$^3$ is CH, or each of Y$^2$ to Y$^4$ is CH and Y$^1$ is C—R$^4$,
R$^1$ is (i) a monocyclic 5- to 6-membered unsaturated heterocyclic group having 1 to 3 heteroatoms selected from the group consisting of N, S, and O and optionally having a substituent selected from the group consisting of an alkyl group having 1 to 6 carbon atoms; an alkylamino group having 1 to 6 carbon atoms; an acylamino group having 1 to 6 carbon atoms and optionally having a hydroxyl group; and an unsaturated heterocyclic group optionally having a substituent selected from the group consisting of an alkyl group having 1 to 6 carbon atoms and a halogenoalkyl group having 1 to 6 carbon atoms, or (ii) a bicyclic 9-to 10-membered unsaturated heterocyclic group having 1 to 3 heteroatoms selected from the group consisting of N, S, and O and optionally having a substituent selected from the group consisting of an alkyl group having 1 to 6 carbon atoms and an acyl group having 1 to 6 carbon atoms,
R$^2$ is a hydrogen atom; an alkyl group having 1 to 6 carbon atoms and optionally having a halogen atom; or a cycloalkyl group having 3 to 7 carbon atoms,
R$^3$ is —CO—R$^5$ wherein R$^5$ is an amino group, and
R$^4$ is a halogen atom, an alkyl group having 1 to 6 carbon atoms, or —N(R$^7$)(R$^8$)
wherein
R$^7$ is a hydrogen atom, and
R$^8$ is a hydrogen atom; an alkyl group having 1 to 6 carbon atoms and optionally having a substituent selected from the group consisting of an alkoxy group having 1 to 6 carbon atoms, a cycloalkyl group having 3 to 7 carbon atoms, a saturated heterocyclic group, and an unsaturated heterocyclic group; or a cycloalkyl group having 3 to 7 carbon atoms and optionally having a substituent selected from the group consisting of a hydroxyl group, an amino group, an aminoacyloxy group, and a saturated heterocyclic acyloxy group.

10. A pharmaceutical composition comprising the compound according to claim 1 or a salt thereof, and a pharmaceutically acceptable carrier.

11. An anticancer agent comprising the compound according to claim 1 or a salt thereof.

* * * * *